(12) United States Patent
Shalek et al.

(10) Patent No.: US 11,427,861 B2
(45) Date of Patent: Aug. 30, 2022

(54) METHODS FOR IDENTIFYING AND MODULATING CO-OCCURANT CELLULAR PHENOTYPES

(71) Applicant: MASSACHUSETTS INSTITUTE OF TECHNOLOGY, Cambridge, MA (US)

(72) Inventors: Alexander K. Shalek, Cambridge, MA (US); Alexander S. Genshaft, Cambridge, MA (US); Carly G. K. Ziegler, Cambridge, MA (US); Jeffrey F. Van Humbeck, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 242 days.

(21) Appl. No.: 16/085,938

(22) PCT Filed: Mar. 17, 2017

(86) PCT No.: PCT/US2017/023054
§ 371 (c)(1),
(2) Date: Sep. 17, 2018

(87) PCT Pub. No.: WO2017/161325
PCT Pub. Date: Sep. 21, 2017

(65) Prior Publication Data
US 2019/0093154 A1 Mar. 28, 2019

Related U.S. Application Data

(60) Provisional application No. 62/309,680, filed on Mar. 17, 2016.

(51) Int. Cl.
| | | |
|---|---|---|
| *C07D 277/04* | (2006.01) | |
| *C07D 277/06* | (2006.01) | |
| *C07D 493/10* | (2006.01) | |
| *C07D 495/04* | (2006.01) | |
| *C07D 513/04* | (2006.01) | |
| *C12Q 1/6837* | (2018.01) | |
| *G01N 33/50* | (2006.01) | |

(52) U.S. Cl.
CPC ......... *C12Q 1/6837* (2013.01); *C07D 277/04* (2013.01); *C07D 277/06* (2013.01); *C07D 493/10* (2013.01); *C07D 495/04* (2013.01); *C07D 513/04* (2013.01); *C12Q 2563/185* (2013.01); *C12Q 2565/514* (2013.01); *C12Q 2565/518* (2013.01); *G01N 33/5005* (2013.01)

(58) Field of Classification Search
CPC .. C07D 277/04; C07D 277/06; C07D 493/10; C07D 495/04; C07D 513/04; C12Q 1/6837; C12Q 2563/185; C12Q 2565/514; C12Q 2565/518; C12Q 2565/51
See application file for complete search history.

(56) References Cited

U.S. PATENT DOCUMENTS

| | | | |
|---|---|---|---|
| 7,041,481 | B2 | 5/2006 | Anderson et al. |
| 7,708,949 | B2 | 5/2010 | Stone et al. |
| RE41,780 | E | 9/2010 | Anderson et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 2007/0195127 | A1 | 8/2007 | Ahn et al. |
| 2008/0003142 | A1 | 1/2008 | Link et al. |
| 2008/0014589 | A1 | 1/2008 | Link et al. |
| 2010/0137163 | A1 | 6/2010 | Link et al. |
| 2010/0172803 | A1 | 7/2010 | Stone et al. |
| 2014/0058058 | A1* | 2/2014 | Song ................ C07D 319/06 558/275 |
| 2014/0170753 | A1 | 6/2014 | Zhang |
| 2014/0179006 | A1 | 6/2014 | Zhang |
| 2014/0179770 | A1 | 6/2014 | Zhang et al. |

(Continued)

FOREIGN PATENT DOCUMENTS

| | | |
|---|---|---|
| AU | 2013-359262 A1 | 7/2015 |
| AU | 2015-101792 A4 | 1/2016 |

(Continued)

OTHER PUBLICATIONS

Bi et al. Angew. Chem. Int. Ed. 2008, 47, 9565-9568. (Year: 2008).*
Chemical Abstract Service STN Database Registry No. 1364917-39-4 [Entered STN: Apr. 4, 2012], (Year: 2012).*
Chemical Abstract Service STN Database Reg. No. 1207736-43-3 [Entered STN: Mar. 3, 2010], (Year: 2010).*
Nguyen et al. "Clickable Poly(ethylene glycol)-Microsphere-Based Cell Scaffolds" Macromol. Chem. Phys. 2013, 214, 948-956. (Year: 2013).*

(Continued)

*Primary Examiner* — Amanda L. Aguirre

(74) *Attorney, Agent, or Firm* — F. Brent Nix, Esq.; Johnson, Marcou, Isaacs & Nix, LLC

(57) ABSTRACT

The present invention provides tools and methods for the systematic analysis of genetic interactions between cells. The present invention provides tools and methods for modulating cell phenotypes and compositions, combinatorial probing of cellular circuits, for dissecting cellular circuitry, for delineating molecular pathways, and/or for identifying relevant targets for therapeutics development.

11 Claims, 29 Drawing Sheets

(56) References Cited

U.S. PATENT DOCUMENTS

| | | | |
|---|---|---|---|
| 2014/0186843 A1 | 7/2014 | Zhang et al. | |
| 2014/0186919 A1 | 7/2014 | Zhang et al. | |
| 2014/0186958 A1 | 7/2014 | Zhang et al. | |
| 2014/0189896 A1 | 7/2014 | Zhang et al. | |
| 2014/0227787 A1 | 8/2014 | Zhang | |
| 2014/0234972 A1 | 8/2014 | Zhang | |
| 2014/0242664 A1 | 8/2014 | Zhang et al. | |
| 2014/0242699 A1 | 8/2014 | Zhang | |
| 2014/0242700 A1 | 8/2014 | Zhang et al. | |
| 2014/0248702 A1 | 9/2014 | Zhang et al. | |
| 2014/0256046 A1 | 9/2014 | Zhang et al. | |
| 2014/0273231 A1 | 9/2014 | Zhang et al. | |
| 2014/0273232 A1 | 9/2014 | Zhang et al. | |
| 2014/0273234 A1 | 9/2014 | Zhang et al. | |
| 2014/0275482 A1* | 9/2014 | Polukhtin | C07D 207/46 530/363 |
| 2014/0287938 A1 | 9/2014 | Zhang et al. | |
| 2014/0310830 A1 | 10/2014 | Zhang et al. | |
| 2016/0153004 A1 | 6/2016 | Zhang et al. | |
| 2016/0251648 A1 | 9/2016 | Wang et al. | |
| 2017/0283831 A1 | 10/2017 | Zhang et al. | |
| 2018/0163265 A1 | 6/2018 | Zhang et al. | |

FOREIGN PATENT DOCUMENTS

| | | |
|---|---|---|
| CN | 102532197 A | 7/2012 |
| CN | 103076312 B | 4/2015 |
| EP | 2 047 910 A2 | 4/2009 |
| EP | 2 771 468 B1 | 2/2015 |
| EP | 2 784 162 B1 | 4/2015 |
| EP | 2 764 103 B1 | 8/2015 |
| WO | 2007/089541 A2 | 8/2007 |
| WO | WO 2010/118235 | 10/2010 |
| WO | 2014/018423 A2 | 1/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2015/065964 A1 | 5/2015 |
| WO | 2015/089351 A1 | 6/2015 |
| WO | 2015/089364 A1 | 6/2015 |
| WO | 2015/089419 A2 | 6/2015 |
| WO | 2015/089465 A1 | 6/2015 |
| WO | 2015/089486 A2 | 6/2015 |
| WO | 2016/049024 A2 | 3/2016 |
| WO | 2016/049163 A2 | 3/2016 |
| WO | 2016/049258 A2 | 3/2016 |
| WO | 2016/094872 A1 | 6/2016 |
| WO | 2016/094874 A1 | 6/2016 |
| WO | 2016/094880 A1 | 6/2016 |
| WO | 2016/106236 A1 | 6/2016 |
| WO | 2016/106244 A1 | 6/2016 |
| WO | 2016/108926 A1 | 7/2016 |
| WO | 2016/205745 A2 | 12/2016 |
| WO | 2017/161325 A1 | 9/2017 |

OTHER PUBLICATIONS

Truong et al. "Photodegradable Gelatin-Based Hydrogels Prepared by Bioorthogonal Click Chemistry for Cell Encapsulation and Release" Biomacromolecules 2015, 16, 2246-2253. (Year: 2015).*

Bi, et al., "Affinity-Based Labeling of Cytohesins with a Bifunctional SecinH3 Photoaffinity Probe," Angewandte Chemie, Wiley-VCH Verlag GMBH & Co., De, 2008, pp. 9565-9568.

Chen, et al., "5-Ethynyl-2'deoxyuridine as a Molecular Probe of Cell Proliferation for High-Content siRNA Screening Assay by Click Chemistry," Science China Chemistry, SP Science China Press, 2011, pp. 1702-1710.

Debets, et al., "Bioorthogonal Labelling of Biomolecules: New Functional Handles and Ligation Methods," Organic & Biomolecular Chemistry, 2013, pp. 6439-6455.

Fomich, et al., "Azide Phosphoramidite in Direct Synthesis of Azide-Modified Oligonucleotides," Organic Letters, 2014, pp. 4590-4593.

Li, et al., "Minimalist Cyclopropene-Contianing Photo-Cross-Linkers Suitable for Live-Cell Imaging and Affinity-Based Protein Labeling," Journal of the American Chemical Society, 2014, pp. 9990-9998.

Ranjitkar, et al., "Affinity-Based Probles Based on Type II Kinase Inhibitors," Journal of the American Chemical Society, Nov. 21, 2012, pp. 19017-19025.

Shi, et al., "Cell-Based Proteome Profiling of Potential Dasatinib Targets by Use of Affinity-Based Probes," Journal of the American Chemical Society, 2012, pp. 3001-3014.

Su, et al., "Azide-Alkyne Cycloaddition for Universal Post-Synthetic Modifications of Nucleic Acids and Effective Synthesis of Bioactive Nucleic Acid Conjugates," Organic & Biomolecular Chemistry, 2014, pp. 6624-6633.

Patel, et al., "Single-cell RNA-seq Highlights Intratumoral Heterogeneity in Primary Glioblastoma", Science, vol. 344, Issue. 6190, Jun. 20, 2014, 13 pages.

Satija, et al., "Heterogeneity in Immune Responses: From Populations to Single Cells", Trends in Immunology, vol. 35, No. 5, May 2014, 219-229.

Qi, et al., "Repurposing CRISPR as an RNA-guided Platform for Sequence-specific Control of Gene Expression" Cell, vol. 152, No. 5, Feb. 28, 2013, 1173-1183.

Massachusetts Institute of Technology, "International Preliminary Report on Patentability received for PCT International Application No. PCT/US2017/023054", dated Sep. 27, 2018, 9 pages.

Massachusetts Institute of Technology, "International Search Report received for PCT Patent International Application Mo. PCT/US2017/023054", dated Jul. 6, 2017, 12 pages.

Bassik, et al., "A Systematic Mammalian Genetic Interaction Map Reveals Pathways Underlying Ricin Susceptibility", Cell, vol. 152, No. 4, Feb. 14, 2013, 28 pages.

Bendall, et al., "Single-Cell Mass Cytometry of Differential Immune and Drug Responses Across a Human Hematopoietic Continuum", Science, vol. 332, No. 6030, May 6, 2011, 23 pages.

Bochet, Christiang., "Photolabile Protecting Groups and Linkers", Journal of the Chemical Society, Perkin Trans. 1, Issue 2, 2002, 124-142.

Buenrostro, et al., "Single-Cell Chromatin Accessibility Reveals Principles of Regulatory Variation", Nature, vol. 523, No. 7561, Jul. 23, 2015, 20 pages.

Buenrostro, et al., "Transposition of Native Chromatin for Fast and Sensitive Epigenomic Profiling of Open Chromatin, DNA-Binding Proteins and Nucleosome Position", Nature Methods, vol. 10, No. 12, Dec. 2013, 15 pages.

Chan, et al., "Mouse Ooplasm Confers Context-Specific Reprogramming Capacity", Nature Genetics, vol. 44, No. 9, Sep. 2012, 8 pages.

Cusanovich, et al., "Multiplex Single Cell Profiling of Chromatin Accessibility by Combinatorial Cellular Indexing", Science, vol. 348, No. 6237, May 22, 2015, 11 pages.

Darmanis, et al., "Simultaneous Multiplexed Measurement of RNA and Proteins in Single Cells", Cell Reports, vol. 14, No. 2, Jan. 12, 2016, 11 pages.

Frei, et al., "Highly Multiplexed Simultaneous Detection of RNAs and Proteins in Single Cells", Nature Methods, vol. 13, No. 3, Mar. 2016, 19 pages.

Gartner, et al., "Programmed Assembly of 3-dimensional Microtissues With Defined Cellular Connectivity", Proceedings of the

(56) References Cited

OTHER PUBLICATIONS

National Academy of Sciences of the United States of America, vol. 106, No. 12, Mar. 24, 2009, 4606-4610.
Genshaft, et al., "Multiplexed Targeted Profiling of Single-Cell Proteomes and Transcriptomes in a Single Reaction", Genome Biology, vol. 17, No. 188, 2016, 16 pages.
Gilbert, et al., "CRISPR-Mediated Modular RNA-Guided Regulation of Transcription in Eukaryotes", Cell, vol. 154, No. 2, Jul. 18, 2013, 20 pages.
Gilbert, et al., "Genome-Scale CRISPR-Mediated Control of Gene Repression and Activation", Cell, vol. 159, Oct. 23, 2014, 647-661.
Hammond, et al., "Profiling Cellular Protein Complexes by Proximity Ligation with Dual Tag Microarray Readout", PLoS One, vol. 7, Issue 7, Jul. 2012, 1-9.
Janssen, et al., "Nucleic Acids for Ultra-Sensitive Protein Detection", Sensors, vol. 13, 2013, 1353-1384.
Johnson, et al., "Genome-Wide Mapping of in Vivo Protein-DNA Interactions", Science, vol. 316, No. 5830, May 31, 2007, 1497-1502.
Keskin, et al., "Transcript-RNA-Templated DNA Recombination and Repair", Nature, vol. 515, Nov. 20, 2014, 18 pages.
Klein, et al., "Droplet Barcoding for Single-Cell Transcriptomics Applied to Embryonic Stem Cells", Cell, vol. 161, No. 5, May 21, 2015, 24 pages.
Konermann, et al., "Genome-Scale Transcriptional Activation by an Engineered CRISPR-Cas9 Complex", Nature, vol. 517, No. 7536, Jan. 29, 2015, 583-588.
Konermann, et al., "Optical Control of Mammalian Endogenous Transcription and Epigenetic States", Nature, vol. 500, No. 7463, Aug. 22, 2013, 18 pages.
Lara-Astiaso, et al., "Chromatin State Dynamics During Blood Formation", Science, vol. 345, Issue 6199, Aug. 22, 2014, 15 pages.
Laufer, et al., "Mapping Genetic Interactions in Human Cancer Cells With RNAI and Multiparametric Phenotyping", Nature Methods, vol. 10, Apr. 7, 2013, 7 pages.
Macosko, et al., "Highly Parallel Genome-Wide Expression Profiling of Individual Cells Using Nanoliter Droplets", Cell, vol. 161, No. 5, May 21, 2015, 25 pages.
Niemeyer, et al., "Detecting Antigens by Quantitative Immuno-PCR", Nature Protocols, vol. 2, No. 8, Aug. 2, 2007, 1918-1930.
Nong, et al., "Solid-Phase Proximity Ligation Assays for Individual or Parallel Protein Analyses with Readout via Real-Time PCR or Sequencing", Nature Protocols, vol. 8, No. 6, Jun. 2013, 1234-1248.
Ogunniyi, et al., "Profiling Human Antibody Responses by Integrated Single-Cell Analysis", Vaccine, vol. 32, No. 24, May 19, 2014, 17 pages.
Pardon, et al., "A General Protocol For the Generation of Nanobodies for Structural Biology", Nature Protocols, vol. 9, No. 3, Mar. 2014, 40 pages.
Parnas, et al., "A Genome-Wide CRISPR Screen in Primary Immune Cells to Dissect Regulatory Networks", Cell, vol. 162, No. 3, Jul. 30, 2015, 24 pages.
Platt, et al., "CRISPR-Cas9 Knockin Mice for Genome Editing and Cancer Modeling", Cell, vol. 159, No. 2, Oct. 9, 2014, 31 pages.
Rabani, et al., "High-Resolution Sequencing and Modeling Identifies Distinct Dynamic RNA Regulatory Strategies", Cell, vol. 159, Nov. 15, 2014, 1698-1710.
Rabani, et al., "Metabolic Labeling of RNA uncovers principles of RNA production and degradation dynamics in mammalian cells", Nature Biotechnology, vol. 29, No. 5, May 2011, 47 pages.
Ran, et al., "Double Nicking by RNA-Guided CRISPR Cas9 for Enhanced Genome Editing Specificity", Cell, vol. 154, No. 6, Sep. 12, 2013, 19 pages.
Ran, et al., "In Vivo Genome Editing using *Staphylococcus aureus* Cas9", Nature, vol. 520, No. 7546, Apr. 1, 2015, 30 pages.
Sanjana, et al., "Improved Vectors and Genome-Wide Libraries for CRISPR Screening", Nature Methods, vol. 11, No. 8, Aug. 2014, 5 pages.
Satija, et al., "Spatial Reconstruction of Single-Cell Gene Expression Data", Nature Biotechnology, vol. 33, No. 5, May 2015, 495-502.
Selden, et al., "Chemically Programmed Cell Adhesion with Membrane-Anchored Oligonucleotide", Journal of the American Chemical Society, vol. 134, No. 2, Jan. 18, 2012, 10 pages.
Shalek, et al., "Single-Cell RNA-Seq Reveals Dynamic Paracrine Control of Cellular Variation", Nature, vol. 510, Jun. 19, 2014, 363-369.
Shalek, et al., "Vertical Silicon Nanowires as a Universal Platform for Delivering Biomolecules Into Living Cells", Proceedings of the National Academy of Sciences, vol. 107, No. 5, Feb. 2, 2010, 1870-1875.
Shalem, et al., "Genome-Scale CRISPR-Cas9 Knockout Screening in Human Cells", Science, vol. 343, No. 6166, Jan. 3, 2014, 10 pages.
Shalem, et al., "High-Throughput Functional Genomics Using CRISPR-Cas9", Nature Reviews Genetics, vol. 16, No. 5, May 2015, 28 pages.
Shmakov, et al., "Discovery and Functional Characterization of Diverse Class 2 CRISPR-Cas Systems", Molecular Cell, vol. 60, No. 3, Nov. 5, 2015, 385-397.
Smith, et al., "A Unique Regulatory Phase of DNA Methylation in the Early Mammalian Embryo", Nature, vol. 484, No. 7394, Mar. 28, 2012, 21 pages.
Smith, et al., "DNA Methylation Dynamics of the Human Preimplantation Embryo", Nature, vol. 511, Jul. 31, 2014, 34 pages.
Stahlberg, et al., "Quantitative PCR Analysis of DNA, RNAs, and Proteins in the Same Single Cell", Clinical Chemistry, vol. 58, No. 12, Dec. 2012, 1682-1691.
Tehranirokh, "Microfluidic Devices for Cell Cultivation and Proliferation", Biomicrofluidics, vol. 7, No. 5, Oct. 29, 2013, 33 pages.
Theile, et al., "Site-Specific N-Terminal Labeling of Proteins Using Sortase-Mediated Reactions", Nature Protocols, vol. 8, No. 9, Sep. 2013, 13 pages.
Todhunter, et al., "Programmed Synthesis of Three-Dimensional Tissues", Nature Methods, vol. 12, No. 10, 2015, 18 pages.
Twite, et al., "Direct Attachment of Microbial Organisms to Material Surfaces Through Sequence-Specific DNA Hybridization", Advanced Materials, vol. 24, No. 18, May 8, 2012, 2380-2385.
Wang, et al., "One-Step Generation of Mice Carrying Mutations in Multiple Genes by CRISPR/Cas-Mediated Genome Engineering", Cell, vol. 153, No. 4, May 9, 2013, 13 pages.
Weber, et al., "Efficient Targeting of Fatty-Acid Modified Oligonucleotides to Live Cell Membranes through Stepwise Assembly", Biomacromolecules, vol. 15, No. 12, Dec. 8, 2014, 4621-4626.
Zetsche, et al., "Cpf1 is a Single RNA-Guided Endonuclease of a Class 2 CRISPR-Cas System", Cell, vol. 163, No. 3, Oct. 22, 2015, 759-771.

\* cited by examiner

"Macro"-environment (>$10^4$ cells)
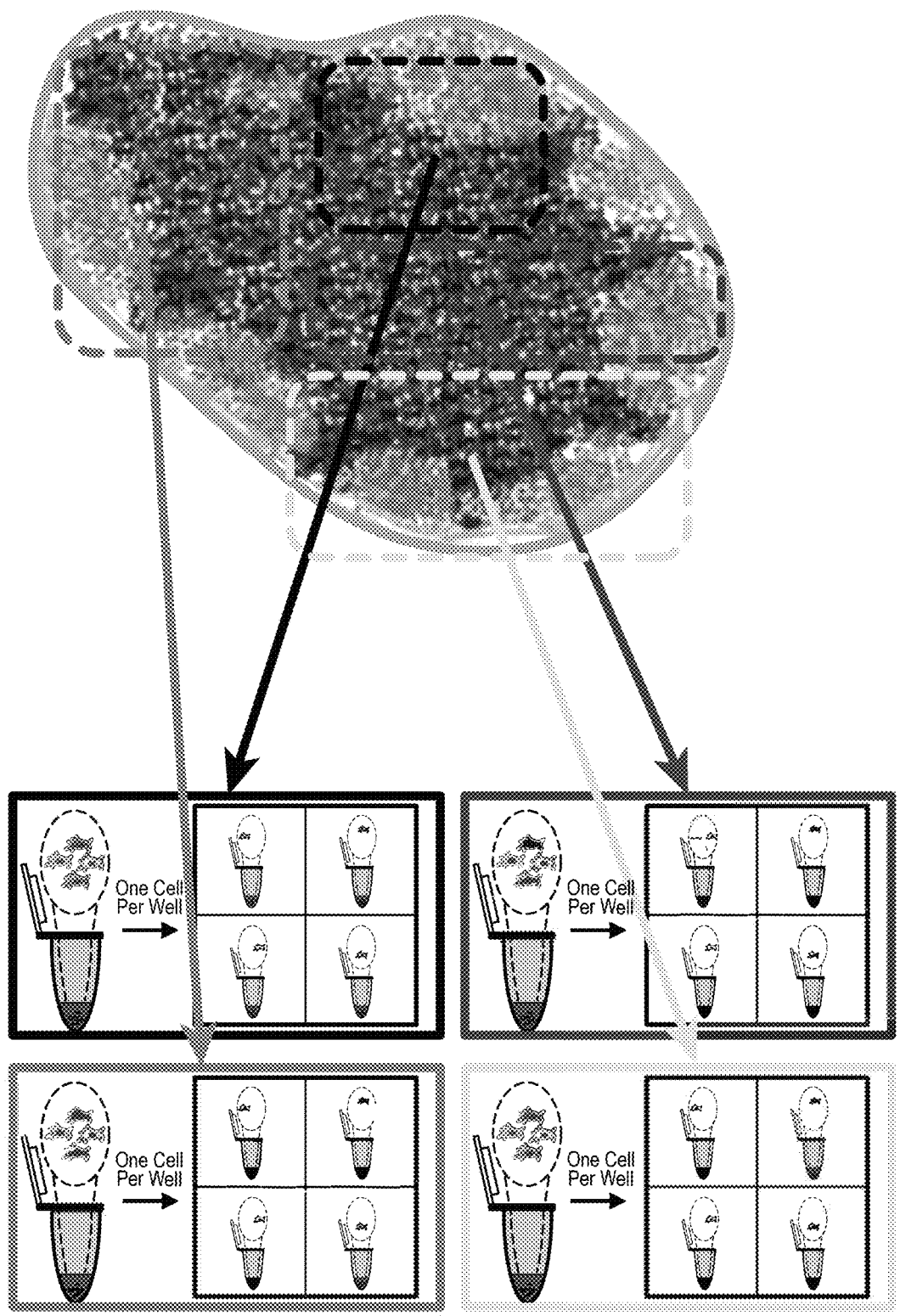
FIG. 13A Continuation

"Macro"-environment (2-10$^2$ cells)

METHODS FOR IDENTIFYING AND MODULATING CO-OCCURANT CELLULAR PHENOTYPES

INCORPORATION BY REFERENCE

This application claims priority and benefit of U.S. provisional application Ser. No. 62/309,680 filed Mar. 17, 2016, incorporated herein by reference.

All documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to molecular profiling at the single-cell level as well as populations of cells. The present application provides a spatially-resolved single-cell RNA sequencing (scRNA-Seq) approach to link neighboring cell states/phenotypes and use it to propose extracellular regulators (microenvironmental factors, cell-cell interactions) of cellular behaviors, which can be validated and screened for clinical relevance. The present invention also enables a systematic, "on-the-fly" technique for spatially patterning and/or barcoding cells on a surface (e.g. inorganic, organic, or biological) in a user-desired arrangement with the ability to later release target cells via enzymatic, chemical, and/or photo-cleavable methods. Additionally, the present invention is relevant for therapeutics target discovery.

BACKGROUND OF THE INVENTION

While the cell is the least common denominator of life, a multicellular organism would not function with its constituent cells acting in isolation. Intercellular communication, both at a distance and via direct contact, is crucial to performing all of life's functions—from neurons telling muscle cell to contract and embryonic stem cells differentiating to immune cells coordinating systems-level defenses. Nevertheless, the impact of cell-to-cell communication on cellular phenotypes remains an understudied, and poorly understood, area of biology. The following examples and descriptions are placed in the context of the immune system and related examples, but are not intended to be limited to these systems. Rather they are meant to encompass any and all cells and cellular interactions.

Immune cells are the primary defenders of our bodies against illness. Precision and accuracy in their actions are crucial for our health: failure to sense and respond can make us susceptible to illness, while inappropriate sensing can lead to autoimmune disease. Understanding the molecular circuits that control immune cell behaviors is a fundamental biological goal offering untold clinical possibilities.

Cellular heterogeneity is a hallmark of the immune system and is essential for protecting us against myriad, evolving pathogenic threats. Thus, immune isolates from clinical samples, such as biopsies, blood, and synovia, all consist of complex cell mixtures. To date, genomic analyses of clinical samples have relied on either profiling this heterogeneous mixture or first sorting sub-populations and then profiling them. The former strategy only provides an average, teaching us more about the component cell types than their states; the latter is limited to known sub-populations and sorting panels, can be difficult to implement for small samples (<1 million cells), and masks any variation within the sub-population, which can be substantial. Indeed, recent approaches for deciphering complex cell circuits combine genomic profiling to measure a circuit's components or interactions, computational algorithms to infer a model from those profiles and perturbation techniques (e.g., RNAi) to test and refine it. However, there are two major challenges in applying this strategy to primary immune cells. First, naïve immune cells are notoriously difficult to perturb with traditional transfection methods. Second, a typical immune-cell population contains many different cell subtypes and states and ensemble-based profiling methods cannot accurately measure the population's constituents, much less how their coordinated behaviors determine systems-level responses. These two hurdles have severely limited understanding of the circuits that dictate immune-cell development, behavior, response and function, in both healthy and diseased states.

Citation or identification of any document in this application is not an admission that such document is available as prior art to the present invention.

SUMMARY OF THE INVENTION

The invention comprehends a method to develop and leverage a novel platform for spatially-resolved single cell genomic profiling of tissues to identify novel intercellular communication genes and gene-products, more specifically immune evasion genes or gene-products from intratumoral heterogeneity. This method provides an integrated, single platform to measure changes in gene expression directly from single cells. The connection between intratumoral heterogeneity and local immune cell phenotypes is lost when averaging across a population (e.g., a large piece of tumor) or disaggregating tissues for single-cell RNA-Seq (scRNA-Seq). The present application provides a spatially-resolved scRNA-Seq approach—or general method for spatially resolved cellular profiling—to link neighboring cell states/phenotypes and use it to propose regulators of immune cell suppression, which can be validated and screened for clinical relevance.

The ability to evade immune attack is one of the cardinal features of cancer (Hanahan, D. & Weinberg, R. A. "Hallmarks of Cancer: The Next Generation" *Cell* 144, 646-674, doi:10.1016/j.cell.2011.02.013 (2011)), but it is a trait that is heterogeneous across a population of tumor cells. Single-cell profiling of tumors has begun to reveal the existence of multiple sub-states of tumor cells (Patel, A. P. et al. "Single-cell RNA-seq highlights intratumoral heterogeneity in primary glioblastoma" *Science* 20, 1396-1401, doi:10.1126/science.1254257 (2014)), but two crucial gaps remain in the understanding of intratumoral heterogeneity. First, the repertoire of immune-evasion mechanisms utilized by tumor cells is not known, and how it differs across distinct tumor regions. Second, it is not known whether heterogeneity in the expression of immune evasion molecules by individual tumor cells impacts the state of tumor infiltrating lymphocytes (TIL) locally or globally.

Specifically, the invention provides a method to develop and leverage an innovative platform for spatially-resolved, single-cell genomic profiling of tissues to identify novel immune evasion genes from intratumoral heterogeneity. Applicants have developed a robust experimental platform for spatially tagging cells in tumor sections with unique sets of oligonucleotides prior to scRNA-Seq. By linking neighboring tumor and immune cell behaviors, Applicants identify TIL states and their correlation with local tumor cell gene expression. Using this workflow, Applicants are able to identify candidate tumor cell genes that alter the number and differentiation state of local immune infiltrates.

The present application also provides a method to perturb candidate immune evasion molecules to validate their effects on tumor immunity. Applicants use over-expression (lentivirus or CRISPRa) and knockout (CRISPRi)—or other biological or chemical perturbation methods known to the art—to test and validate the putative immune evasion genes identified in the foregoing. Applicants use pooled screens to monitor for the selective survival of modified tumor cells in the presence of immune pressure, assessing how overexpression/knockout of immune evasion genes causes selective accumulation/loss of genetically modified tumor cells relative to wild-type counterparts. For genes that score in these screens, Applicants thoroughly characterize their roles in tumor immunity by microscopy, flow cytometry, and scRNA-Seq. In parallel, Applicants also perturb and characterize predicted regulators in immune cells.

The present application also provides tools to spatially pattern cells on a surface (e.g. inorganic, organic, or biological) in a user-directed fashion. Applicants and others can use the molecular platform described herein to control the arrangement of cells and control release via enzymatic, chemical, and/or photo-cleavable means for downstream genomic profiling.

Applicants also developed a method to map intratumoral heterogeneity of cancer and immune cells in clinical melanoma samples. Direct interactions between TILs and malignant (e.g., melanoma) cells, TILs and stromal cells, or malignant and non-malignant cells may have major implications for disease progression and treatment strategies in the clinic.

The immune system plays a crucial role in fighting cancer. The large number of genetic alterations inherent to most cancer cells provides myriad tumor-associated neo-antigens that the host immune system can recognize (Yadav, M. et al. Predicting immunogenic tumour mutations by combining mass spectrometry and exome sequencing. Nature 515, 572-576, doi:10.1038/nature14001 (2015)). Nevertheless, the coexpression of surface and secreted molecules by tumor cells has been shown to confer tumors with the ability to evade immune responses (Fridman, W. H., et al. The immune contexture in human tumours: impact on clinical outcome. Nature Reviews Cancer 12, 298-306, doi:10.1038/nrc3245 (2012)). Several recent trials (Victor, C. T.-S. et al. Radiation and dual checkpoint blockade activate non-redundant immune mechanisms in cancer. Nature, 1-18, doi:10.1038/nature14292 (2015); Ott, P. A., et al. CTLA-4 and PD-1/PD-L1 Blockade: New Immunotherapeutic Modalities with Durable Clinical Benefit in Melanoma Patients. Clin. Cancer Res. 19, 5300-5309, doi:10.1158/1078-0432.CCR-13-0143 (2013); Tumeh, P. C. et al. PD-1 blockade induces responses by inhibiting adaptive immune resistance. Nature 515, 568-571, doi:10.1038/nature13954 (2014)) have demonstrated that blocking immune checkpoint receptors (normally engaged by tumor cells to suppress immune responses) can generate striking clinical responses against a range of tumors. However, the clinical impact of tumor immunity in patients with cancer is variable and many patients fail to respond to immunotherapy (Victor et al. 2015; Ott et al. 2013; Tumeh et al. 2014). Overall, the cellular and molecular mechanisms that result in response or resistance to immunotherapy are poorly understood.

Cancer cells, even from the same tumor, are highly heterogeneous (due to somatic evolution, genomic instability, and differences in epigenetic state (Patel et al. Science 2014; Driessens, G., Beck, B., Caauwe, A., Simons, B. D. & Blanpain, C. Defining the mode of tumour growth by clonal analysis. Nature 488, 527-530, doi:10.1038/nature11344 (2013); Gerlinger, M. et al. Intratumor Heterogeneity and Branched Evolution Revealed by Multiregion Sequencing. The New England journal of medicine 366, 883-892, doi:10.1056/NEJMoa1113205 (2012); Navin, N. et al. Tumour evolution inferred by single-cell sequencing. Nature 472, 90-94, doi:10.1038/nature09807 (2012); Schepers, A. G. et al. Lineage Tracing Reveals Lgr5+ Stem Cell Activity in Mouse Intestinal Adenomas. Science (New York, N.Y.) 337, 730-735, doi:10.1126/science.1224676 (2012); Yachida, S. et al. Distant metastasis occurs late during the genetic evolution of pancreatic cancer. Nature 467, 1114-1117, doi:10.1038/nature09515 (2010); Eppert, K. et al. Stem cell gene expression programs influence clinical outcome in human leukemia. Nature Medicine 17, 1086-1093, doi:10.1038/nm.2415 (2011)) and this variability has been shown to underscore drug resistance and tumor relapse (Bedard, P. L., Hansen, A. R., Ratain, M. J. & Siu, L. L. Tumour heterogeneity in the clinic. Nature 501, 355-364, doi:10.1038/nature12627 (2013); Marusyk, A., Almendro, V. & Polyak, K. Intra-tumour heterogeneity: a looking glass for cancer? Nature Reviews Cancer 12, 323-334, doi:10.1038/nrc3261 (2012)). Increasing evidence suggests that there is also intratumoral heterogeneity in the ability of tumor cells to evade immunity. First, infiltrating immune cells are often not evenly dispersed throughout the tumor, but instead are clustered (Azimi, F. et al. Tumor-infiltrating lymphocyte grade is an independent predictor of sentinel lymph node status and survival in patients with cutaneous melanoma. J Clin Oncol 30, 2678-2683, doi:10.1200/JCO.2011.37.8539 (2012)). Second, the expression of immune evasion genes, such as PD-L1, is not monomorphic throughout a tumor, but rather is restricted to a sub-population of cells (Tumeh et al. 2014; Topalian, S. L. et al. Safety, Activity, and Immune Correlates of Anti-PD-1 Antibody in Cancer. The New England Journal of Medicine 366, 2443-2454, doi:10.1056/NEJMoa1200690 (2012)). These data suggest that there is geographic variation in the tumor gene expression and mutation burden that drives immune activity and the interactions between tumor and immune cells. However, the basis for these regional enrichments or paucities is not known, nor is their significance for tumor biology or clinical course.

The following further underscores some of the intricacies involved when studying health and disease, including host-pathogen interactions, as well as host-specific diversity associated with particular cell types, or cell type subpopulations. It is thus clear that there is a need in the art to further unravel complex immune system heterogeneity and synergies, in particular to establish cellular networks and cell interactions, aiming at improving diagnostic or therapeutic efforts.

The invention comprehends, and the invention provides each aspect as discussed herein below:

The invention comprehends providing a cell functionalizing probe comprising a polyadorned molecule, wherein the molecule is adorned with anywhere from 2 to 5 groups: optionally a label attached to the polyadorned molecule; a cell-surface reactive group attached to the polyadorned molecule, wherein the reactive group is selectively activated by light or any other method known in the art; a bio-orthogonal reactive group attached to the polyadorned molecule; optionally a second reactive group attached to the polyadorned molecule; and, optionally a group to improve water solubility. In an embodiment of the invention, the polyadorned molecule of the cell functionalizing probe is a single aromatic molecule, e.g., benzene, dihydroxyaryl or triazine. In another embodiment of the invention, the polyadorned molecule of the cell functionalizing probe comprises a functional moiety, e.g., NHCO, NHCCH2, NHCN, or NHCS. In another embodiment, the label of the cell-surface functionalizing probe is a fluorophore, a peptide based-tag, biotin, affinity reagent, hapten, lanthanide heavy metal (or lanthanide heavy metals or combination thereof) or an oligonucleotide. In an embodiment of the invention, the bio-orthogonal reactive group of the cell functionalizing probe is an alkyne, strained alkyne, alkene, or strained alkene. The present application contemplates cell functionalizing probes which can be activated via copper chemistry, copper-free chemistry, photoclick chemistry, or synthesized by inverse-demand Diels Alder.

By adornment is meant addition to or presence of a functional moiety, or substituent, linked to a molecular core. In certain non-limiting embodiments, the molecular core is aromatic, for example, with limitation, benzene, dihydroxyaryl, and triazine. A cell functionalizing probe of the invention is said to be "polyadorned" in that the probe comprises a molecular core substituted with 2 or more functional substituents as set forth herein. In an embodiment of the invention, the two or more substituents comprise a cell-surface reactive group, for instance in a non-limiting example a cell-surface reactive group that is selectively activated by light, and a bio-orthogonal substituent, for instance in a non-limiting example a bio-orthogonal substituent capable of being linked by click chemistry to a moiety comprising a polynucleotide barcoded tag. Bio-orthogonal is used in its usual sense and refers to a substituent functional in a living system that does not interfere substantially with native biochemical processes.

In an embodiment, the cell functionalizing probe comprises a reactive group, wherein the reactive group is a photoactivated cell-surface reactive group. In another embodiment, the photoactivated cell-surface reactive group of the cell functionalizing probe is a benzophenone, azide, or diazirine, wherein the group is activated to become a carbon-centered radical, nitrene, or carbene, respectively.

In an aspect of the invention, the invention provides a cell functionalizing barcoded tag comprising a polyadorned molecule, wherein the molecule is adorned with anywhere from 2 to 5 groups; a fluorophore, peptide-based tag, biotin, hapten, affinity reagent, lanthanide heavy metal(s) or combination thereof, or oligonucleotide label attached to the polyadorned molecule; a paired bio-orthogonal reactive group to the bio-orthogonal group of the cell functionalizing probe (e.g., azide, nitrone, tetrazine, or tetrazole attached to the polyadorned molecule); and, an oligonucleotide, fluorophore, peptide, affinity reagent, biotin or other specific barcode comprising a spatial barcode (in an embodiment this consists of a scRNA-seq compatible handle), wherein the barcode is attached to the polyadorned molecule. In another embodiment, the label of the cell functionalizing barcoded tag is a fluorophore, a peptide-based tag, biotin, or a cyanine-based dye. Examples of peptide-based tag comprises FLAG-tag, V5 tag, HA-tag, AviTag, Calmodulin-tag, polyglutamate tag, E-tag, His-tag, Myc-tag, S-tag, SBP-tag, Softag 1, Softag 3, Strep-tag, TC tag, VSV-tag, or Xpress tag, or any other similar tag known in the art. In another embodiment, the scRNA-seq method is smart-seq2, TruSeq, CEL-Seq, Drop-Seq, In-drop Seq, STRT, ChIRP-Seq, GRO-Seq, CLIP-Seq, Quartz-Seq, or any other similar method known in the art (see, e.g., "Sequencing Methods Review" Illumina® Technology, https://www.illumina.com/content/dam/illumina-marketing/documents/products/research_reviews/sequencing-methods-review.pdf.

In another aspect, the invention provides a cell functionalizing barcoded tag comprising 2 to 5 functional moieties. In an embodiment, the barcoded tag comprises a label selected from the group consisting of fluorophore, peptide-based tag, biotin, hapten, affinity reagent, lanthanide heavy metal(s) or combination thereof, or oligonucleotide. In another embodiment, the label of the cell functionalizing barcoded tag is a fluorophore, a peptide-based tag, biotin, or a cyanine-based dye. In another embodiment, the barcoded tag a paired bio-orthogonal reactive group to the bio-orthogonal group of the cell functionalizing probe (e.g., azide, nitrone, tetrazine, or tetrazole attached to the polyadorned molecule). In another embodiment, the barcoded tag comprises an oligonucleotide, fluorophore, peptide, affinity reagent, biotin or other specific barcode comprising a space barcode or an elongated space barcode, optionally a 5' handle, and optionally a poly A tail.

In another aspect, the invention provides a cell functionalizing barcoded tag ("oligo tag") for patterning surfaces.

In another aspect, the invention provides a continuous method of single-cell profiling in a subject in need thereof wherein the single cells are spatially resolved, the method comprising (a) saturating cells in the subject in need thereof with a cell functionalizing probe; (b) activating the cell functionalizing probe with light (e.g., UV); (c) labelling cells with a cell functionalizing barcoded tag; (d) washing the tissue with an aqueous solution, wherein the solution removes extra functionalizing probe; (e) repeating steps (a) through (d) anywhere from 1 to about 100 (and potentially more) times, (f) separating the labeled cellular ensemble (e.g., a tissue) into a suspension of single cells or small cell aggregates by any method known in the art; (g) optionally sorting and enriching cells comprising a cell functionalizing tag and cell functionalizing probe via flow cytometry or any cell separation method (e.g. magnetic isolation) known to the art; (h) profiling single cell sequences, whole cell populations, or cell subpopulations; and, (i) optionally assembling the single cell sequences into a visual representation, wherein the relationship between amplified shared spatial barcodes of single cell sequences is obtained by a computational method; and, (j) analyzing cellular phenotypes using categorical spatial information.

In an aspect of the invention, the present application provides a continuous method of single-cell profiling in a subject in need thereof wherein the single cells are spatially resolved, the method comprising: (a) conjugating a cell functionalizing probe to a cell functionalizing barcoded tag, whereby an active complex is formed; (b) saturating tissue in the subject in need thereof with the active complex as described according to the cell functionalizing probes provided herein; (c) activing the cell functionalizing probe; (d) washing the tissue with an aqueous solution, wherein the solution removes excess active complex; (e) repeating steps (a) through (d) anywhere from 1 to 100 times; (f) separating the labeled cellular ensemble (e.g., a tissue) into a suspension of single cells or small cell aggregates; (g) optionally sorting and enriching cells comprising a cell functionalizing tag and a cell functionalizing probe via a cell separation method; (h) profiling single cell sequences; (i) optionally assembling the single cell sequences into a visual representation, wherein the relationship between amplified shared spatial barcodes of single cell sequences is obtained by a computational method; and (j) optionally using spatial information as a categorical variable for downstream computational analysis.

In another aspect, the invention provides a method for spatially patterning specific cells on surfaces (e.g. inorganic, organic, or biological). This is currently achievable (Todhunter et al. Nature Methods 2015), however Applicants' method has the specific advantage of enabling user-defined cellular placement that can be adjusted in real-time as opposed to pre-printing of oligonucleotides on surfaces. In an embodiment of this method, the cell functionalized barcode would be conjugated to cells using a non-specific, e.g., NHS-ester ligation or cholesterol (3' cholesterol-TEG) or specific chemistry and the surface would be patterned with the cell functionalized probe (via photoactivation or another user-controlled activation scheme). By flowing the barcoded cells over the surface, some will be attached via the click (or other) functionalization paired on both molecules. In another embodiment of this method, the surface is patterned with the cell functionalized probe labeled with an oligonucleotide; cells can then be flowed over (streamed) and conjugated non-specifically (e.g. via NHS-ester ligation) or specifically. In an aspect of the invention, whole tissues or vibratome-sliced portions of biopsied human samples or whole mouse organ can be directly applied onto pre-barcoded surfaces. In another embodiment of this method the surface is patterned with the cell functionalized probe labeled with an oligonucleotide and cells labeled with complementary oligonucleotides can then be adhered to the surface in a specific manner.

In another aspect, the invention provides a method of spatially patterning cells on surfaces wherein single cells are spatially localized, the method comprising: (a) assembling a cell functionalized barcode conjugated to cell(s); (b) assembling a surface patterned with a cell functionalized probe; and a surface, wherein the surface is patterned with a cell functionalized probe; (c) streaming cells conjugated with a cell functionalized barcode over the surface patterned with a cell functionalized probe, whereby cells are attached to the cell functionalized probe via complementary pairing chemistry. In an embodiment, the complementary pairing chemistry is click functionalizing pairing or oligonucleotide complementarity.

In another aspect, the invention provides a method of spatially patterning cells on surfaces wherein single cells are spatially localized, the method comprising: (a) assembling a cell functionalized barcode conjugated to cell(s); (b) assembling a surface (biological, inorganic, or organic) patterned with a cell functionalized probe, wherein the surface is patterned with a cell functionalized probe labelled with an oligonucleotide; (c) streaming cells conjugated with a cell functionalized barcode over the surface patterned with a cell functionalized probe, whereby cells are conjugated non-specifically; and, (d) optionally analyzing cellular phenotypes using spatial information. In an embodiment, the complementary pairing chemistry is click functionalizing pairing or oligonucleotide complementarity.

In another aspect, the invention provides a method of spatially patterning cells on surfaces wherein single cells are spatially localized, the method comprising: (a) assembling a cell functionalized barcode conjugated to cell(s); (b) assembling a surface (biological, inorganic, or organic) with a cell functionalized probe, wherein the surface is patterned with the cell functionalized probe is labelled with complementary oligonucleotides; (c) streaming cells conjugated with a cell functionalized probe over the surface, whereby cells are conjugated specifically; and, (d) optionally analyzing cellular phenotypes using spatial information. In an embodiment, the complementary pairing chemistry is click functionalizing pairing or oligonucleotide complementarity.

In an another aspect, the invention provides a method for a cell functionalizing probe or a cell functionalizing barcoded tag, wherein the bio-orthogonal reactive group comprises a compound of Formula (I):

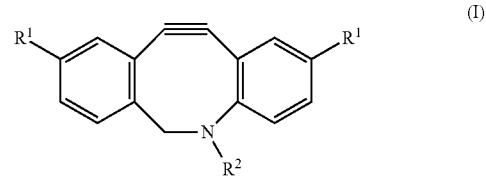

wherein $R^1$ is selected from the group consisting of —H, —X, —$(CH_2)_a$—NH-$PG^1$, —O—$(CH_2CH_2O)_a$C $CH_2)_c$ $NH_2$—$PG^1$, —O—$(CH_2CH_2O)_a$—$PG^2$-$(CH_2)_a$—O-$PG^2$;
$R^2$ is selected from the group consisting of $CO(CH_2)_a$NHCO $(CH_2)_a$O$(CH_2CH_2O)_c$$(CH_2)_a$NHR$^{21}$—; $R^{21}$ is selected from the group consisting of —H, —O($C_1$-$C_6$ alkyl), —$C_1$-$C_8$ straight chain alkyl, —$C_1$-$C_8$ branched alkyl, —$C_2$-$C_8$ alkenyl, —$C_2$-$C_8$ alkynyl, —($C_1$-$C_6$ alkyl)-O— ($C_1$-$C_6$ alkyl);
$PG^1$ is an amine protecting group or —H;
$PG^2$ is an alcohol protecting group or —H;
X is selected from the group consisting of Cl, Br, I, F;
  a is independently any integer between 0 and 6;
  c is independently any integer between 1 and 6.

In an embodiment of the invention, $PG^1$ is any amine protecting group known to one of skill in the art. Mention is made of T. W. Greene & P. G. M. Wuts *Protective Groups in Organic Synthesis* (4th edition) J. Wiley & Sons (2006) and P. J. Kocienski *Protecting Groups* Georg Thieme Verlag (1994) herein incorporated by reference. Embodiments of protecting groups include, but are not limited to:

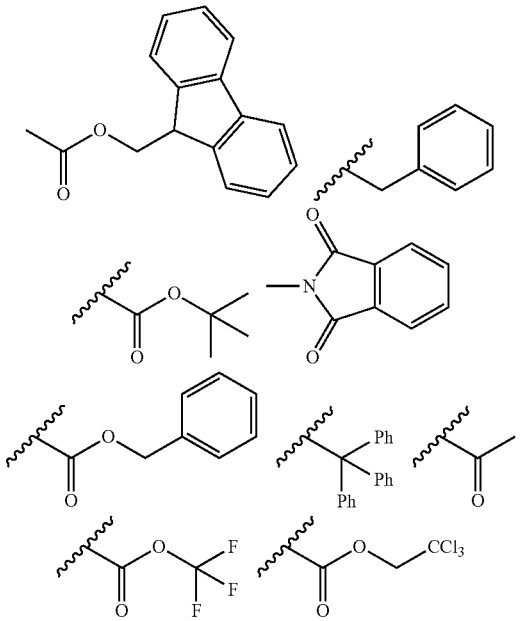

-continued

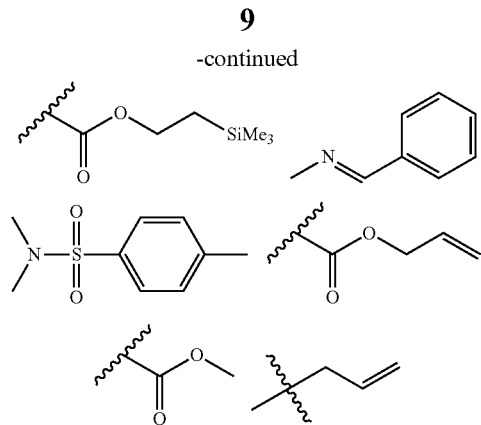

In an embodiment of the invention, PG² is any alcohol protecting group known to one of skill in the art. Mention is made of T. W. Greene & P. G. M. Wuts *Protective Groups in Organic Synthesis* (4th edition) J. Wiley & Sons (2006) and P. J. Kocienski *Protecting Groups* Georg Thieme Verlag (1994) herein incorporated by reference. Embodiments of protecting groups include, but are not limited to:

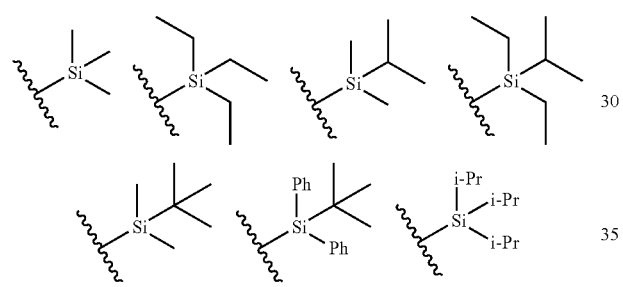

or any silyl ether thereof,

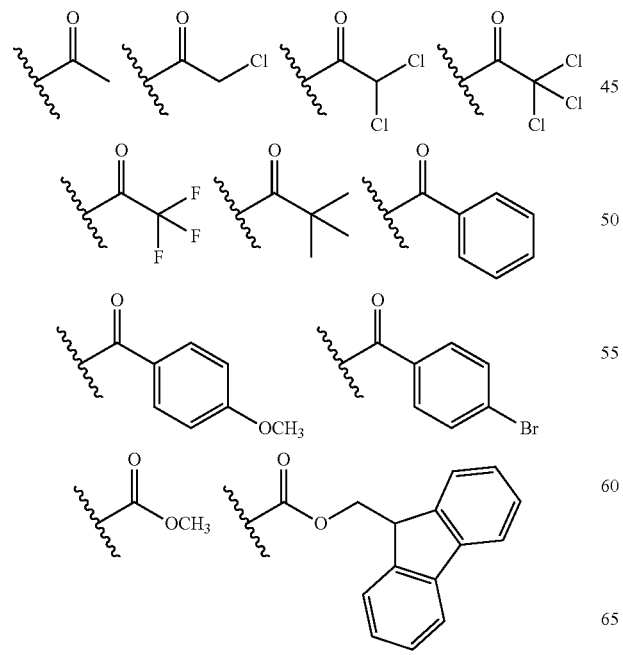

-continued

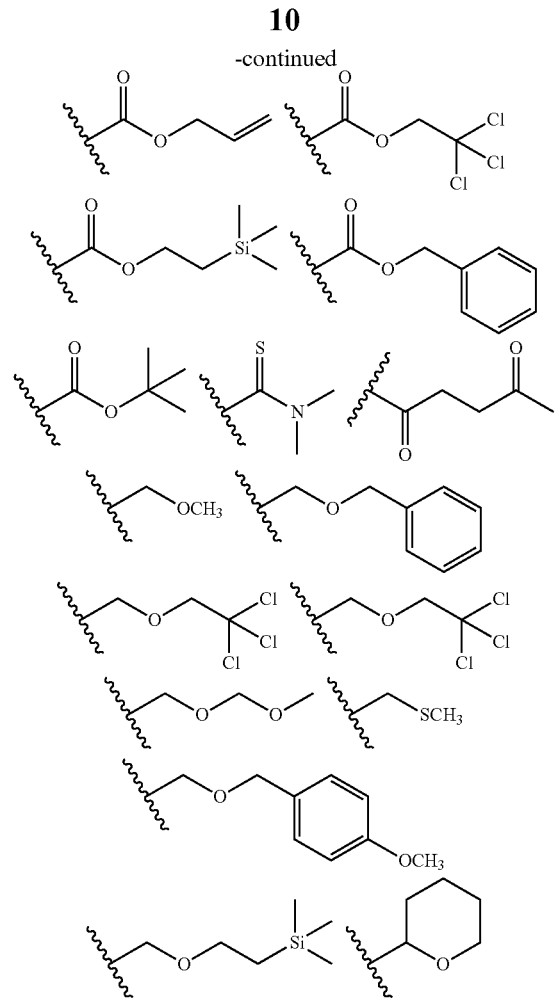

In an another aspect, the invention provides a method for a cell functionalizing probe or a cell functionalizing barcoded tag wherein the fluorophore comprises a compound of Formula II:

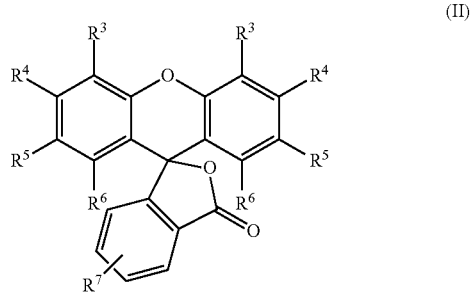

(II)

wherein $R^3$ is selected from the group consisting of —H, $C_1$-$C_6$ alkyl, —$(CH_2)_a$—$NR^8R^9$, —NHC(O)—Y—$R^8$, —NHC(O)CHR⁸R⁹, —CHR⁸R⁹; —$(CH_2)_a$—$NR^8C(O)R^9$, $R^4$ is selected from the group consisting of —H, —OH, and —OR⁸;

$R^5$ and $R^6$ are selected from the group consisting of —H, —OH, —X, —NO₂, —CN, —NH₂, —NHR⁸; —C(O)R⁸, —$C_1$-$C_3$ perfluoro alkyl; $R^7$ is selected from the group consisting of —H, —OH, —X, —NO₂, —CN, —C(O)NH —(CH$_2$)a —O(C$_1$-C$_6$ alkyl), —NH$_2$, —NHR$^8$, —NHC(O)—Y—R$^8$, —(CH$_2$)$_a$—NR$^{68}$C(O)R$^9$, —NHC(O)CHR$^8$R$^9$, —C$_1$-C$_3$ perfluoro alkyl;

R$^8$ and R$^9$ are independently selected from the group consisting of —H, NH$_2$, —(CH$_2$)$_a$—C(O)NH(CH$_2$)$_b$CH$_3$, —(CH$_2$)$_a$—C(O)NH(CH$_2$)$_b$C(O)NHPG$^3$, —(CH$_2$)$_a$—CO$_2$NHPG$^3$, —C$_1$-C$_8$ straight chain alkyl, —C$_1$-C$_8$ branched alkyl, —C$_2$-C$_8$ alkenyl, —C$_2$-C$_8$ alkynyl, —(C$_1$-C$_6$ alkyl)-O—(C$_1$-C$_6$ alkyl) each of which is optionally substituted by a halogen, ether, vinyl group, allylic group, —NH$_2$, or —CN, —(CH$_2$)$_a$NR$^{88}$R$^{89}$, —(CH$_2$)$_a$—C(O)NR$^{88}$R$^{89}$, an aromatic group, heteroaromatic group, C$_3$-C$_7$ cycloalkyl, a three to twelve membered heterocyclic having up to 3 heteroatoms each of which preceding cyclic group is optionally substituted from 1 to 3 substituents independently selected from a halogen, —C$_1$-C$_6$ alkyl, —C$_2$-C$_6$ alkenyl, —O(C$_1$-C$_6$ alkyl), —C(O)—, —OH, —NH$_2$, —CN, and —C$_1$-C$_3$ perfluoro alkyl;

R$^{88}$ and R$^{89}$ are independently selected from the group consisting of —H, —O(C$_1$-C$_6$ alkyl), —C$_1$-C$_8$ straight chain alkyl, —C$_1$-C$_8$ branched alkyl, —C$_2$-C$_8$ alkenyl, —C$_2$-C$_8$ alkynyl, —(C$_1$-C$_6$ alkyl)-O—(C$_1$-C$_6$ alkyl);

Y is selected from a covalent bond, —O—, —NH—, and —C$_1$-C$_6$ alkyl;

X is selected from the group consisting of Cl, Br, I, F;

PG$^3$ is any photolabile protecting group;

a is independently any integer between 0 and 6;

b is independently any integer between 0 and 6.

In an embodiment of the invention, PG$^3$ is any photolabile protecting group known to one of skill in the art. Mention is made of T. W. Greene & P. G. M. Wuts *Protective Groups in Organic Synthesis* (4th edition) J. Wiley & Sons (2006); P. J. Kocienski *Protecting Groups* Georg Thieme Verlag (1994); and C. G. Bochet "Photolabile Protecting Groups and Linkers" *J. Chem. Soc., Perkin Trans.* 1, 2002, 125-142; herein incorporated by reference. Embodiments of photolabile protecting groups include, but are not limited to:

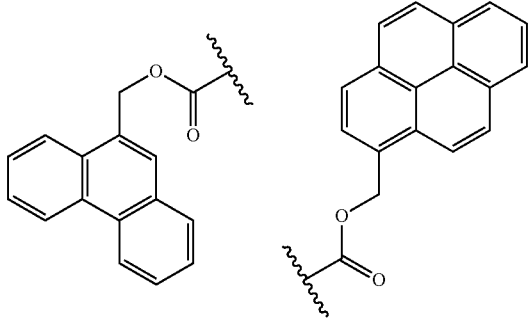

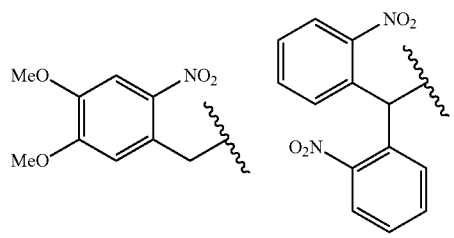

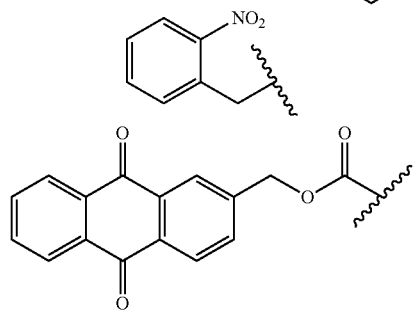

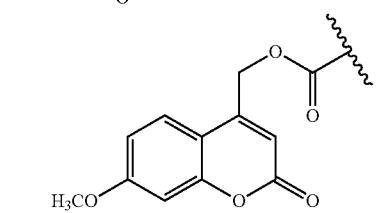

In another aspect, the invention provides a cell functionalizing probe comprises a compound of Formula III or a compound of Formula IV:

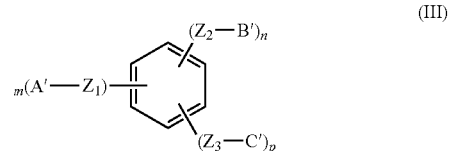

(III)

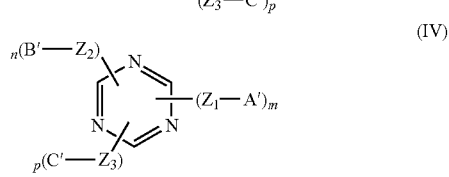

(IV)

wherein A' comprises a benzophenone, an azide, or a diazirine;

B' comprises a fluorophore, a peptide based-tag, a biotin, an affinity reagent, a hapten, one or more lanthanide heavy metal(s), or an oligonucleotide;

C' comprises an alkyne, a strained alkyne, an alkene, or a strained alkene;

Z$_1$, Z$_2$, and Z$_3$ are each independently —CH$_2$—, —O—, —S—, or —N—; and m is an integer from 1 or 2;

n is an integer from 0, 1, or 2; and p is an integer from 1 or 2, wherein m+n+p is less than or equal to 6.

In another aspect, the invention provides a cell functionalizing probe comprises a compound of Formula III or a compound of Formula IV, wherein n is 0 or 1.

In another aspect, the invention provides a cell functionalizing probe comprises a compound of Formula III or a compound of Formula IV, wherein n is 1, m is 1, and p is 1.

In another aspect, the invention provides a cell functionalizing probe comprises a compound of Formula III or a compound of Formula IV, wherein n is 0, and Z$_1$-A' and Z$_3$—C' are para to each other.

In another aspect, the invention provides a cell functionalizing probe comprises a compound of Formula III or a compound of Formula IV, wherein n is 0, and Z$_1$-A' and Z$_3$—C' are meta to each other.

In another aspect, the invention provides a cell functionalizing probe comprises a compound of Formula III or a compound of Formula IV, wherein A' comprises a diazirine.

In another aspect, the invention provides a cell functionalizing probe comprises a compound of Formula III or a compound of Formula IV, wherein A' comprises a benzophenone.

In another aspect, the invention provides a cell functionalizing probe comprises a compound of Formula III or a compound of Formula IV, wherein A' comprises an azide.

In another aspect, the invention provides a cell functionalizing probe comprises a compound of Formula III or a compound of Formula IV, wherein B' comprises a biotin.

In an embodiment, the invention provides a cell functionalizing probe comprises a compound of Formula III or a compound of Formula IV, wherein B' comprises a fluorophore.

In an embodiment, the invention provides a cell functionalizing probe comprises a compound of Formula III or a compound of Formula IV, wherein B' comprises a oligonucleotide.

In another aspect, the invention provides a cell functionalizing probe comprises a compound of Formula III or a compound of Formula IV, wherein B' is a compound of Formula II.

In another aspect, the invention provides a cell functionalizing probe comprises a compound of Formula III or a compound of Formula IV, wherein C' comprises a strained alkyne.

In another aspect, the invention provides a cell functionalizing probe comprises a compound of Formula III or a compound of Formula IV, wherein C' comprises a strained alkene.

In another aspect, the invention provides a cell functionalizing probe comprises a compound of Formula III or a compound of Formula IV, wherein A' is

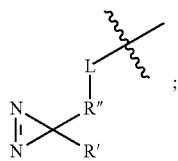

B' is —H or

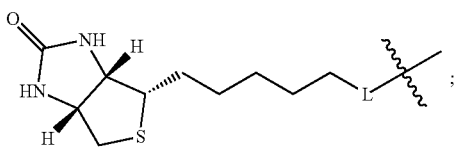

C' is

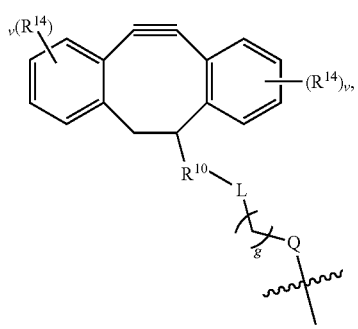

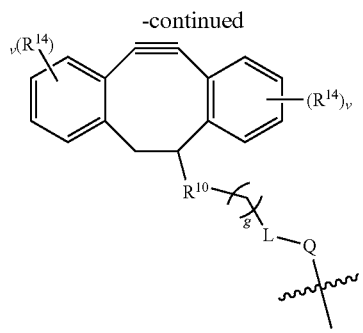

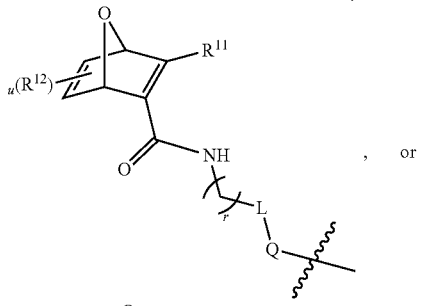

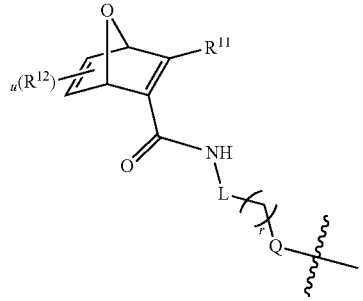

L is a linker comprising $(CH_2CH_2O)_d$, and d is an integer from 0 to 50;

g is an integer from 0, 1, 2 or 3;

R' is —H, —X, $CH_3$, or $CX_3$, wherein X is —F, —Cl, —Br, or —I;

R" is aryl or $C_{1-3}$alkylaryl; and $R^{10}$ is —$CO(CH_2)_iNHCO$—, wherein i is an integer from 0, 1, 2, 3, or 4;

$R^{11}$ is —H, $C_{1-3}$alkyl, optionally substituted with halogen;

$R^{12}$ is each independently a hydrogen, alkyl, —OH, alkoxy, amino, ester, —O-L-$R^{13}$;

$R^{13}$ is an alkyl, hydroxyl, alkoxy, amino;

$R^{14}$ is each independently —H, —OH, alkoxy, —COOH, —$COC_{1-3}$alkyl, —COH, amino, and L-O—$R^{15}$;

$R^{15}$ is —H or alkyl;

$Z_1$, $Z_2$, and $Z_3$ are each independently —$CH_2$—, —O—, —S—, or —N—;

Q is a heteroatom, such as —NH—, —O—, or —S—;

m is an integer from 1 or 2;

n is an integer from 0, 1, or 2;

p is an integer from 1 or 2, wherein m+n+p is less than or equal to 6;

r is an integer from 0, 1, 2, or 3;

u is an integer from 0, 1, 2, 3, or 4; and v is an integer from 0, 1, 2, 3, or 4.

In an embodiment, the invention provides a cell functionalizing probe comprises a compound of Formula III or a compound of Formula IV, wherein d is an integer from 0 to 50, preferably from 0 to 30.

In an embodiment, the invention provides a cell functionalizing probe comprises a compound of Formula III or a compound of Formula IV, wherein $R^{14}$ comprises a hydrophilic functional group.

In an embodiment, the invention provides a cell functionalizing probe comprises a compound of Formula III or a compound of Formula IV, wherein d is an integer from 0 to 15, preferably from 0 to 10, more preferably from 3 to 6.

In another aspect, the invention provides a cell functionalizing probe comprises a compound of Formula III or a compound of Formula IV, wherein C' is a compound of Formula I.

In another aspect, the invention provides a cell functionalizing probe comprises a compound of Formula III or a compound of Formula IV, wherein Q is a heteroatom, preferably —NH—.

In another aspect, the invention provides a cell functionalizing probe comprises a compound of Formula IIIa, a compound of Formula IIIb, a compound of Formula IIIc, a compound of Formula IIId, a compound of Formula IVa, a compound of Formula IVb, a compound of Formula IVc, or a compound of Formula IVd:

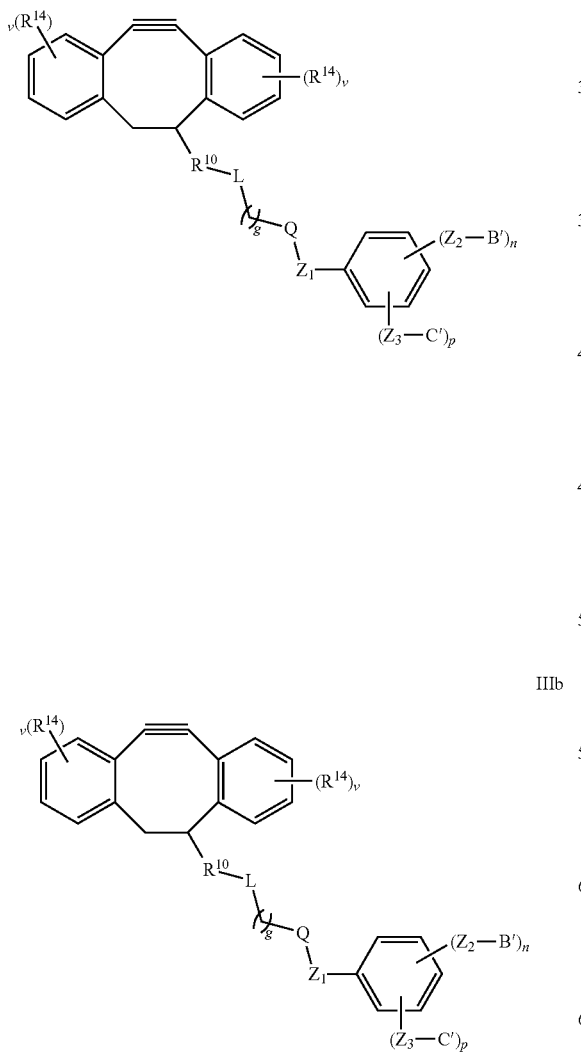

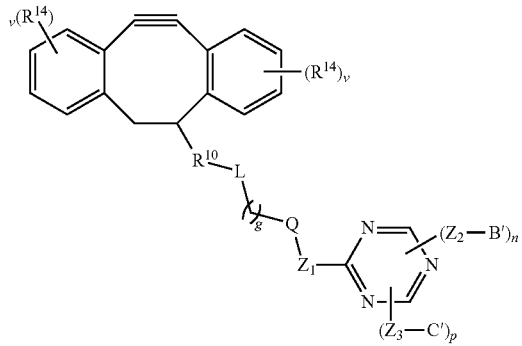

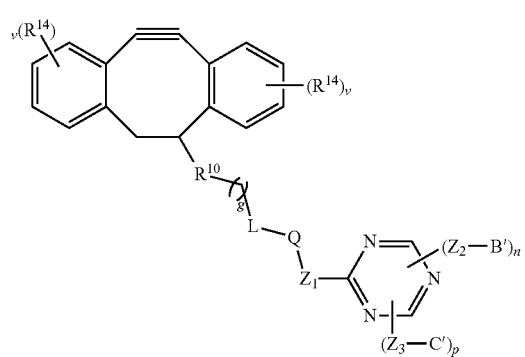

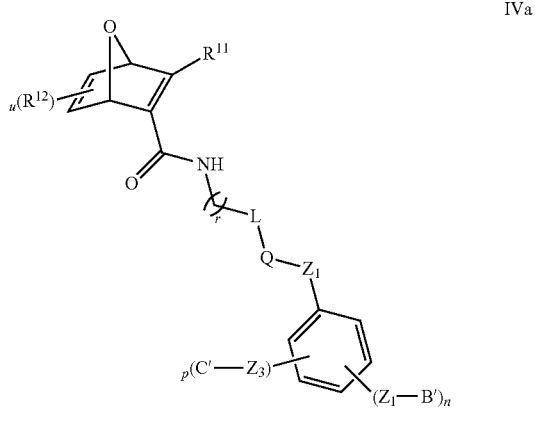

-continued

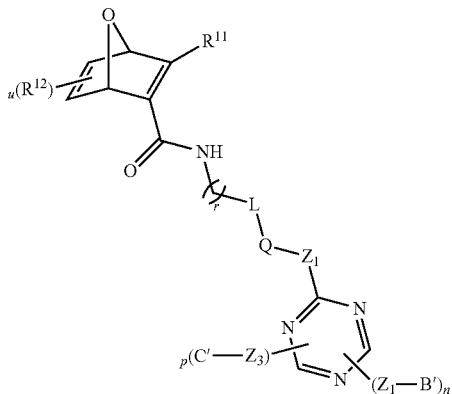

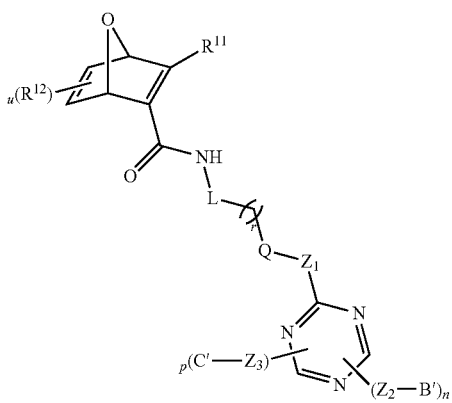

wherein:

A' is

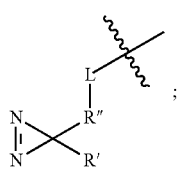

B' is —H or

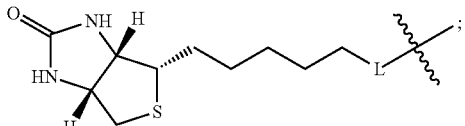
IVc

L is a linker comprising $(CH_2CH_2O)_d$, and d is an integer from 0 to 50;

g is an integer from 0, 1, 2 or 3;

R' is —H, —X, $CH_3$, or $CX_3$, wherein X is —F, —Cl, —Br, or —I;

R" is aryl or $C_{1-3}$alkylaryl; and $R^{10}$ is —$CO(CH_2)_iNHCO$—, wherein i is an integer from 0, 1, 2, 3, or 4;

$R^{11}$ is —H, $C_{1-3}$alkyl, optionally substituted with halogen;

$R^{12}$ is each independently a hydrogen, alkyl, —OH, alkoxy, amino, ester, —O-L-$R^{13}$;

$R^{13}$ is an alkyl, hydroxyl, alkoxy, amino, or ester;

$R^{14}$ is each independently —H, —OH, alkoxy, —COOH, —$COC_{1-3}$alkyl, —COH, amino, and L-O—$R^{15}$;

$R^{15}$ is —H or alkyl;

$Z_1$, $Z_2$, and $Z_3$ are each independently —$CH_2$—, —O—, —S—, or —N—;

Q is —NH—, —O—, or —S—;

m is an integer from 1 or 2;

n is an integer from 0, 1, or 2;

p is an integer from 1 or 2, wherein m+n+p is less than or equal to 6;

r is an integer from 0, 1, 2, or 3;

u is an integer from 0, 1, 2, 3, or 4; and v is an integer from 0, 1, 2, 3, or 4.

In an embodiment, the invention provides a cell functionalizing probe comprises a compound of Formulae IIIa, IIIb, IIIc, IIId, IVa, IVb, IVc, or IVd, wherein d is an integer from 0 to 50, preferably from 0 to 30, more preferably from 0 to 15, from 0 to 10, or from 3 to 6.

In an embodiment, the invention provides a cell functionalizing probe comprises a compound of Formulae IIIa, IIIb, IIIc, IIId, IVa, IVb, IVc, or IVd, wherein n is 0 or 1.

In an embodiment, the invention provides a cell functionalizing probe comprises a compound of Formulae IIIa, IIIb, IIIc, IIId, IVa, IVb, IVc, or IVd, wherein Q is a heteroatom, preferably —NH—.

In an embodiment, the invention provides a cell functionalizing probe comprises a compound of Formulae IIIa, IIIb, IIIc, IIId, IVa, IVb, IVc, or IVd, wherein $R^{14}$ comprises a hydrophilic functional group, e.g., —OH, PEG, —CO—, —NH—.

In an embodiment, the invention provides a cell functionalizing probe comprises a compound of Formulae IIIa, IIIb, IIIc, IIId, IVa, IVb, IVc, or IVd, wherein R' is —$CF_3$.

In another aspect, the invention provides a cell functionalizing probe that is

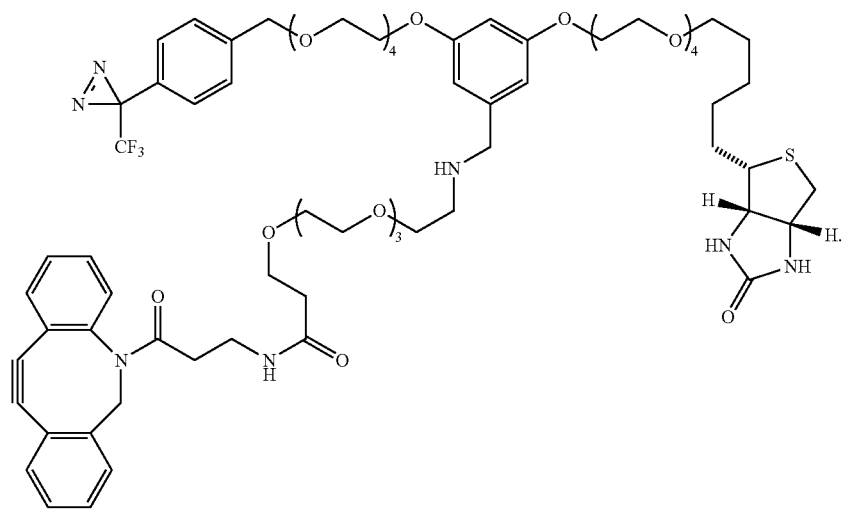

In another aspect, the invention provides a cell functionalizing probe that is

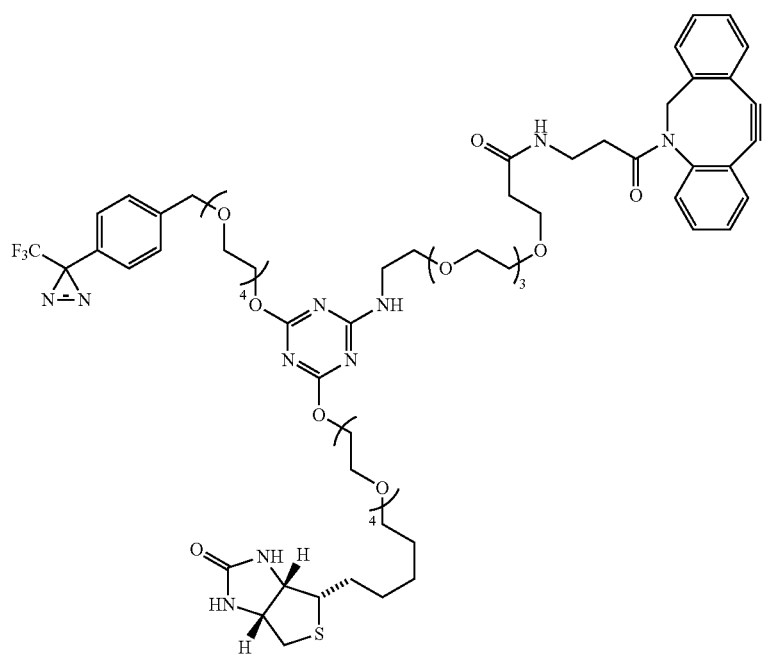

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkene" or "alkenyl" refers to an alkyl group having one or more double carbon-carbon bonds.

As used herein, "strained alkene" refers to a ring structure having one or more carbon-carbon double bonds.

As used herein, "alkyne" or "alkynyl" refers to an alkyl group having one or more triple carbon-carbon bonds.

As used herein, "strained alkyne" refers to a ring structure having one or more carbon-carbon triple bonds.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "aralkyl" refers to an alkyl group substituted by an aryl group.

As used herein, a bond substitution coming out of a ring, e.g.,

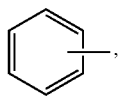

means that the substitution can be at any of the available position on the ring.

The cell functionalizing probe or cell functionalizing barcoded tag of the invention can be asymmetric (e.g., having one or more stereocenters). The description of a probe or tag without specifying its stereochemistry is intended to capture mixtures of stereoisomers as well as each of the individual stereoisomer encompassed within the genus.

As used herein, "affinity reagent" is an antibody, peptide, nucleic acid, or other small molecule that specifically binds to a larger target molecule in order to identify, track, capture, or influence its activity.

As used herein, "space barcode" and "spatial barcode" are used interchangeably.

As used herein, "cell functionalizing barcoded tag" or "oligo tag" or "barcoded tag" are used interchangeably.

It is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

The invention comprehends a method to develop and leverage a novel platform for spatially-resolved single cell genomic profiling of tissues to identify novel immune evasion genes from intratumoral heterogeneity. This method provides an integrated, single platform to measure changes in gene expression directly from single cells. The connection between cells and their neighbors is lost when averaging across a population (e.g., a large surface of cells) or disaggregating tissues for scRNA-Seq. The present application provides a spatially-resolved scRNA-Seq approach to link neighboring cell states/phenotypes and use it to propose regulators of intracellular circuits, which be validated and screened for clinical relevance.

Figure 1:
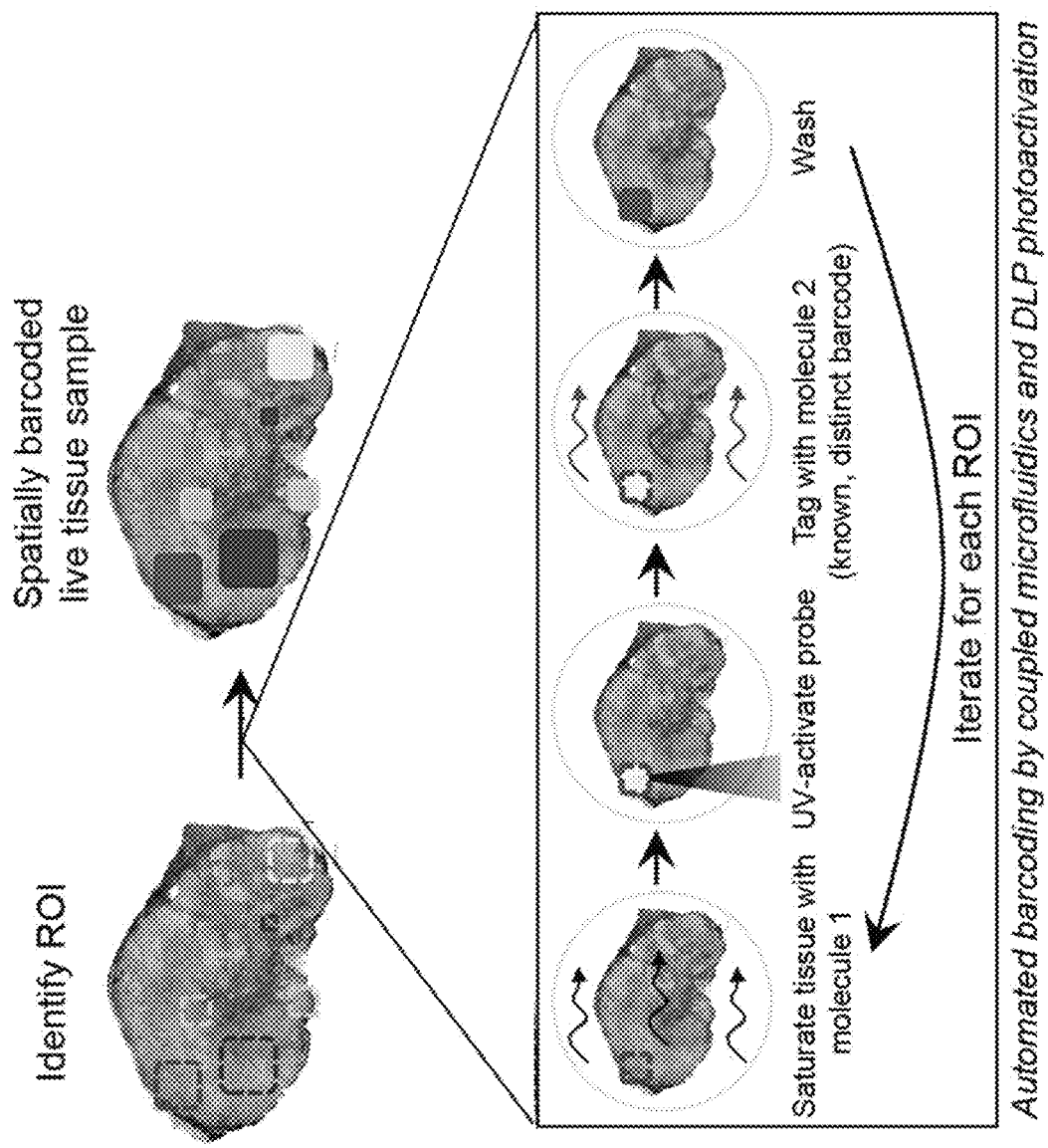
FIG. 1 illustrates a method to optically tag cells within microscopic sub-regions of a cellular ensemble prior to scRNA-Seq.
Figure 2:
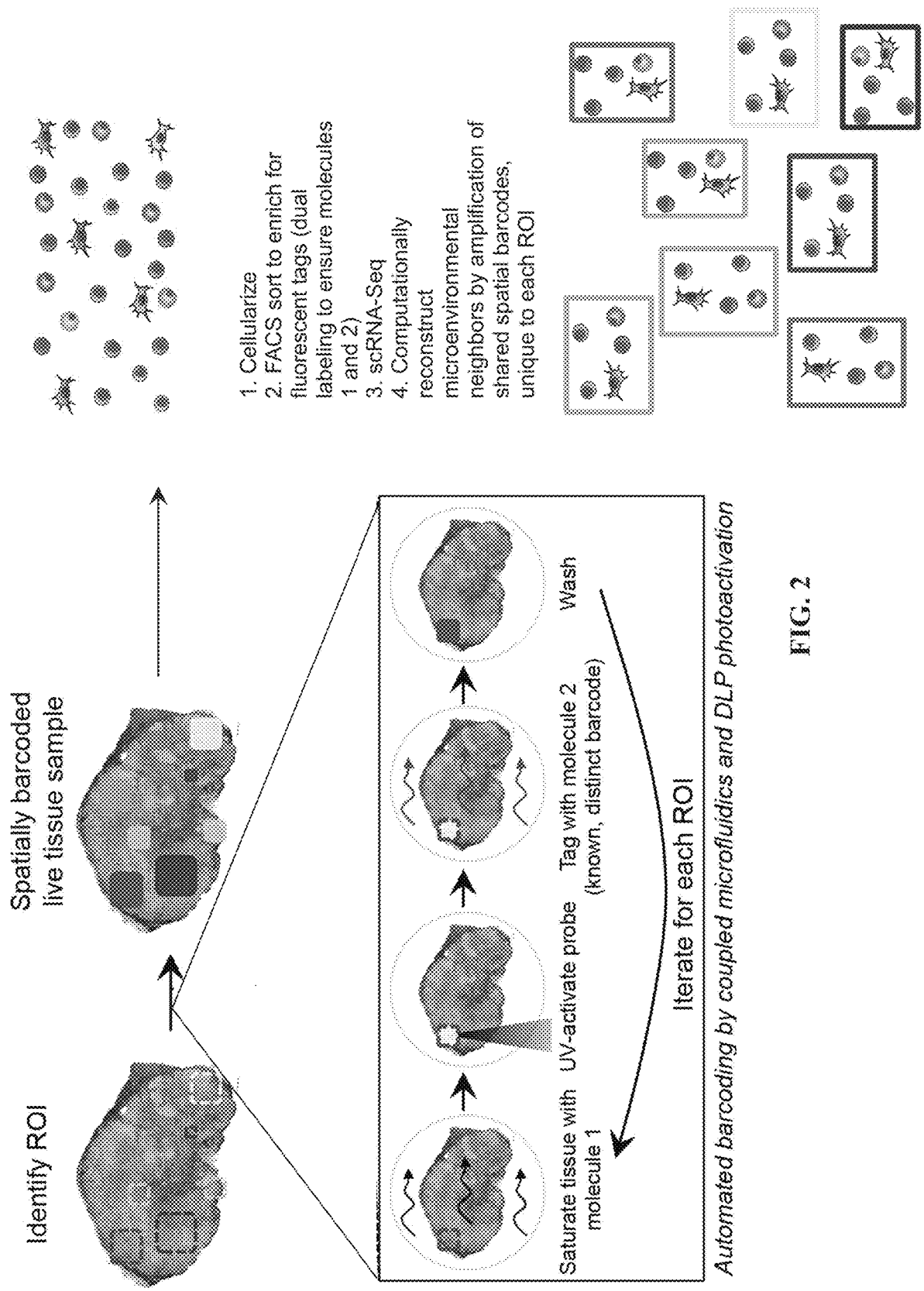
FIG. 2 illustrates to optically tag cells within a region of interest in order to spatially barcode live tissue samples. Once the cells have been tagged, the sample is cellularized, sorted to enrich for fluorescent tags, since cell sequences are profiled, and reconstruct microenvironmental neighbors by amplification of shared spatial barcodes, which are unique to each region of interest by a computational method.
Figure 3:
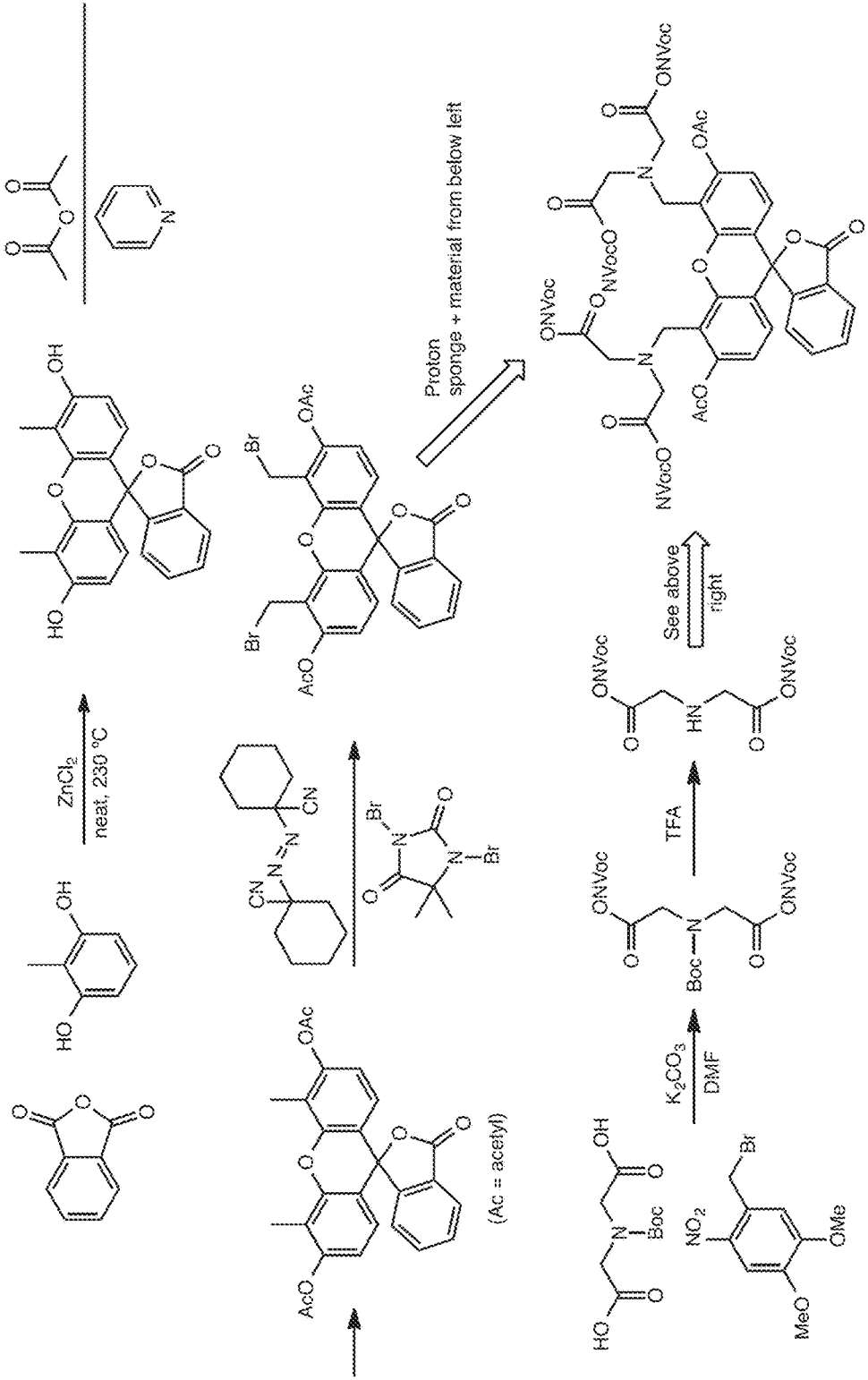
FIG. 3 illustrates a scheme for the synthesis of a photocaged fluorescein molecule.
Figure 4:
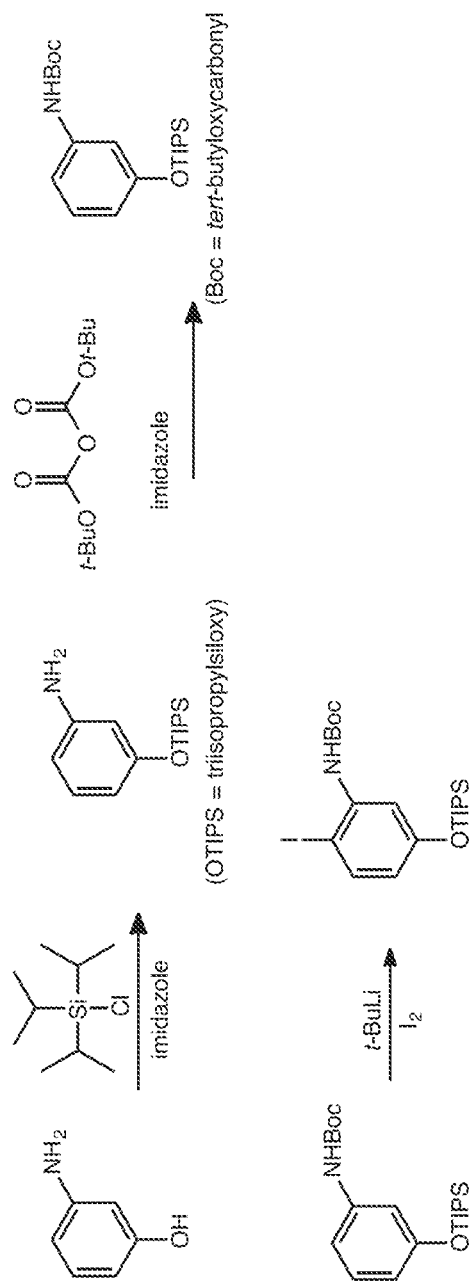
FIG. 4 illustrates a scheme for the synthesis of the two fragments, an iodobenzene and ethynylbenzene, towards the synthesis of a strained alkene.
Figure 4:
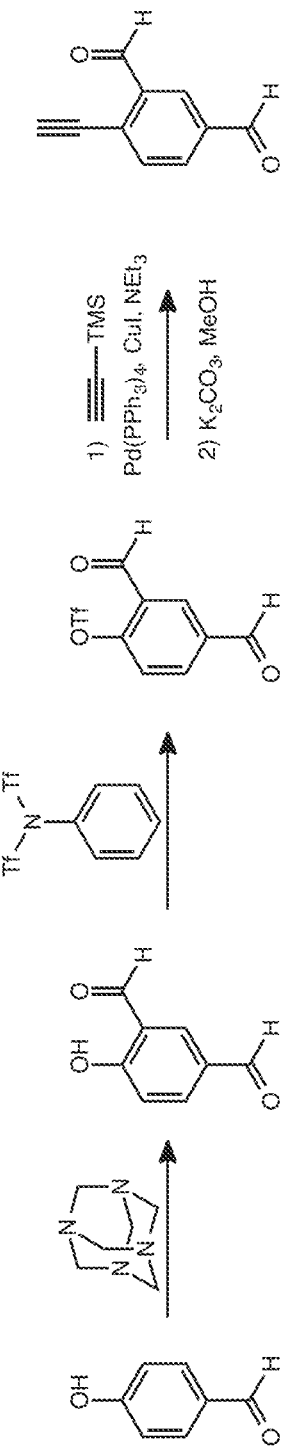
Figure 5:
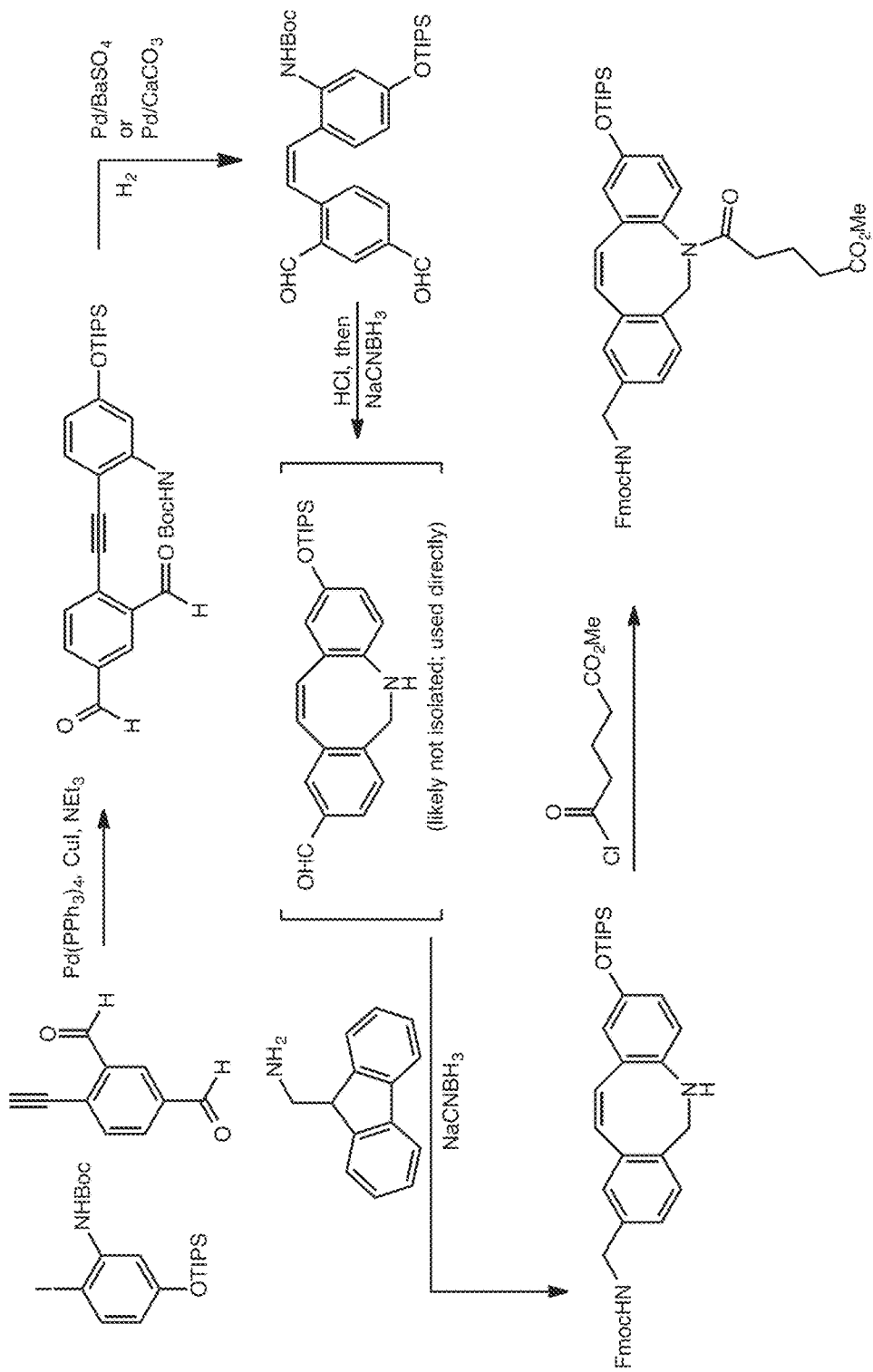
FIG. 5 illustrates the coupling steps with both fragments to afford a strained alkene.
Figure 6:
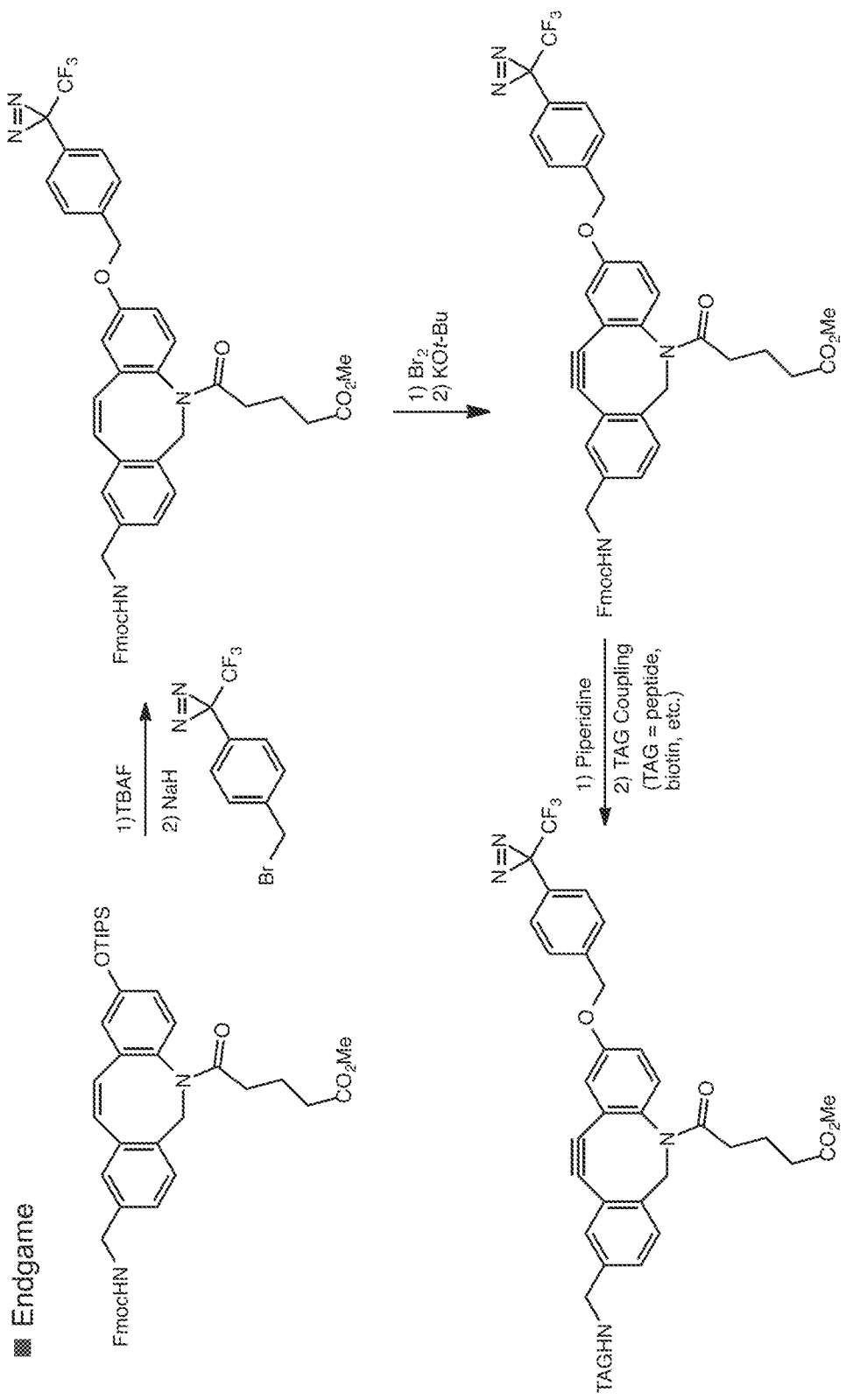
FIG. 6 illustrates the scheme for the synthesis of the cell functionalizing tissue probe.
Figure 7:
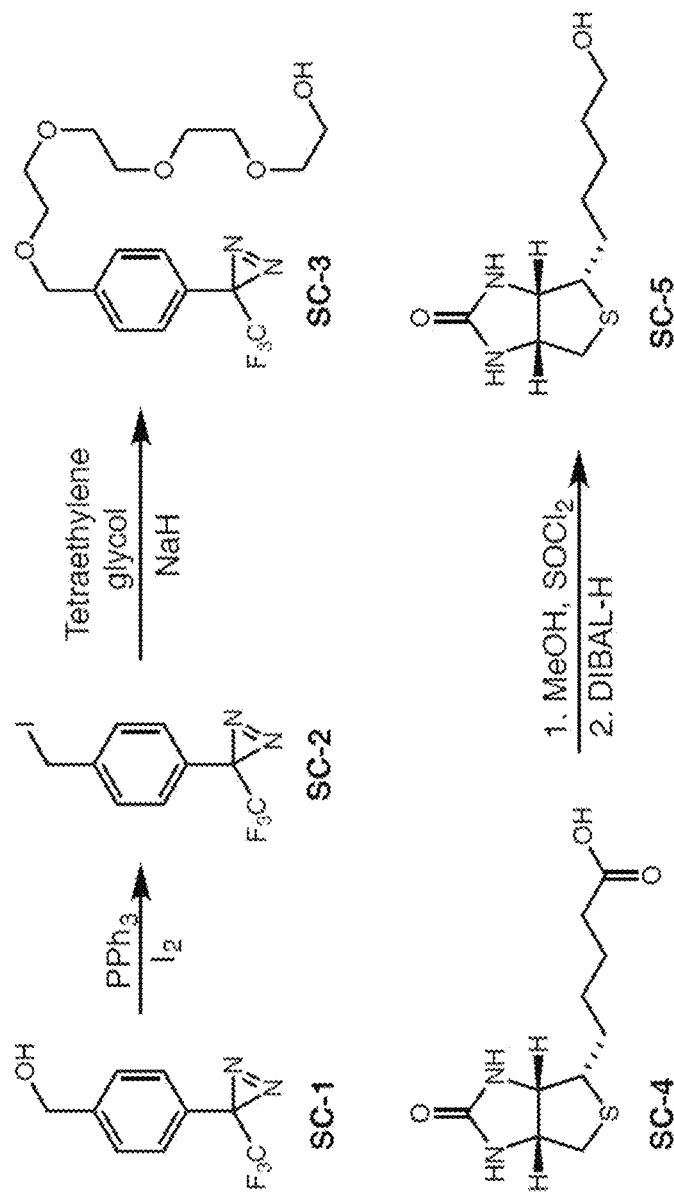
FIG. 7 illustrates a scheme for the synthesis of a thienoimidazolone (SC-5), and SC-3, component/fragment of the target molecule. The SC-3 reaction is initiated with SC-1 PPh3 and I2 to form intermediate SC-2 that is further reacted with tetraethylene glycol and NaH to form component/fragment SC-3. SC-4 is reacted to form component/fragment SC-5.
Figure 8:
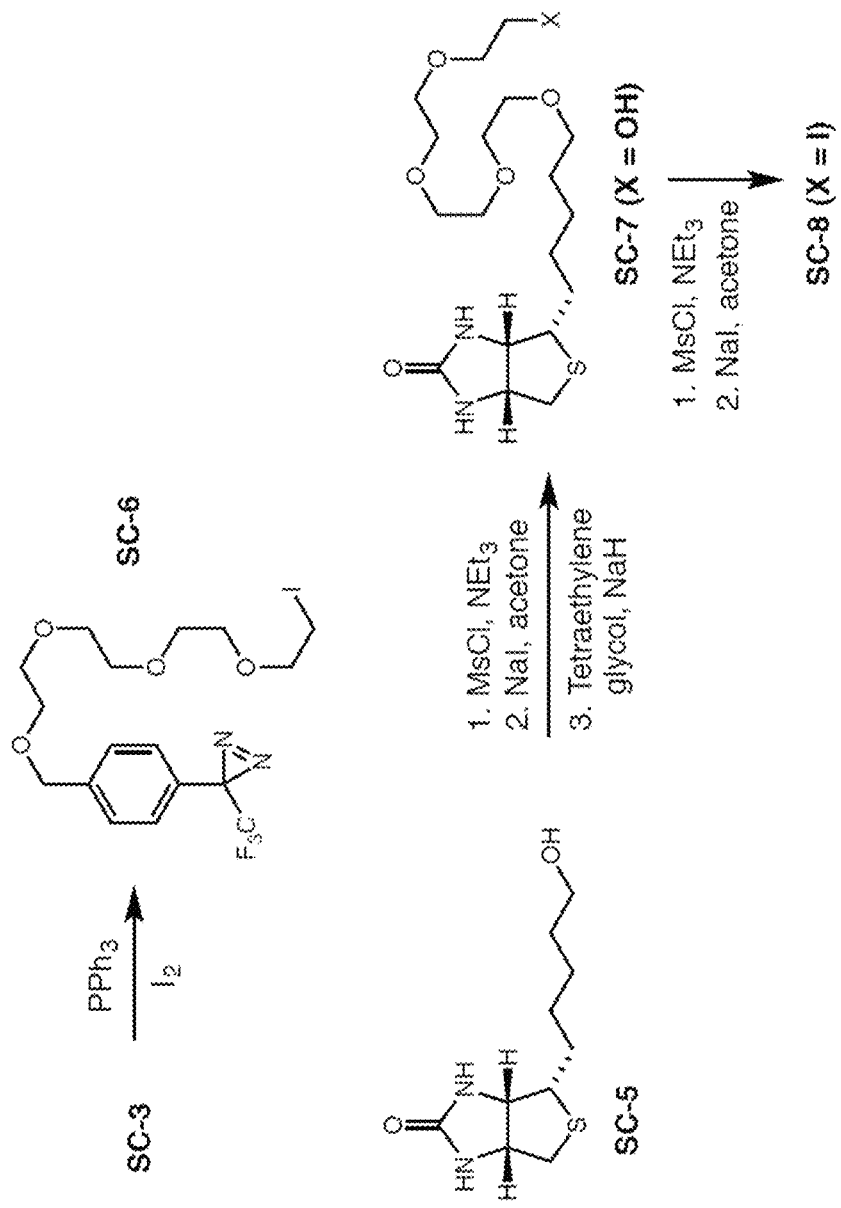
FIG. 8 illustrates a scheme for the synthesis of a tetraethylene glycol derivatives of a thienoimidazolone, SC-7 and SC-8, as well as the synthesis of (SC-6) component/fragment of the target molecule. The SC-6 is synthesized from the reaction of SC-3, PPh3 and I2. The SC-8 reaction is initiated first with SC-5, MsCl, and NET$_3$ followed by NaI and acetone then tetraethylene glycol and NaH to form product SC-7. A reaction of first SC-7, MsCl, and Net$_3$ followed by NaI and acetone to arrive at SC-8.
Figure 9:
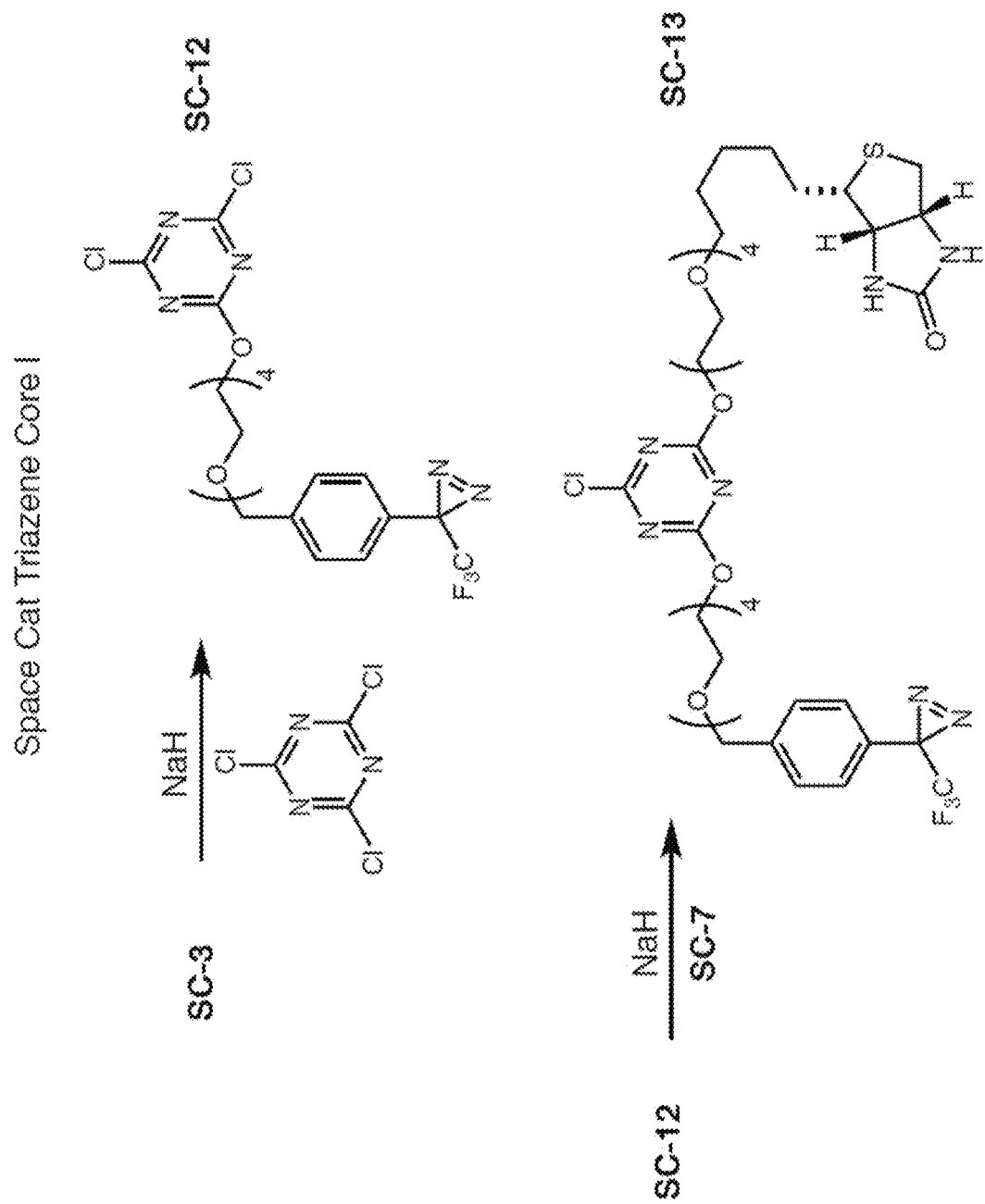
FIG. 9 illustrates a scheme for the synthesis of "SpaceCat" with a triazene core (SC-12 and SC-13). The assembly of SpaceCat begins with the reaction of the component/fragment SC-3, NaH, and the triazene core to form SC-12. The partiality assembled "SpaceCat" SC-12 is reacted with NaH and the component/fragment SC-7 to form SC-13.
Figure 10:
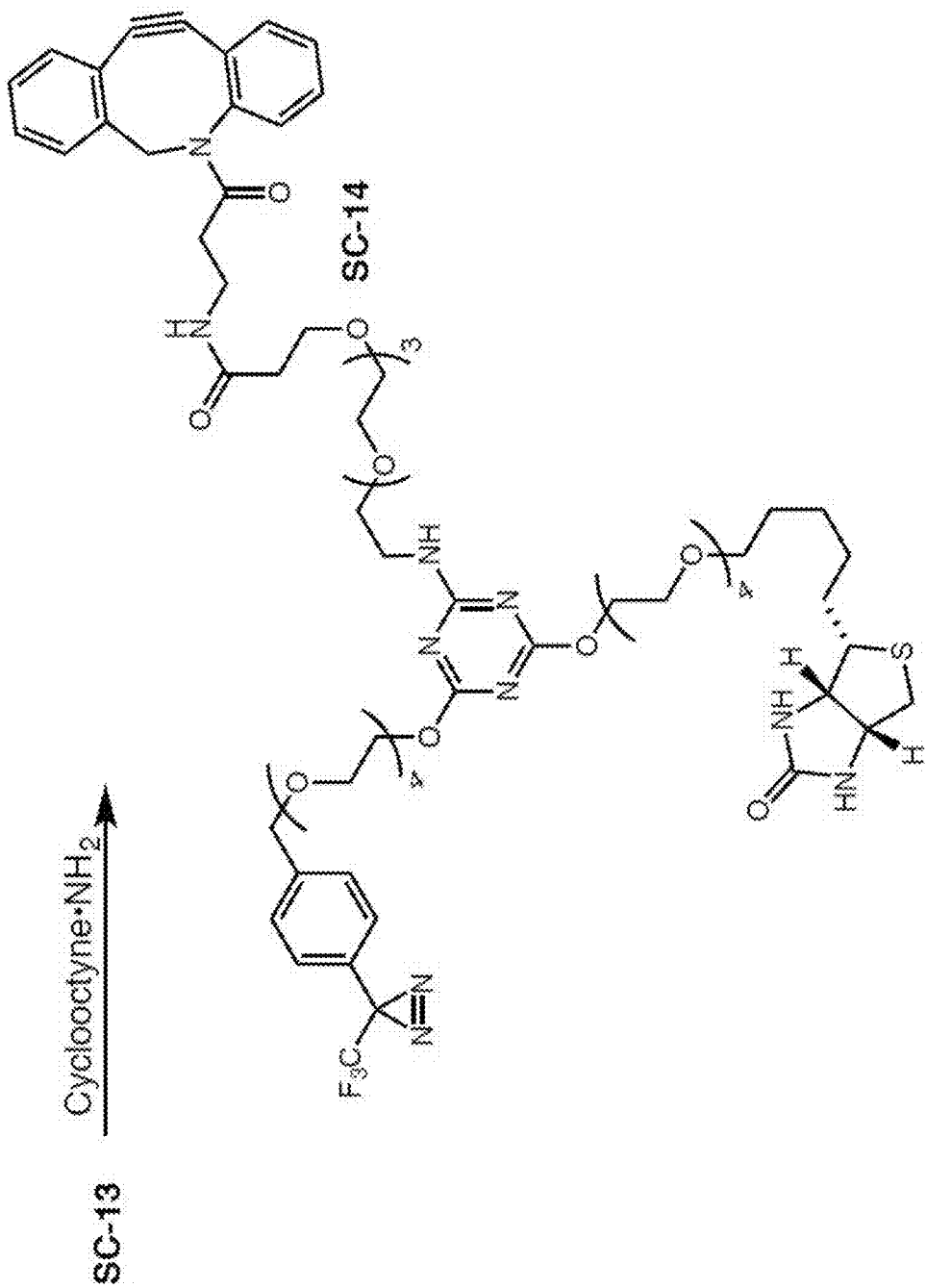
FIG. 10 illustrates the derivatization of the triazene core with a cyclooctyne, a thienoimidazolone, and a diazirine (SC-14).
Figure 11:
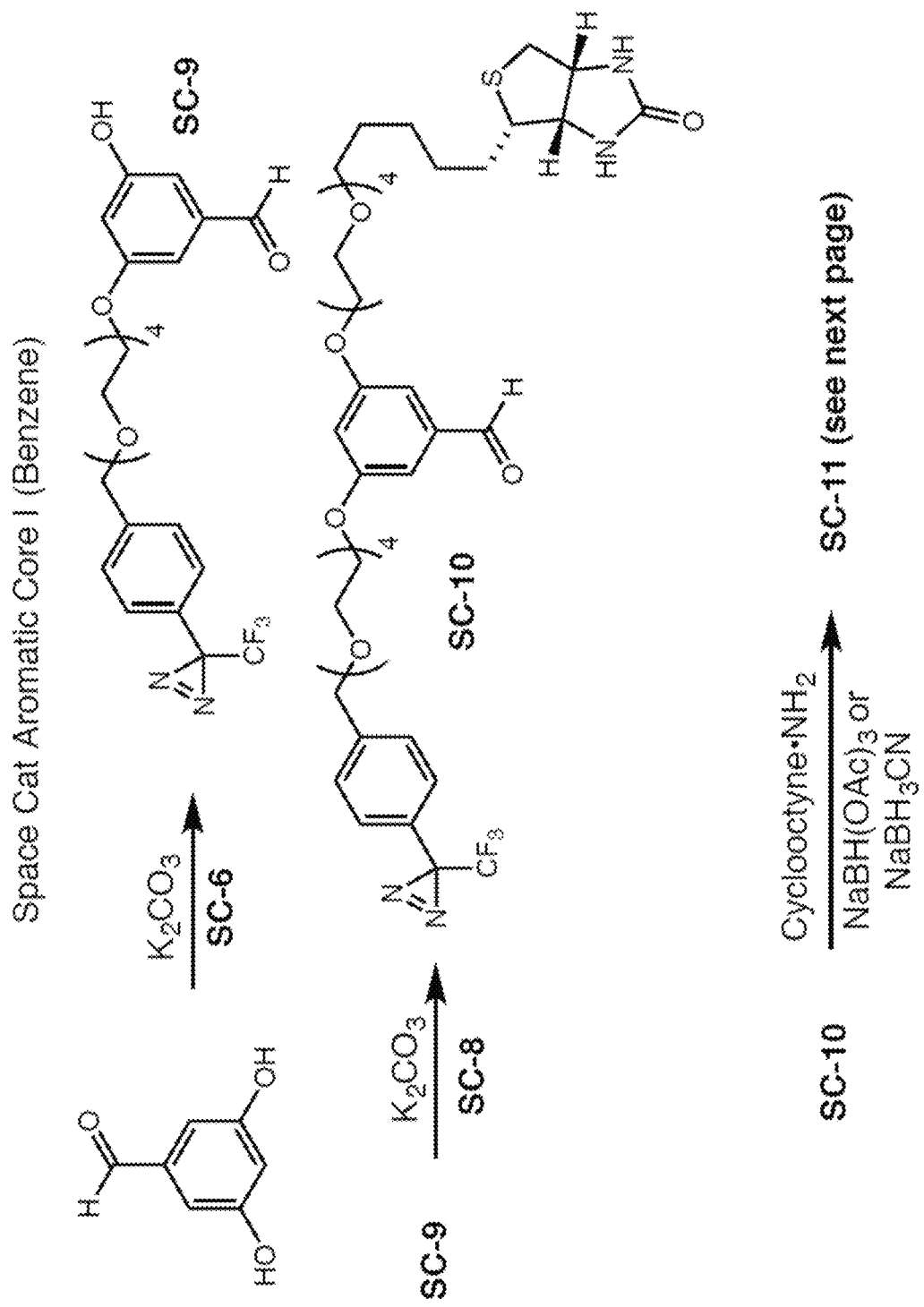
FIG. 11 illustrates a scheme for the synthesis of "SpaceCat" with an aromatic core (SC-11). First, 3,5-Dihydroxybenzaldehyde is reacted with K$_2$CO$_3$ and SC-6 to form SC-9. Partially assembled "SpaceCat" SC-10 is synthesized from the reaction of SC-9 with K$_2$CO$_3$ and SC-8. The final target compound with an aromatic core (SC-11) is synthesized from the reaction of SC-10, cyclooctyne.NH$_2$, NaBH(OAc)$_3$ and NaBH$_3$CN.
Figure 12:
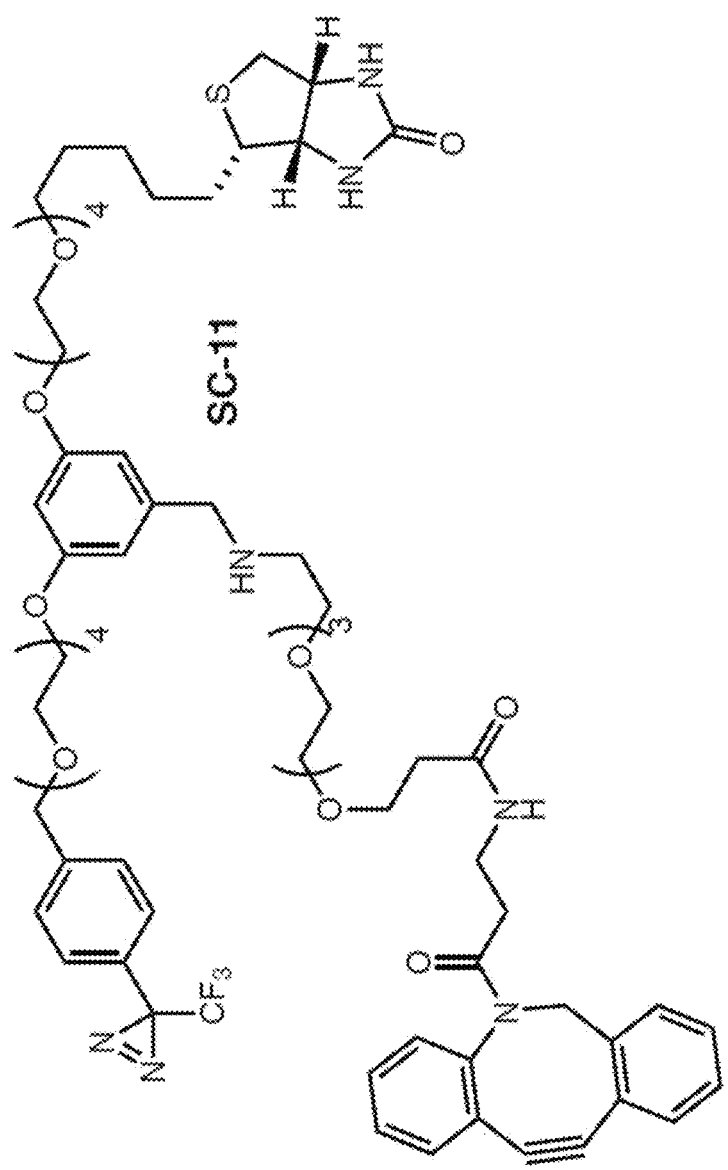
FIG. 12 illustrates the final target compound with an aromatic core (SC-11).

Applicants developed a platform for optically tagging cells within microscopic sub-regions of a cellular ensemble (e.g., a tissue slide from a tumor) prior to population-level RNA-Seq (or genomic, proteomic, lipidomic or other analyte profiling) or scRNA-Seq (or single-cell 'omic profiling), overcoming current limitations on spatial resolution and/or throughput. The invention comprehends a direct, real-time imaging and labeling on live biopsy, whole tissue resections, or any imagable cellular surface or biological surface or organic surface. Applicants synthesized a biorthogonally reactive molecule as illustrated in FIG. 6 (e.g., cell functionalizing probe "CFP") which, in the present example, is photoactivated to generate a reactive intermediate. Upon optical activation, the cell functionalizing probe tags a region of interest ("ROI") in a live tissue section via, for example, rapid C—H bond insertion. After washing, a fluorescent oligonucleotide (e.g., spatial barcode oligonucleotide "SBO") or other spatial tag is covalently linked via a bioorthogonal reaction. The Smart-Seq2-compatible oligonucleotide is retained through dissociation and FACS enrichment, thus enabling the assignment of cells to their imaged ROI.

In an aspect of the invention, the platform contains an automated reagent delivery system and DLP-enabled optical control for tagging many ROIs. The platform, in some aspects, can be coupled to a microscope to allow for real-time cell visualization, and thus quantification, of additional optical variables of interest including, but not limited to, morphology, fluorescent protein or antibody levels, etc.

The invention comprehends a method applicable to any tissue or cell ensemble structure enabling one of skill in the art to answer novel biological inquiries in any system without the requirement of transfection or genetic engineering. For example, the platform profiles, in a spatially-resolved fashion, mouse Braf/Pten melanoma and MC38 colon carcinoma tumor sections. Applicants are able to identify heterogeneity in both immune cell state/behavior and number with each geographical region, and then correlate those parameters with the gene expression programs observed in tumor cells found in the same region. Further, the invention provides a method to study the functional properties of a defined (by photoactivation, during cell sorting or prior to patterning) set of cells selected from a heterogeneous population. Functional properties of a tissue or cell ensemble arise through interactions of a variety of cells where structure in its environment (e.g., extracellular matrix) provides organization for the exchange of chemical, electrical, and mechanical information between neighboring and distant cells (Todhunter, et al. *Nature Methods* 2015, vol. 12(10), 975). Thus, in an aspect of the invention, Applicants reconstruct information provided by the structure of tissue by determining the geographical region of the cells within a tissue and linking those regions to different phenotypes (e.g., immune cell behaviors.) Applicants use principle component analysis, computational methods, or any other linear or nonlinear dimensionality reduction technique and are able to identify or predict subpopulations of cells with a phenotype. The method may also "learn" or generate predictive cell-cell relationships or interactions. By measuring complex gene expression profiles at the single cell level, Applicants identify subsets of cells with expression patterns of interest that could not be detected when analyzing the "average" gene expression of the heterogeneous population. More generally, the method envisions the analysis of phenotypes of one or more cells informing the analysis of other co-localized cells, either within a specific spatial location or between spatial locations.

It is to be understood that this invention is not limited to particular methods, components, products or combinations described, as such methods, components, products and combinations may, of course, vary. It is also to be understood that the terminology used herein is not intended to be limiting, since the scope of the present invention will be limited only by the appended claims. Preferred features and embodiments of this invention are set forth herein, including by way of numbered statements. Each feature and embodiment of the invention so discussed herein may be combined with any other feature and/or embodiments unless clearly indicated to the contrary. In particular, any feature indicated as being preferred or advantageous may be combined with any other feature or features indicated as being preferred or advantageous. Aspects of the present invention include any one or any combination of one or more of the aspects, features or embodiments discussed herein, including as enumerated herein 1 to 74, with any other statement and/or embodiments. The present invention is discussed with respect to particular embodiments but the invention is not limited thereto but only by the claims. Any reference signs in the claims shall not be construed as limiting the scope. As also discussed herein, the term "comprising" does not exclude other elements or steps. The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of", "consists essentially" and "consists essentially of". "Consisting essentially of" permits inclusion of additional components not listed, provided that they do not materially affect the basic and novel properties of the invention. Singular terms, e.g., "a", "an", and "the" include both singular and plural referents unless the context clearly dictates otherwise. The recitation of numerical ranges by endpoints includes all numbers and fractions subsumed within the respective ranges, as well as the recited endpoints. The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed. Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. All references cited in the present specification are hereby incorporated by reference in their entirety. In particular, the teachings of all references herein specifically referred to are incorporated by reference. Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination. Any drawings herewith form a part of this specification, and are provided as a way of illustration only of specific embodiments in which the invention may be practiced; but, it is to be understood that other embodiments may be utilized and structural or logical changes may be made without departing from the scope of the present invention. Accordingly, the herein detailed description is not to be taken in a limiting sense, and the scope of the present invention is defined by the appended claims.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2nd ed., Cold Spring Harbor Press, Plainsview, N.Y. (1989); and Ausubel et al., Current Protocols in Molecular Biology (Supplement 47), John Wiley & Sons, New York (1999), Innis et al., PCR Protocols: A Guide to Methods and Applications, Academic Press: San Diego, 1990. General principles of microbiology are set forth, for example, in Davis, B. D. et al., Microbiology, 3rd edition, Harper & Row, publishers, Philadelphia, Pa. (1980), for definitions and terms of the art. The definitions provided herein should not be construed to have a scope less than understood by a person of ordinary skill in the art.

Unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein. Accordingly, the invention can be practiced without undue experimentation by way of the herein disclosure taken in conjunction with knowledge in the art.

The present invention provides tools and methods for the systematic analysis of genomic interactions between cells, in particular immune cell subpopulations, including higher order interactions.

The present invention provides tools and methods for combinatorial probing of cellular circuits, for dissecting cellular circuitry, for delineating molecular pathways, and/or for identifying relevant targets for therapeutics development.

The present invention in certain embodiments relates to analyzing genetic signatures of immune cells, such as molecular profiling at the single cell or cell (sub)population level, which immune cells are characterized by or characteristic of a particular immune responder phenotype.

In an aspect, the invention relates to a method of identifying an immune cell gene signature, protein signature, and/or other genetic or epigenetic signature associated with a specific immune responder phenotype or an immune cell subpopulation associated with a specific immune responder phenotype, comprising:

comparing single cell or cell population RNA and/or protein expression profiles and/or other genetic or epigenetic profiles of a biological sample of said specific immune responder phenotype with single cell or cell population RNA and/or protein expression profiles and/or other genetic or epigenetic profiles of a biological sample of a different immune responder phenotype or a different an immune cell subpopulation associated with said specific immune responder phenotype;

determining differentially expressed RNAs and/or proteins and/or other genetic or epigenetic elements;

determining an immune cell gene signature, protein signature, and/or other genetic or epigenetic signature associated with a specific immune responder phenotype or an immune cell subpopulation associated with a specific immune responder phenotype as one or more of said differentially expressed RNAs and/or proteins and/or other genetic or epigenetic elements.

Such method also in particular allows to identify particular immune cell subpopulations which are specifically associated with a particular immune responder phenotype, as well as to identify a particular immune responder phenotype, based on detection of such gene signatures, protein signature, and/or other genetic or epigenetic signature.

All methods according to various aspect and embodiments of the invention may involve analyzing gene signatures, protein signature, and/or other genetic or epigenetic signature or (immune cell) phenotypes based on single cell analyses or alternatively based on cell population analyses.

In related aspects, the invention relates to gene signatures, protein signature, and/or other genetic or epigenetic signature of immune cells associated with particular immune responder phenotypes, such as for instance particular immune cell subpopulations. The invention further relates to particular immune cell subpopulations, which may be identified based on the methods according to the invention as discussed herein; as well as methods to obtain such cell (sub)populations and screening methods to identify immunomodulators capable of inducing or suppressing particular immune cell (sub)populations, such as for instance to alter immune cell population composition. Methods as described herein allow for instance in certain aspects the specific (partial) induction or (partial) depletion of particular immune cell subpopulation, such as to alter for instance an immune responder phenotype, which may in certain embodiments be defined by particular immune cell (sub) population compositions (e.g. different immune cell subpopulations characterized by specific immune cell states).

The invention further relates to various uses of the gene signatures, protein signature, and/or other genetic or epigenetic signature as defined herein, as well as various uses of the cells or cell (sub)populations as defined herein. Particular advantageous uses include methods for identifying modulators based on the gene signatures, protein signature, and/or other genetic or epigenetic signature as defined herein. In an aspect, the invention hereto provides for a method of identifying a modulant capable of modulating, such as inducing or alternatively suppressing, a specific responder phenotype having a specific gene signature, protein signature, and/or other genetic or epigenetic signature, comprising: applying a candidate modulant to a cell or a population of cells and identifying a modulant capable of inducing or alternatively suppressing a specific responder phenotype if said specific gene signature, protein signature, and/or other genetic or epigenetic signature is induced or alternatively repressed in one or more of said cells. The invention further relates to modulators capable of modulating, such as inducing or repressing, a particular responder phenotype or a specific gene signature, protein signature, and/or other genetic or epigenetic signature, as well as their use for modulating, such as inducing or repressing, a particular responder phenotype, or a particular gene signature, protein signature, and/or other genetic or epigenetic signature. Such modulation may include for instance specific induction or alternatively specific reduction of particular cells, or cell (sub) populations.

In further related aspects, the invention relates to diagnostic (including monitoring the status of a subject), prognostic (including monitoring treatment efficacy), prophylactic, or therapeutic methods. Diagnostic or prognostic methods according to the invention in particular may comprise detecting the gene signatures, protein signature, and/or other genetic or epigenetic signature as discussed herein. Therapeutic or prophylactic methods according to the invention in particular may comprise modulating the responder phenotype, and may include modulating the gene signature, protein signature, and/or other genetic or epigenetic signature of cells or cell (sub)populations. Such methods include both in vitro as well as in vivo modulation.

As used herein, the term "gene signature" may be used interchangeably with the term "signature gene". These terms relate to one or more gene (or one or more particular splice variants thereof), the (increased) expression or activity of which or alternatively the decreased or absence of expression or activity of which is characteristic for a particular (multi)cellular phenotype, i.e. the occurrence of such particular (multi)cellular phenotype may be identified based on the presence or absence of such gene signature. The signature may thus be characteristic of a particular phenotype, but may also be characteristic of a particular immune cell subpopulation within a particular phenotype. Similarly, an "epigenetic signature" relates to one or more epigenetic element (or modification), the (increased) occurrence of which or alternatively the absence of which is characteristic for a particular (multi)cellular phenotype, i.e. the occurrence of such particular (multi)cellular phenotype may be identified based on the presence or absence of such epigenetic signature. As used herein a signature encompasses any gene or genes or epigenetic element(s) whose expression profile or whose occurrence is associated with a specific cell type, subtype, or cell state of a specific cell type or subtype within a population of cells. Increased or decreased expression or activity or prevalence may be compared between different phenotypes in order to characterize or identify specific phenotypes. A gene signature as used herein, may thus refer to any set of up- and down-regulated genes between two (multi)cellular states or phenotypes derived from a gene-expression profile. For example, a gene signature may comprise a list of genes differentially expressed in a distinction of interest; (e.g., high responders versus low responders; diseased state versus normal state; etc.). Similarly, an epigenetic signature as used herein, may thus refer to any set of induced or repressed epigenetic elements between two (multi)cellular states or phenotypes derived from an epigenetic profile. For example, an epigenetic signature may comprise a list of epigenetic elements differentially present in a distinction of interest; (e.g., high responders versus low responders; diseased state versus normal state; etc.). It is to be understood that also when referring to proteins (e.g. differentially expressed proteins), such may fall within the definition of "gene" signature, and may on certain occasions be referred to as "protein signature".

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate cell systems. The signatures of the present invention may be discovered by analysis of expression profiles of single-cells within a population of cells from isolated samples (e.g. blood samples), thus allowing the discovery of novel cell subtypes or cell states that were previously invisible or unrecognized. The presence of subtypes or cell states may be determined by subtype specific or cell state specific signatures. The presence of these specific cell (sub) types or cell states may be determined by applying the signature genes to bulk sequencing data in a sample. Not being bound by a theory, the signatures of the present invention may be microenvironment specific, such as their expression in a particular spatio-temporal context. Not being bound by a theory, signatures as discussed herein are specific to a particular pathological context (e.g. infection, cancer, autoimmune disease, allergy). Not being bound by a theory, a combination of cells having a particular signature may indicate an outcome. Not being bound by a theory, a spatial pattern can be used to deconvolute the network of cells present in a particular condition (healthy or pathological). Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states that occur in a subpopulation of cells that are linked to particular pathological condition, or linked to a particular outcome or progression of a pathological condition, or linked to a particular response to treatment of a pathological condition.

The signature according to certain embodiments of the present invention may comprise or consist of one or more genes, proteins and/or epigenetic elements, such as for instance 1, 2, 3, 4, 5, 6, 7, 8, 9, 10 or more. It is to be understood that a signature according to the invention may for instance also include genes or proteins as well as epigenetic elements combined.

In certain embodiments, a signature is characterized as being specific for a particular responder phenotype or specific for a particular cell or cell (sub)population if it is only present, detected or detectable in that particular responder phenotype or specific for a particular cell or cell (sub) population. In this context, a signature consists of one or more differentially expressed genes/proteins or differential epigenetic elements when comparing different immune responder phenotypes or different immune cells or immune cell (sub)populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

In one embodiment, the cells are detected by immunofluorescence, by mass cytometry (CyTOF), FACS, atac-seq, in situ hybridization, etc. Other methods including absorbance assays and colorimetric assays are known in the art and may be used herein.

When referring to induction, or alternatively suppression of a particular signature, preferable is meant induction or alternatively suppression (or upregulation or downregulation) of at least one gene/protein and/or epigenetic element of the signature, such as for instance at least to, at least three, at least four, at least five, at least six, or all genes/proteins and/or epigenetic elements of the signature.

Signatures may be functionally validated as being uniquely associated with a particular phenotype, such as a giving a preferred response ("responder phenotype"). Induction or suppression of a particular signature may consequentially associated with or causally drive a particular responder phenotype.

As used herein, the term "responder phenotype" may be used interchangeably with "response phenotype". These terms refer to an individual characterized by a specific immune response towards a pathological insult. By extension, these terms also refer to organs, tissues, cells, or cell (sub)populations of such individuals, including immune cells. By means of example, a specific response may constitute an improved or vigorous immune response or alternatively a poor immune response; a fast immune response or alternatively a slow immune response; an immune response characterized by for instance a specific cytokine profile or a specific sequence of succession of cytokine expression; etc. without limitation, for instance in the context of viral infection.

As used herein, the term "immune responder phenotype" may be used interchangeably with "immune response phenotype". These terms refer to an individual characterized by a specific immune response towards a pathological insult, or by a particular immunological state. By extension, these terms also refer to organs, tissues, cells, or cell (sub) populations of such individuals, including immune cells. By means of example, a specific immune response may constitute an improved or vigorous immune response or alternatively a poor immune response; a fast immune response or alternatively a slow immune response; an immune response characterized by for instance a specific cytokine profile or a specific sequence of succession of cytokine expression; etc. without limitation, for instance in the context of viral infection, such as for instance HIV infection, the immune responder phenotype may be an elite controller. Elite controller is a term applied to the rare group of HIV-positive individuals who maintain substantially undetectable viral loads in the absence of any treatment. Although genetic variability in the HLA locus and enhanced CD8 T cell immunity have been proposed to be some of the causes of the spontaneous immunological control of HIV-1 in this cohort, cellular and molecular mechanisms responsible for the elite controller phenotype are not fully understood. An elite controller may for instance be defined as having consecutive undetectable HIV-RNA measurements for more than six months or otherwise with at least 90% of measurements having less than 400 copies/ml over at least 10 years. Other immune responder phenotypes for instance include long term non progressors (LTNP), slow progressors, HIV controllers (HICs), viremic controllers, noncontrollers, and rapid progressors. A progressive controller has roughly about 100 copies of HIV while a viremic controller has full blown AIDS and declining health. Without wishing to be bound by any one particular theory, it is believed that someone who is a viremic controller was formerly an elite or progressive controller. The present invention thus relates to examining signatures for an elite controller, a progressive controller and a viremic individual. For a viremic controller and potentially a progressive controller, in certain embodiments it is desirable to modify the signatures of that individual by modulating, such as perturbing the system such that the signature resembles that of an elite controller. Other immune responder phenotypes for instance include phenotypes based on neutralizing antibody breadth, such as a phenotype characterized by broadly neutralizing antibodies. Broadly neutralizing antibodies are neutralizing antibodies (Nab), which are antibodies which defend a cell from an antigen or infectious body by inhibiting or neutralizing any effect it has biologically. Broadly neutralizing antibodies are neutralizing antibodies which for instance are capable of neutralizing multiple disease strains, such as multiple HIV strains.

As used herein "co-occurant" may be used to indicate the temporal property of two things happening at the same time; events belonging at the same time, or being observed at the same time.

In certain embodiments, the immune responder phenotype is characteristic of, associated with, or correlated with a particular (immune) response to a pathological condition.

A "pathological condition" as referred to herein includes any physiologically abnormal condition of an organism, which results in damage of or harm to the organism. A pathological condition as referred to herein is in particular associated with or causally related to an immunological response of the host organism, such as for instance an enhanced or improved immunological response or alternatively a decreased or reduced immunological response. The type of immunological response of an individual to a pathological condition may characterize the immune responder phenotype. The immunological response may be compared between individuals each of which being afflicted with the pathological condition, thereby allowing differentiation between or identification of different immune responder phenotypes, or alternatively may be compared between individuals afflicted with the pathological condition and individuals not afflicted with the pathological condition.

In certain embodiments, the pathological condition as referred to herein is an infection, autoimmune disease, allergy, or cancer. It is to be understood, that in aspects and embodiments wherein reference is made to prophylaxis, such means that the pathological condition referred to is to be prevented, such as for instance the prevention of infection, autoimmune disease, allergy, or cancer. More general, the pathological condition as referred to herein may include any pathological condition in which the immune system is involved and/or the immune system reacts abnormally or inappropriately, and may for instance also include graft versus host disease.

In certain embodiments, infection is due to bacteria, virus, protozoa, parasite, or fungus.

In certain embodiments, infection is a bacterial infection. In certain embodiments, the bacterial infection is infection due to *Bacillus* sp. (e.g. *Bacillus anthracis, Bacillus cereus*), *Bartonella* sp. (e.g. *Bartonella henselae, Bartonella quintana*), *Bordetella* sp. (e.g. *Bordetella pertussis*), *Borrelia* sp. (e.g. *Borrelia burgdorferi, Borrelia garinii, Borrelia afzelii, Borrelia recurrentis*), *Brucella* sp. (e.g. *Brucella abortus, Brucella canis, Brucella melitensis, Brucella suis*), *Campylobacter* sp. (e.g. *Campylobacter jejuni*), *Chlamydia* sp. (e.g. *Chlamydia pneumoniae, Chlamydia trachomatis*), *Chlamydophila* sp. (e.g. *Chlamydophila psittaci*), *Clostridium* sp. (e.g. *Clostridium botulinum, Clostridium difficile, Clostridium perfringens, Clostridium tetani*), *Corynebacterium* sp. (e.g. *Corynebacterium diphtheria*), *Enterococcus* sp. (e.g. *Enterococcus faecalis, Enterococcus faecium*), *Escherichia* sp. (e.g. *Escherichia coli*), *Francisella* sp. (e.g. *Francisella tularensis*), *Haemophilus* sp. (e.g. *Haemophilus influenzae*), *Helicobacter* sp. (e.g. *Helicobacter pylori*), *Legionella* sp. (e.g. *Legionella pneumophila*), *Leptospira* sp. (e.g. *Leptospira interrogans, Leptospira santarosai, Leptospira weilii, Leptospira noguchii*), *Listeria* sp. (e.g. *Listeria monocytogenes*), *Mycobacterium* sp. (e.g. *Mycobacterium leprae, Mycobacterium tuberculosis, Mycobacterium ulcerans*), *Mycoplasma* sp. (e.g. *Mycoplasma pneumoniae*), *Neisseria* sp. (e.g. *Neisseria gonorrhoeae, Neisseria meningitidis*), *Pseudomonas* sp. (e.g. *Pseudomonas aeruginosa*), *Rickettsia* sp. (e.g. *Rickettsia rickettsia*), *Salmonella* sp. (e.g. *Salmonella typhi, Salmonella typhimurium*), *Shigella* sp. (e.g. *Shigella sonnei*), *Staphylococcus* sp. (e.g. *Staphylococcus aureus, Staphylococcus epidermidis, Staphylococcus saprophyticus*), *Streptococcus* sp. (e.g. *Streptococcus agalactiae, Streptococcus pneumoniae, Streptococcus pyogenes*), *Treponema* sp. (e.g. *Treponema pallidum*), *Ureaplasma* sp. (e.g. *Ureaplasma urealyticum*), *Vibrio* sp. (e.g. *Vibrio cholerae*), or *Yersinia* sp. (e.g. *Yersinia pestis, Yersinia enterocolitica, Yersinia pseudotuberculosis*).

In certain embodiments, infection is a viral infection. In certain embodiments, the viral infection is infection due to Adenoviridae (e.g. Adenovirus), Herpesviridae (e.g. Herpes simplex, type 1, Herpes simplex, type 2, Varicella-zoster virus, Epstein-barr virus, Human cytomegalovirus, Human herpesvirus, type 8), Papillomaviridae (e.g. Human papillomavirus), Polyomaviridae (e.g. BK virus, JC virus), Poxviridae (e.g. Smallpox), Hepadnaviridae (e.g. Hepatitis B virus), Parvoviridae (e.g. Parvovirus B19), Astroviridae (e.g. Human astrovirus), Caliciviridae (e.g. Norwalk virus), Picornaviridae (e.g. coxsackievirus, hepatitis A virus, poliovirus, rhinovirus), Coronaviridae (e.g. Severe acute respiratory syndrome virus), Flaviviridae (e.g. Hepatitis C virus, yellow fever virus, dengue virus, West Nile virus, TBE virus), Togaviridae (e.g. Rubella virus), Hepeviridae (e.g. Hepatitis E virus), Retroviridae (e.g. Human immunodeficiency virus (HIV)), Orthomyxoviridae (e.g. Influenza virus), Arenaviridae (e.g. Lassa virus), Bunyaviridae (e.g. Crimean-Congo hemorrhagic fever virus, Hantaan virus), Filoviridae (e.g. Ebola virus, Marburg virus), Paramyxoviridae (e.g. Measles virus, Mumps virus, Parainfluenza virus, Respiratory syncytial virus), Rhabdoviridae (e.g. Rabies virus), Hepatitis D, or Reoviridae (e.g. Rotavirus, Orbivirus, Coltivirus, Banna virus).

In certain embodiments, infection is a protozoal or parasitic infection. In certain embodiments, the protozoan or parasitic infection is infection due to Euglenozoa (e.g. *Trypanosoma cruzi, Trypanosoma brucei, Leishmania* spp.), Heterolobosea (e.g. *Naegleria fowleri*), Diplomonadida (e.g. *Giardia intestinalis*), Amoebozoa (e.g. *Acanthamoeba castellanii, Balamuthia mandrillaris, Entamoeba histolytica*), Blastocystis (e.g. *Blastocystis hominis*), Apicomplexa (e.g. *Babesia microti, Cryptosporidium parvum, Cyclospora cayetanensis, Plasmodium* spp., *Toxoplasma gondii*), Roundworm infection (nematodiasis) (e.g. Filariasis (*Wuchereria bancrofti, Brugia malayi* infection), Onchocerciasis (*Onchocerca volvulus* infection), Soil-transmitted helminthiasis including ascariasis (*Ascaris lumbricoides* infection, trichuriasis (*Trichuris* infection), and hookworm infection (includes Necatoriasis and *Ancylostoma duodenale* infection), Trichostrongyliasis (*Trichostrongylus* spp. infection), Dracunculiasis (guinea worm infection)); Tapeworm infection (cestodiasis) (e.g. Echinococcosis (*Echinococcus* infection), Hymenolepiasis (*Hymenolepis* infection), Taeniasis/cysticercosis (*Taenia* infection), Coenurosis (*T. multiceps, T. serialis, T. glomerata* and T. brauni infection)); Trematode infection (trematodiasis) (e.g. Amphistomiasis (amphistomes infection), Clonorchiasis (*Clonorchis sinensis* infection), Fascioliasis (*Fasciola* infection), Fasciolopsiasis (*Fasciolopsis buski* infection), Opisthorchiasis (*Opisthorchis* infection), Paragonimiasis (*Paragonimus* infection), Schistosomiasis/bilharziasis (*Schistosoma* infection)); and Acanthocephala infection (e.g. *Moniliformis* infection).

In certain embodiments, infection is a fungal infection. In certain embodiments, the fungal infection is infection due to *Candida* species, such as *C. albicans; Cryptococcus* species, such as *C. neoformans, C. gattii; Aspergillus* species, such as *A. fumigatus* and *A. flavus; Pneumocystis* species, such as *P. carinii; Coccidioides* species such as *C. immitis; Trichophyton* species such as *T. verrucosum; Blastomyces* species such as *B. dermatitidis; Histoplasma* species such as *H. capsulatum; Paracoccidioides* species such as *P. brasiliensis; Mucoromycotina* sp.; *Sporothrix* sp, such as *S. schenckii*; and *Pythium* species such as *P. insidiosum*.

In certain embodiments autoimmune diseases are selected from Myocarditis, Postmyocardial infarction syndrome, Postpericardiotomy syndrome, Subacute bacterial endocarditis, Anti-Glomerular Basement Membrane nephritis, Interstitial cystitis, Lupus nephritis, Autoimmune hepatitis, Primary biliary cirrhosis, Primary sclerosing cholangitis, Antisynthetase syndrome, Alopecia Areata, Autoimmune Angioedema, Autoimmune progesterone dermatitis, Autoimmune urticaria, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosus, Linear IgA disease, Morphea, Pemphigus vulgaris, Pityriasis lichenoides et varioliformis acuta, Mucha-Habermann disease, Psoriasis, Systemic scleroderma, Vitiligo, Addison's disease, Autoimmune polyendocrine syndrome, Autoimmune polyendocrine syndrome type 2, Autoimmune polyendocrine syndrome type 3, Autoimmune pancreatitis, Diabetes mellitus type 1, Autoimmune thyroiditis, Ord's thyroiditis, Graves' disease, Autoimmune Oophoritis, Endometriosis, Autoimmune orchitis, Sjogren's syndrome, Autoimmune enteropathy, Celiac disease, Crohn's disease, Microscopic colitis, Ulcerative colitis, Antiphospholipid syndrome, Aplastic anemia, Autoimmune hemolytic anemia, Autoimmune lymphoproliferative syndrome, Autoimmune neutropenia, Autoimmune thrombocytopenic purpura, Cold agglutinin disease, Essential mixed cryoglobulinemia, Evans syndrome, IgG4-related systemic disease, Paroxysmal nocturnal hemoglobinuria, Pernicious anemia, Pure red cell aplasia, Thrombocytopenia, Adiposis dolorosa, Adult-onset Still's disease, Ankylosing Spondylitis, CREST syndrome, Drug-induced lupus, Enthesitis-related arthritis, Eosinophilic fasciitis, Felty syndrome, Juvenile Arthritis, Lyme disease (Chronic), Mixed connective tissue disease, Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus, Undifferentiated connective tissue disease, Dermatomyositis, Fibromyalgia, Inclusion body myositis, Myositis, Myasthenia gravis, Neuromyotonia, Paraneoplastic cerebellar degeneration, Polymyositis, Acute disseminated encephalomyelitis, Acute motor axonal neuropathy, Anti-N-Methyl-D-Aspartate Receptor Encephalitis, Balo concentric sclerosis, Bickerstaff's encephalitis, Chronic inflammatory demyelinating polyneuropathy, Guillain-Barre syndrome, Hashimoto's encephalopathy, Idiopathic inflammatory demyelinating diseases, Lambert-Eaton myasthenic syndrome, Multiple sclerosis, Pediatric Autoimmune Neuropsychiatric Disorder Associated with *Streptococcus*, Progressive inflammatory neuropathy, Restless leg syndrome, Stiff person syndrome, Sydenham chorea, Transverse myelitis, Autoimmune retinopathy, Autoimmune uveitis, Cogan syndrome, Graves ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, Tolosa-Hunt syndrome, Autoimmune inner ear disease, Ménière's disease, Anti-neutrophil cytoplasmic antibody-associated vasculitis, Behçet's disease, Churg-Strauss syndrome, Giant cell arteritis, Henoch-Schonlein purpura, Kawasaki's disease, Leukocytoclastic vasculitis, Lupus vasculitis, Rheumatoid vasculitis, Microscopic polyangiitis, Polyarteritis nodosa, Polymyalgia rheumatica, Urticarial vasculitis, and Vasculitis.

In certain embodiments allergic diseases are selected from allergic rhinitis, drug allergy, latex allergy, insect sting/bite allergy, urticarial, contact dermatitis, allergic conjunctivitis, hay fever, food allergies, atopic dermatitis, allergic asthma, and anaphylaxis.

In certain embodiments cancer is selected from carcinoma, sarcoma, lymphoma, leukemia, germ cell tumors, blastoma. In certain embodiments cancer is selected from Acute lymphoblastic leukemia (ALL); Acute myeloid leukemia; Adrenocortical carcinoma; AIDS-related cancers; AIDS-related lymphoma; Anal cancer; Appendix cancer; Astrocytoma, childhood cerebellar or cerebral; Basal-cell carcinoma; Bile duct cancer, extrahepatic (see cholangiocarcinoma); Bladder cancer; Bone tumor, osteosarcoma/malignant fibrous histiocytoma; Brainstem glioma; Brain cancer; Brain tumor, cerebellar astrocytoma; Brain tumor, cerebral astrocytoma/malignant glioma; Brain tumor, ependymoma; Brain tumor, medulloblastoma; Brain tumor, supratentorial primitive neuroectodermal tumors; Brain tumor, visual pathway and hypothalamic glioma; Breast cancer; Bronchial adenomas/carcinoids; Burkitt's lymphoma; Carcinoid tumor, childhood; Carcinoid tumor, gastrointestinal; Carcinoma of unknown primary; Central nervous system lymphoma, primary; Cerebellar astrocytoma, childhood; Cerebral astrocytoma/malignant glioma, childhood; Cervical cancer; Childhood cancers; Chondrosarcoma; Chronic lymphocytic leukemia; Chronic myelogenous leukemia; Chronic myeloproliferative disorders; Colon cancer; Cutaneous T-cell lymphoma; Desmoplastic small round cell tumor; Endometrial cancer; Ependymoma; Esophageal cancer; Ewing's sarcoma in the Ewing family of tumors; Extracranial germ cell tumor, childhood; Extragonadal germ cell tumor; Extrahepatic bile duct cancer; Eye cancer, intraocular melanoma; Eye cancer, retinoblastoma; Gallbladder cancer; Gastric (stomach) cancer; Gastrointestinal carcinoid tumor; Gastrointestinal stromal tumor (GIST); Germ cell tumor: extracranial, extragonadal, or ovarian; Gestational trophoblastic tumor; Glioma of the brain stem; Glioma, childhood cerebral astrocytoma; Glioma, childhood visual pathway and hypothalamic; Gastric carcinoid; Hairy cell leukemia; Head and neck cancer; Heart cancer; Hepatocellular (liver) cancer; Hodgkin lymphoma; Hypopharyngeal cancer; Hypothalamic and visual pathway glioma, childhood; Intraocular melanoma; Islet cell carcinoma (endocrine pancreas); Kaposi sarcoma; Kidney cancer (renal cell cancer); Laryngeal cancer; Leukaemias; Leukaemia, acute lymphoblastic (also called acute lymphocytic leukaemia); Leukaemia, acute myeloid (also called acute myelogenous leukemia); Leukaemia, chronic lymphocytic (also called chronic lymphocytic leukemia); Leukemia, chronic myelogenous (also called chronic myeloid leukemia); Leukemia, hairy cell; Lip and oral cavity cancer; Liposarcoma; Liver cancer (primary); Lung cancer, non-small cell; Lung cancer, small cell; Lymphomas; Lymphoma, AIDS-related; Lymphoma, Burkitt; Lymphoma, cutaneous T-Cell; Lymphoma, Hodgkin; Lymphomas, Non-Hodgkin (an old classification of all lymphomas except Hodgkin's); Lymphoma, primary central nervous system; Macroglobulinemia, Waldenström; Male breast cancer; Malignant fibrous histiocytoma of bone/osteosarcoma; Medulloblastoma, childhood; Melanoma; Melanoma, intraocular (eye); Merkel cell cancer; Mesothelioma, adult malignant; Mesothelioma, childhood; Metastatic squamous neck cancer with occult primary; Mouth cancer; Multiple endocrine neoplasia syndrome, childhood; Multiple myeloma/plasma cell neoplasm; Mycosis fungoides; Myelodysplastic syndromes; Myelodysplastic/myeloproliferative diseases; Myelogenous leukemia, chronic; Myeloid leukemia, adult acute; Myeloid leukemia, childhood acute; Myeloma, multiple (cancer of the bone-marrow); Myeloproliferative disorders, chronic; Myxoma; Nasal cavity and paranasal sinus cancer; Nasopharyngeal carcinoma; Neuroblastoma; Non-Hodgkin lymphoma; Non-small cell lung cancer; Oligodendroglioma; Oral cancer; Oropharyngeal cancer; Osteosarcoma/malignant fibrous histiocytoma of bone; Ovarian cancer; Ovarian epithelial cancer (surface epithelial-stromal tumor); Ovarian germ cell tumor; Ovarian low malignant potential tumor; Pancreatic cancer; Pancreatic cancer, islet cell; Paranasal sinus and nasal cavity cancer; Parathyroid cancer; Penile cancer; Pharyngeal cancer; Pheochromocytoma; Pineal astrocytoma; Pineal germinoma; Pineoblastoma and supratentorial primitive neuroectodermal tumors, childhood; Pituitary adenoma; Plasma cell neoplasia/Multiple myeloma; Pleuropulmonary blastoma; Primary central nervous system lymphoma; Prostate cancer; Rectal cancer; Renal cell carcinoma (kidney cancer); Renal pelvis and ureter, transitional cell cancer; Retinoblastoma; Rhabdomyosarcoma, childhood; Salivary gland cancer; Sarcoma, Ewing family of tumors; Sarcoma, Kaposi; Sarcoma, soft tissue; Sarcoma, uterine; Sezary syndrome; Skin cancer (non-melanoma); Skin cancer (melanoma); Skin carcinoma, Merkel cell; Small cell lung cancer; Small intestine cancer; Soft tissue sarcoma; Squamous cell carcinoma—see skin cancer (non-melanoma); Squamous neck cancer with occult primary, metastatic; Stomach cancer; Supratentorial primitive neuroectodermal tumor, childhood; T-Cell lymphoma, cutaneous—see Mycosis Fungoides and Sézary syndrome; Testicular cancer; Throat cancer; Thymoma; Thymoma, childhood; Thymoma and thymic carcinoma; Thyroid cancer; Thyroid cancer, childhood; Transitional cell cancer of the renal pelvis and ureter; Trophoblastic tumor, gestational; Unknown primary site, carcinoma of, adult; Unknown primary site, cancer of, childhood; Ureter and renal pelvis, transitional cell cancer; Urethral cancer; Uterine cancer, endometrial; Uterine sarcoma; Vaginal cancer; Visual pathway and hypothalamic glioma, childhood; Vulvar cancer; Waldenström macroglobulinemia; Wilms tumor (kidney cancer), childhood.

In certain embodiments, the infectious disease is a prion. Prions are infectious pathogens that do not contain nucleic acids. These abnormally folded proteins are found characteristically in some diseases such as scrapie, bovine spongiform encephalopathy (mad cow disease) and Creutzfeldt-Jakob disease.

The cells as referred to herein according to the invention originate from an animal, including vertebrate and non-vertebrate animals, preferably vertebrate animals, such as without limitation including mammalians, reptiles, fish, birds, amphibians, preferably mammalians, such as without limitation primates, rodents, carnivores, artiodactyla, lagomorpha, etc. the cells may be human or non-human. The cells may be derived for instance from human, mouse, rat, or rabbit.

Biological samples as used in the various methods or compositions as discussed herein in one embodiment comprise immune cells, developing or undifferentiated cells, or healthy cells. Such biological samples may for instance comprise lymphoid tissues, such as primary or secondary lymph tissues (e.g. lymph fluid, thymus, lymph nodes, spleen, bone marrow, tonsils, Peyer's patches, mucosa associated lymphoid tissue (MALT), appendix) or blood. Alternatively, the biological sample may be any tissue sample comprising immune cells, developing or undifferentiated cells, or healthy cells.

According to certain aspects or embodiments of the invention, differential expression of protein or RNA is performed between samples, which may be differential expression of proteins or RNA based on single cell analyses. Such single cell based analyses may be performed by techniques as discussed herein (e.g., Drop-Seq).

In certain aspects and embodiments, the invention relates to modulants, their use, and methods for identifying modulants, as discussed herein. As used herein, the term modulant may be used interchangeably with modulator. As used herein, an modulant refers preferably to a compound (or combination of compounds) which are capable of altering or affecting the functioning of the cell system, or of particular components of the cell system, such as one or more particular cells or cell types. A modulant may alter for instance the cell state or phenotype of particular immune cells or immune cell (sub)populations. A modulant may for instance increase or induce or alternatively decrease or ablate particular immune cells or immune cell (sub)populations, such that the entire immune cell population obtains a different functionality, such as for instance an improved immunological response towards a pathological conditions. Modulants include any potential class of biologically active agent, such as for instance small molecules, drugs, TLR agonists, antagonists, genetic perturbations (e.g. knock-out, knockdown, or other types of (inactivating or otherwise modulating) mutations), etc. Methods for altering signatures, immune responder phenotypes, or immune cells such as immune cell (sub)populations may include contacting particular immune cells (or populations) with modulants as discussed herein, which may be in vitro or in vivo. If performed in vitro, the so-treated cells may after treatment be administered to an individual in need thereof. In certain embodiments, the modulant may be provided in pharmaceutical compositions, and may for instance be included in a vaccine. Typically, a vaccine further comprises an antigen, wherein said antigen is preferably specific for a particular pathological condition and/or may further comprise immune cells (e.g. antigen presenting cells, optionally primer with antigen).

The present invention also relates to compositions, such as pharmaceutical compositions, comprising the cells or cell (sub)populations as discussed herein, such as the cells or cell (sub)populations having particular signature as discussed herein, or the cells or cell (sub)populations associated with or characteristic of particular responder phenotypes as discussed herein.

As noted elsewhere, pharmaceutical compositions as taught herein comprise one or more pharmaceutically acceptable excipient.

The term "pharmaceutically acceptable" as used herein is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. The use of such media and agents for pharmaceutical active substances is well known in the art. Such materials should be non-toxic and should not interfere with the activity of the cells or active components (e.g. modulators).

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infusion. The skilled person will understand that compositions comprising modulators as discussed herein which are to be administered orally or topically will usually not comprise cells, although it may be envisioned for oral compositions to also comprise cells, for example when gastro-intestinal tract indications are treated. Each of the compounds as discussed herein (e.g. cells, modulators) may be administered by the same route or may be administered by a different route. By means of example, and without limitation, the cells may be administered parenterally and the modulator may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of its environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

If desired, cell preparation can be administered on a support, scaffold, matrix or material to provide improved tissue regeneration. For example, the material can be a granular ceramic, or a biopolymer such as gelatine, collagen, or fibrinogen. Porous matrices can be synthesized according to standard techniques (e.g., Mikos et al., Biomaterials 14: 323, 1993; Mikos et al., Polymer 35:1068, 1994; Cook et al., J. Biomed. Mater. Res. 35:513, 1997). Such support, scaffold, matrix or material may be biodegradable or non-biodegradable. Hence, the cells may be transferred to and/or cultured on suitable substrate, such as porous or non-porous substrate, to provide for implants. For example, cells that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g. by impregnating said support with a liquid suspension containing said cells. The impregnated supports obtained in this way can be implanted in a human subject. Such impregnated supports can also be re-cultured by immersing them in a liquid culture medium, prior to being finally implanted. The three-dimensional solid support needs to be biocompatible so as to enable it to be implanted in a human. It may be biodegradable or non-biodegradable.

The cells or cell (sub)populations can be administered in a manner that permits them to survive, grow, propagate and/or differentiate towards desired cell types (e.g. differentiation) or cell states. The cells or cell (sub)populations may be grafted to or may migrate to and engraft within the intended organ, such as, e.g., liver. Engraftment of the cells or cell (sub)populations in other places, tissues or organs such as liver, spleen, pancreas, kidney capsule, peritoneum or omentum may be envisaged.

In an embodiment the pharmaceutical cell preparation as defined above may be administered in a form of liquid composition. In embodiments, the cells or pharmaceutical composition comprising such can be administered systemically, topically, within an organ or at a site of organ dysfunction or lesion.

Preferably, the pharmaceutical compositions may comprise a therapeutically effective amount of the desired cells. The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

In certain embodiments, the invention involves compositions as discussed herein, such as the pharmaceutical compositions as discussed herein.

Platforms for Profiling Single Cells

Cells may be considered processing units. Core constituents include skin cells, such as fibroblasts, adipocytes and epithelial cells; immune cells such as megakaryocytes, dendritic cells and T cells: brain cells such as neurons, ependymal cells and astrocytes and muscle cells such as smooth muscle, skeletal muscle and cardiac muscle. However, grouped cells are not identical (see, e.g., M D Slack et al. PNAS 105, (2008) and P. Dalerba et al. Nat. Biotech. 29, (2011)) and differences can underlie unique behaviors (see, e.g., A A Cohen et al. Science, 322 (2008), S Tay et al. Nature 466, (2010) and O. Feinerman et al. Mol. Sys. Bio. 437, (2010)).

Four fundamental questions may be asked: 1. How do cells respond to change? 2. Which differences influence those responses? 3. When is variability mitigated and when is it leveraged? 4. How does heterogeneity affect the interactions between functionally different cells?To address these questions, one must be able to precisely measure and manipulate large numbers of single mammalian cells in parallel.

For developing new platforms, Applicants leverage nano- and micro-fabrication to develop new platforms for thoroughly and controllably profiling single cells.

Conventional methods for studying single cells include optical microscopy and flow/mass cytometry. With optical microscopy, temporal and spatial information may be obtained, however there is limited depth due to spectral overlap between fluorophores. With flow/mass cytometry (see, e.g., S C Bendell et al. Science, 332 (2011), one can profile many observables (such as 6-16 for flow cytometry and 34+ for mass cytometry) and it is easy to achieve a large number of statistics. However, no spatial information may be obtained and it is extremely difficult to follow the same cell overtime.

Intercellular signaling is a compounding variable. Controlling a cellular microenvironment may be done by any device or microdevice—such as reverse emulsions, microwells and microfluidics—that can define and maintain a constant, known the extracellular milieu.

The present invention also involves utilizing nano- and micro-technology to complement current single cell studies. Using microstructures, Applicants can restrain single cells or their components at concentrations similar to 0.01-100 million cells/mL.

Traditional population measurements involve lots of starting material and enable deep profiling of a particular molecular species. For instance, normally, upon activation, a naïve T cell will differentiate into one of several, functionally distinct T helper cell sub-types, depending upon the cytokine environment—some of these promote immune responses, whereas others 'shut down' immune activity. Each individual T helper also secretes lineage-dependent cytokines that can influence its own actions, as well as those of its peers. The correct balance between the sub-types is critical to normal immune function, and defects in the guiding molecular circuits can lead to autoimmune disorders, such as Multiple Sclerosis and Psoriasis, and allergies. Studying cellular decision making in populations of T cells on a single cell basis will reveal fundamental principles underlying cellular diversity, aid in developing diagnostics and therapeutic strategies for immune disorders, and provide a paradigm for similar studies in other mammalian cells.

To decouple single T cells from themselves and their peers, Applicants fabricate ordered "capture" sites for restraining cells during rapid solution perfusion. This enables examination of how cellular responses depend upon component heterogeneity in the absence of compounding external factors. By systematically controlling the levels of different cytokines, antigens, peptides, secreted factors, ligands, ions, DNA, or RNA in the perfusion media, Applicants also investigate how extracellular signaling affects intracellular circuits. Importantly, Applicants integrate optical and microfluidic controls so that optical interrogation and transcriptome analysis can be performed on the same cell.

HIV

In one embodiment, the present invention relates to innate immunity against a pathogen HIV-1 and immune cells, such as functional cDC maturation, at the single-cell level analyzed by for example, RNAseq. Applicants identified a highly functional cDC subset present in EC that might provide critical information for future clinical approaches to induce highly-effective T cell responses in a larger number of patients and individuals.

To further unravel complex immune system heterogeneity, in particular to establish cellular networks and cell interactions, aiming at improving diagnostic or therapeutic efforts, Applicants profiled cDCs from an EC at rest or exposed to pseudo-typed HIV-1 virus using single-cell RNA-Seq (scRNA-Seq), a recently developed approach that enables unbiased identification of the cell types, states, circuits, and molecular drivers normally convolved in a complex ensemble behavior (Shalek et al. *Nature* 2013; 2014; Patel et al. *Science* 2014; Satija and Shalek *Trends in Immunology* 2014). Applicants applied scRNA-Seq to identify a highly functional subpopulation of elite controller dendritic cells responding to viral infection. Applicants developed and validated a computational infrastructure for identifying intracellular nodes and selecting immunomodulators that preferentially rebalance immune subset composition. Using identified immunomodulators, such as TLR3 ligands, such as poly I:C, Applicants induced a larger population of the functional subset of dendritic cells in normal donors, such as characterized by (surface) expression of CD64 and PD-L1, or high (surface) expression of CD64 and PD-L1, or increased (surface) expression of CD64 and PD-L1 (e.g. as compared to dendritic cells not belonging to the functional subset).

Unexpectedly, virus exposed cDCs separated into three distinct response groups, characterized by substantial differences in transcriptional programs associated with cellular activation and antiviral response. These clusters—influenced but not defined by viral interactions—revealed a new, highly functional group of cDCs, characterized by strong expression of innate immune activation genes and phenotypically distinguished by high surface expression of CD64 and PD-L1. Importantly, this group of cDCs has superior antigen presentation and T cell activation capabilities in vitro, and, although preferentially enriched in ECs, is common to all individuals. Using a combination of computational and experimental approaches to rationally uncover and test putative immunomodulators that can alter the relative abundances of these cDC groups, Applicants show that one can selectively adjuvant or inhibit this cDC subgroup in healthy individuals and ECs, respectively. With respect to EC, the study reveals functional heterogeneity in EC cDC responses and identifies transcriptional signatures associated with immune control of HIV-1 in cDCs; more generally, it demonstrates that immune system composition informs function and details new methodologies for identifying and rationally rebalancing salient components to realize, therapeutically or prophylactically, a desired response.

It has been established that these findings are not per se and only relevant for or characteristic of cDCs in control of HIV infection, but instead can be extrapolated to different types of immune cells, different types of pathological conditions, and/or different types of phenotypes or phenotypical behaviours, both at single cell levels as well as cell population level.

B Cells/Monocytes

An objective of the B cell study was to identify patterns of differential expression (DE) between an elite controller and a non-neutralizer in cells tetramer-sorted for HIV protein (gp140) and non-sorted samples.

Expression study steps at the population level include a differential expression analysis which involves projection (all genes) and a direct comparison (gene-by-gene). Expression study steps at the cell level involves clustering and DE-analysis.

Populations

One embodiment of the present invention is aimed at finding DE genes associated with neutralizing antibody (NA) breadth. NA breadth has been defined as an integer in the phenotyping, and this integer has changed since the original phenotyping.

One embodiment of the invention involves identifying signatures of HIV-1 specific broadly neutralizing antibody (bnAb) ontogeny using a systems biology approach, specifically identification of leukocellular subset-specific signatures defining HIV-1 controllers with and without HIV-1-specific neutralizing breadth, identification of signatures during pre-infection or early infection that prospectively predict the development of neutralizing breadth during the ensuing disease process and generation of a comprehensive multidimensional database integrating all clinical, transcriptional, epigenetic and functional immunologic data.

Single-Cell RNAseq Analysis

One problem with RNA-seq analysis of bulk cell populations is that cell heterogeneity may confound results. Applicants therefore have started to use scRNA-seq assays for further investigation of dendritic cells. In initial experiments LPS-stimulated bone marrow derived dendritic cells (BMDCs) were examined. While the gene expression levels of population replicates were tightly correlated with one another, there were substantial differences in gene expression between individual cells.

When Applicants compared dendritic cells with and without exposure to HIV on the population level, Applicants identified 26 genes that are differentially expressed between those two conditions. However, cells exposed to HIV could be classified in three different groups: Two groups that were grossly different from gene expression patterns from HIV-unexposed cells, and one group that appear to have transcriptional signatures similar to HIV-1 unexposed cells. This technology shows single-cell RNA-seq of DC is technically possible, and allows to delineate distinct classes of DC with altered gene expression patterns.

To elaborate on this point, Applicants used this methodological approach to better understand gene expression patterns associated with the development of neutralizing breadth. Systems-level responses in our bodies represent the combined and coordinated behaviors of a highly diverse ensemble of cells. In the immune system, many specialized cells must work together to defend against myriad pathogenic threats, maintain long-term memory, and establish tolerance (Germain 2012). Moreover, the interplay between these cells must establish checks and balances to protect against autoimmunity or immunodeficiency (Littman and Rudensky 2010, Yosef, Shalek et al. 2013). Measuring these phenomena in bulk, however, blends and potentially masks the unique contributions of individual cells, particularly when their behaviors are heterogeneous or driven by rare cell types/states.

To overcome this issue, to date, analyses of immune cells have primarily relied on first dividing the system into distinct subpopulations from the "top-down," typically based on the expression of cellular markers, and subsequently characterizing each bin independently. This strategy has cataloged the major cell types of the mammalian immune system, established more nuanced functional divisions (Shay and Kang 2013), and uncovered that balanced composition is essential for proper function. Illustratively, overproduction of a subset of T helper cells (pro-inflammatory Th17) (Yosef, Shalek et al. 2013), or an imbalance in the relative proportions of DC subtypes (Nakahara, Uchi et al. 2010), can lead to autoimmune disease; similarly, in cancer, the density and diversity of tumor-infiltrating lymphocytes (TILs) has been shown to be predictive of tumor recurrence and clinical outcome (Galon, Costes et al. 2006). Yet, while informative, these "top-down" approaches depend on pre-selected markers, biasing experimental design. Moreover, recent molecular studies have shown that even "identical" cells can substantially differ in gene expression, protein levels and phenotypic output (Cohen, Geva-Zatorsky et al. 2008, Raj and Van Oudenaarden 2009, Feinerman, Jentsch et al. 2010, Sharma, Lee et al. 2010, Bendall, Simonds et al. 2011, Dalerba, Kalisky et al. 2011), with important functional consequences (Cohen, Geva-Zatorsky et al. 2008, Feinerman, Jentsch et al. 2010, Sharma, Lee et al. 2010), highlighting the shortcomings of "top-down" schemes.

A complementary approach is to examine a system from the "bottom-up," profiling its component cells individually. Until recently, single-cell-based approaches, such as fluorescence activated cell sorting (FACS) or immunofluorescence, had been technically limited to probing a few pre-selected RNAs or proteins (Cohen, Geva-Zatorsky et al. 2008, Raj and Van Oudenaarden 2009, Sharma, Lee et al. 2010, Bendall, Simonds et al. 2011, Dalerba, Kalisky et al. 2011), hindering one's ability to uncover novel factors. The recent emergence of single cell genomic approaches, and especially single-cell RNA-Seq (scRNA-seq), opens a new path for unbiased molecular profiling of individual immune cells from which Applicants can identify cell states and their associated signatures. For example, in Applicant's own work, using scRNA-Seq of 18 'identical' dendritic cells (DCs) exposed to lipopolysaccharide (LPS), Applicants discovered extensive bimodality in the DC response at multiple levels, including in the expression of key immune response genes and the splicing of RNA, which Applicants independently validated by RNA-FISH of 25 selected transcripts. By examining the co-variation between different genes across just 18 single cells, Applicants were able to decipher two distinct cell states and an interferon-driven antiviral circuit that Applicants subsequently validated in murine knockout models. Applicants then developed a high-throughput workflow for profiling many individual cells across different experimental conditions and used it to prepare scRNA-Seq libraries from over 1,800 BMDCs stimulated with three pathogenic components (Shalek, Satija et al. 2014). Here, Applicants identified a rare (~1%) subpopulation of precocious responders that expresses a core module of antiviral genes very early; this same module becomes active in all cells at later time points. By stimulating cells individually in sealed microfluidic chambers and analyzing DCs from knockout mice, Applicants showed that these precocious cells propagate and coordinate this response through interferon-mediated paracrine signaling. Surprisingly, the precocious cells are also essential for suppressing an early-induced inflammatory gene module. Taken together, these findings demonstrate the power and promise of single cell genomics, and highlight the importance of cell type/state, the microenvironment and intercellular communication in establishing and coordinating complex dynamic responses at the ensemble/system level.

Determining Genetic Interactions

In one aspect, the invention provides a method for determining genetic interactions. This method involves causing a set of P genetic perturbations in cells, wherein the method may comprise: determining, based upon random sampling, a subset of $\pi$ genetic perturbations from the set of P genetic perturbations; performing said subset of $\pi$ genetic perturbations in a population of cells; performing single-cell molecular profiling of the population of genetically perturbed cells of step; inferring single-cell molecular profiles for the set of P genetic perturbations in cells.

The perturbation methods as discussed herein may also be used to validate particular gene signatures or specific modulators, such as for instance to identify relevant genes or pathways which are involved to obtain a particular gene signature, responder phenotype, or particular cell (sub) population, or cell state.

The population of cells with a plurality of genomic sequence or perturbation conditions involves a plurality of cells and perturbations to be tested and measurements sampled to obtain meaningful data and to infer appropriate circuits. The number of genes perturbed, and how many are perturbed simultaneously (the order of the perturbation, pairs, triplets, etc.) varies. In a tissue with n cell types, the rarest present in m %, how many cells X do you need to sequence so that you have at least Y of the rarest subtype.

For example, ~500 cells ensures ≥95% chance of including ≥10 of each type, based on the following calculation. Assume the most conservative scenario that of M cell subtypes (for example, 12), all but one having the lowest predicted proportion (for example, $p_{min}=5\%$). Assuming that the Central Limit Theorem holds (a reasonable assumption when solving to detect at least 10 cells of each type) the number of cells of each type i, termed $T_i$, will distribute as $E[T_i]=N*p_{min}$, $STDV[T_i]=\sqrt{(N*p_{min}*(1-p_{min}))}$. The minimal N (total number of cells to profile) can be solved such that all (m−1) subtypes have at least n cells (the last, majority, subtype easily clears this threshold since its proportion is much higher). Applicants confirmed with simulation that the strategy conservatively holds in practice even for n<10, and take a margin of additional (conservative) error, to allow for subsequent failed RNA-Seq experiments (<20-30%, depending on protocol).

Modelling Genetic Interactions

The method of the invention may be used for determining genetic interactions, including modelling and/or analyzing such interactions. Such genetic interactions form part of cellular circuitry, in that the interactions reflect connections of components within one or more cellular pathways. Such pathways may be intracellular pathways or intercellular pathways.

In some embodiments, the method of the invention may further comprise determining genetic interactions.

In some embodiments, the method of the invention may further comprise confirming genetic interactions with additional genetic manipulations.

The method may further comprise a validation step, wherein additional manipulations are performed in order to confirm previously identified genetic interactions. Such validation step may include in vivo or in vitro experiments, such as gene inactivation, gene deletion, gene activation or over-expression, and combinations thereof. Such genetic manipulations may be performed with any genetic tool available in the art, comprising but not limited to RNAi, CRISPR-Cas based gene editing, nucleic acid transfection, etc.

Genetic Perturbations

In one aspect, said set of P genetic perturbations or said subset of $\pi$ genetic perturbations may comprise single-order genetic perturbations. Within the meaning of the present invention, single-order genetic perturbation means that a given cell undergoes a single genetic perturbation (one perturbation per cell).

In one aspect, said set of P genetic perturbations or said subset of $\pi$ genetic perturbations may comprise combinatorial genetic perturbations. Within the meaning of the present invention, combinatorial or higher-order genetic perturbation means that a given cell undergoes a combination of k single-order genetic perturbations (k perturbations per cell), with k>1. In some embodiments, k is an integer ranging from 2 to 15. In some embodiments, k=2, 3, 4, 5, 6, 7, 8, 9 or 10.

Within the meaning of the present invention, said genetic perturbation may comprise gene knock-down (gene repression or gene inactivation), gene knock-out (gene deletion), gene activation, gene insertion, or regulatory element modulation (deletion or mutation).

Combinations of different types of genetic perturbations are also envisioned within the meaning of the present invention. For example, a combination of genetic perturbations may comprise a knock-down for a first gene, combined to an activation of a second gene, etc.

In one aspect, said set of P genetic perturbations or said subset of $\pi$ genetic perturbations may comprise genome-wide perturbations. Genome-wide perturbations are genetic perturbations that affect loci across the entire genome. Genome-wide perturbation may include single perturbations of >100, >200, >500, >1,000, >2,500, >5,000, >10,000, >15,000 or >20,000 single genomic loci. The present invention encompasses k-order combinations of genome-wide perturbation.

In some embodiments, the method may comprise determining k-order genetic interactions.

In some embodiments, said set of P genetic perturbations may comprise combinatorial genetic perturbations, such as k-order combinations of single-order genetic perturbations, wherein k is an integer ranging from 2 to 15, and step (e) may comprise determining j-order genetic interactions, with j<k. Such embodiments rely on sampling higher-order interactions in order to more efficiently infer lower order ones. Given a limited number of possible assays, one is more powered to determine lower order interactions (e.g., 2-, 3-way) from measuring higher order interactions (e.g., 5-way) than from allotting all assays to the lower order, because any higher order interaction carries some information about all interaction terms up to that order (e.g., in compressed sensing, it informs in convolved form on additional Fourier coefficients). Thus, even if most interactions are low order (2- or 3-way) these embodiments are more powered to detect them.

CRISPR-Cas Systems

In some embodiments, RNAi- or CRISPR-Cas-based perturbation may be performed. Said perturbation may be performed (e.g. "delivered") in an array-format or pool-format. Some embodiments may comprise pooled single or combinatorial CRISPR-Cas-based perturbation with a genome-wide library of sgRNAs, wherein each sgRNA comprises a unique molecular identifier. In some embodiments, a step may comprise pooled combinatorial CRISPR-Cas-based perturbation with a genome-wide library of sgRNAs, wherein each sgRNA comprises a unique molecular identifier and is co-delivered with a reporter mRNA.

CRISPR-Cas systems, including CRISPR-Cas9 systems, as used herein, refer to non-naturally occurring systems derived from bacterial Clustered Regularly Interspaced Short Palindromic Repeats loci. These systems generally comprise an enzyme (Cas protein, such as Cas9 protein) and one or more RNAs. Said RNA is a CRISPR RNA and may be an sgRNA. Said RNA and/or said enzyme may be engineered, for example for optimal use in mammalian cells, for optimal delivery therein, for optimal activity therein, for specific uses in gene editing, etc.

sgRNA refers to a CRISPR single-guide RNA. This RNA is a component of a CRISPR-Cas system. The sequence of the sgRNA determines the target sequence for gene editing, knock-down, knock-out, insertion, etc. For genome-wide approaches, it is possible to design and construct suitable sgRNA libraries. Such sgRNAs may be delivered to cells using vector delivery such as viral vector delivery. Combination of CRISPR-Cas-mediated perturbations may be obtained by delivering multiple sgRNAs within a single cell. This may be achieved in pooled format. In the case of sgRNA viral vector delivery, combined perturbation may be obtained by delivering several sgRNA vectors to the same cell. This may also be achieved in pooled format, and number of combined perturbations in a cell then corresponds to the MOI (multiplicity of infection). Using CRISPR-Cas systems, one may generally implement MOI values of up to 10, 12 or 15.

The CRISPR-Cas system may be implemented in order to cause massively combinatorial molecular perturbations (MCMP), including single-order and combinatorial genome-wide genetic perturbations.

CRISPR-Cas-based gene editing allows to perform pooled genome-scale screens with expression readouts in primary cells (A Genome-wide CRISPR Screen in Primary Immune Cells to Dissect Regulatory Networks. Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. *Cell* July 15. (2015) 2015 July 30; 162(3):675-86. doi: 10.1016/j.cell.2015.06.059. Epub 2015 July 16).

In some embodiments, the present invention involves combinatorial perturbations by way of CRISPR-Cas (such as CRISPR-Cas9) assays. In accordance with the present invention, sampling a far-from-exhaustive number of higher order perturbations, when coupled with complex genomic readouts, may suffice to resolve most non-linear relations. Accordingly, in some aspects, the present invention relies on pooled, combinatorial perturbations with genomic readout into Massively Combinatorial Perturbation Profiling (MCPP).

In some embodiments, the method of the invention may comprise one or more CRISPR-Cas-based assays. Such CRISPR-Cas assays are advantageous for implementing a precise perturbation of genes and their expression levels.

In some embodiments, CRISPR-Cas systems may be used to knockout protein-coding genes by frameshifts (indels). Embodiments include efficient and specific CRISPR-Cas9 mediated knockout (Gilbert, L. A., Horibeck, M. A., Adamson, B., Villalta, J. E., Chen, Y., Whitehead, E. H., Guimaraes, C., Panning, B., Ploegh, H. L., Bassik, M. C., Qi, L. S., Kampmann, M. & Weissman, J. S. Genome-Scale CRISPR-Mediated Control of Gene Repression and Activation. *Cell*. 159, 647-661, doi:10.1016/j.cell.2014.09.029 (2014). PMCID:4253859; Ran, F. A., Cong, L., Yan, W. X., Scott, D. A., Gootenberg, J. S., Kriz, A. J., Zetsche, B., Shalem, O., Wu, X., Makarova, K. S., Koonin, E. V., Sharp, P. A. & Zhang, F. In vivo genome editing using *Staphylococcus aureus* Cas9. *Nature*. 520, 186-191, doi:10.1038/nature14299 (2015). PMCID:4393360), including a CRISPR mediated double-nicking to efficiently modify both alleles of a target gene or multiple target loci (Ran, F. A., Hsu, P. D., Lin, C. Y., Gootenberg, J. S., Konermann, S., Trevino, A. E., Scott, D. A., Inoue, A., Matoba, S., Zhang, Y. & Zhang, F. Double nicking by RNA-guided CRISPR Cas9 for enhanced genome editing specificity. *Cell*. 154, 1380-1389, doi:10.1016/j.cell.2013.08.021 (2013). PMCID: 3856256; Wang, H., Yang, H., Shivalila, C. S., Dawlaty, M. M., Cheng, A. W., Zhang, F. & Jaenisch, R. One-step generation of mice carrying mutations in multiple genes by CRISPR-Cas-mediated genome engineering. *Cell*. 153, 910-918, doi:10.1016/j.cell.2013.04.025 (2013). PMCID: 3969854) and implementation of a smaller Cas9 protein for delivery on smaller vectors (Ran, F. A., Cong, L., Yan, W. X., Scott, D. A., Gootenberg, J. S., Kriz, A. J., Zetsche, B., Shalem, O., Wu, X., Makarova, K. S., Koonin, E. V., Sharp, P. A. & Zhang, F. In vivo genome editing using *Staphylococcus aureus* Cas9. *Nature*. 520, 186-191, doi:10.1038/nature14299 (2015). PMCID:4393360).

CRISPR-mediated activation or inactivation (CRISPRa/i) systems may be used to activate or inactivate gene transcription. Briefly, a nuclease-dead (deactivated) Cas9 RNA-guided DNA binding domain (dCas9) (Qi, L. S., Larson, M. H., Gilbert, L. A., Doudna, J. A., Weissman, J. S., Arkin, A. P. & Lim, W. A. Repurposing CRISPR as an RNA-guided platform for sequence-specific control of gene expression. Cell. 152, 1173-1183, doi:10.1016/j.cell.2013.02.022 (2013). PMCID:3664290) tethered to transcriptional repressor domains that promote epigenetic silencing (e.g., KRAB) forms a "CRISPRi" (Gilbert, L. A., Larson, M. H., Morsut, L., Liu, Z., Brar, G. A., Torres, S. E., Stern-Ginossar, N., Brandman, O., Whitehead, E. H., Doudna, J. A., Lim, W. A., Weissman, J. S. & Qi, L. S. CRISPR-mediated modular RNA-guided regulation of transcription in eukaryotes. *Cell*. 154, 442-451, doi:10.1016/j.cell.2013.06.044 (2013). PMCID:3770145; Konermann, S., Brigham, M. D., Trevino, A. E., Hsu, P. D., Heidenreich, M., Cong, L., Platt, R. J., Scott, D. A., Church, G. M. & Zhang, F. Optical control of mammalian endogenous transcription and epigenetic states. *Nature*. 500, 472-476, doi:10.1038/nature12466 (2013). PMCID:3856241) that represses transcription. To use dCas9 as an activator (CRISPRa), a guide RNA may be engineered to carry RNA binding motifs (e.g., MS2) that recruit effector domains fused to RNA-motif binding proteins, increasing transcription (Konermann, S., Brigham, M. D., Trevino, A. E., Joung, J., Abudayyeh, O. O., Barcena, C., Hsu, P. D., Habib, N., Gootenberg, J. S., Nishimasu, H., Nureki, O. & Zhang, F. Genome-scale transcriptional activation by an engineered CRISPR-Cas9 complex. *Nature*. 517, 583-588, doi:10.1038/nature14136 (2015). PMCID:4420636).

CRISPR-Cas systems may also be used for the deletion of regulatory elements. To target non-coding elements, pairs of guides may be designed and used to delete regions of a defined size, and tile deletions covering sets of regions in pools. The delivery of two sgRNAs may mediate efficient excision of 500 bp genomic fragments.

CRISPR-Cas systems may also be used for gene editing, e.g. by RNA-templated homologous recombination. Keskin, H., Shen, Y., Huang, F., Patel, M., Yang, T., Ashley, K., Mazin, A. V. & Storici, F. Transcript-RNA-templated DNA recombination and repair. *Nature*. 515, 436-439, doi: 10.1038/nature13682 (2014).

CRISPR transgenic mice may be used to derive 'CRISPR-ready' cells. 'CRISPR-mice' are mice where the mouse germ line is engineered to harbor key elements of a CRISPR system, and cells require only the programmable (sgRNA) element to activate the CRISPR-Cas system. CRISPR mice include Cas9-transgenic mice (Platt, R. J., Chen, S., Zhou, Y., Yim, M. J., Swiech, L., Kempton, H. R., Dahlman, J. E., Parnas, O., Eisenhaure, T. M., Jovanovic, M., Graham, D. B., Jhunjhunwala, S., Heidenreich, M., Xavier, R. J., Langer, R., Anderson, D. G., Hacohen, N., Regev, A., Feng, G., Sharp, P. A. & Zhang, F. CRISPR-Cas9 knockin mice for genome editing and cancer modeling. *Cell*. 159, 440-455, doi:10.1016/j.cell.2014.09.014 (2014). PMCID:4265475; Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. *Cell* July 15. (2015) 2015 Jul. 30; 162(3): 675-86. doi: 10.1016/j.cell.2015.06.059. Epub 2015 Jul. 16).

CRISPR-Cas based perturbations, including single order or higher order perturbations, may be implemented in pooled format. The perturbation (screen) may be performed with expression readouts or reporter expression readout (genome-wide reporter-based pooled screens).

CRISPR-Cas functional genomics assays that may be used to cause sets of genetic perturbations are discussed in Shalem O., Sanjana N E., Zhang F. High-throughput functional genomics using CRISPR-Cas9. *Nat Rev Genet*. May; 16(5):299-311. (2015). doi: 10.1038/nrg3899. Epub 2015 Apr. 9.

sgRNA libraries, including genome-wide libraries, may be designed as discussed in Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. *Cell* July 15. (2015) 2015 Jul. 30; 162(3):675-86. doi: 10.1016/ j.cell.2015.06.059. Epub 2015 Jul. 16; Sanjana, N. E., Shalem, O. & Zhang, F. Improved vectors and genome-wide libraries for CRISPR screening. *Nat Methods.* 11, 783-784, doi:10.1038/nmeth.3047 (2014); Shalem, O., Sanjana, N. E., Hartenian, E., Shi, X., Scott, D. A., Mikkelsen, T. S., Heckl, D., Ebert, B. L., Root, D. E., Doench, J. G. & Zhang, F. Genome-scale CRISPR-Cas9 knockout screening in human cells. *Science.* 343, 84-87, doi:10.1126/science.1247005 (2014). PMCID:4089965; Shalem, O., Sanjana, N. E. & Zhang, F. High-throughput functional genomics using CRISPR-Cas9. Nat Rev Genet. 16, 299-311, doi:10.1038/nrg3899 (2015).

A pooled genome-wide screen for CRISPR-mediated KO (knock-out) may be performed as in Shalem, O., Sanjana, N. E., Hartenian, E., Shi, X., Scott, D. A., Mikkelsen, T. S., Heckl, D., Ebert, B. L., Root, D. E., Doench, J. G. & Zhang, F. Genome-scale CRISPR-Cas9 knockout screening in human cells. *Science.* 343, 84-87, doi:10.1126/science.1247005 (2014). PMCID:4089965.

An expression marker-based genome-wide CRISPR screen may be performed as in Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. *Cell* July 15. (2015) 2015 Jul. 30; 162(3):675-86. doi: 10.1016/j.cell.2015.06.059. Epub 2015 Jul. 16.

A pooled, genome-scale, CRISPRa screen may be performed as in Konermann, S., Brigham, M. D., Trevino, A. E., Joung, J., Abudayyeh, O. O., Barcena, C., Hsu, P. D., Habib, N., Gootenberg, J. S., Nishimasu, H., Nureki, O. & Zhang, F. Genome-scale transcriptional activation by an engineered CRISPR-Cas9 complex. *Nature.* 517, 583-588, doi:10.1038/nature14136 (2015). PMCID:4420636.

Pooled combinatorial perturbations may be performed, where the delivered perturbations and impact (molecular profiling) are determined post hoc, in either a conventional readout (e.g., sorting followed by sequencing) or with high-content single cell genomics.

In some embodiment, the CRISPR-Cas screen is performed by co-delivering multiple sgRNA using viral vector delivery (eg, sgRNA encoding vectors at a relatively high MOI) into cells pre-expressing the Cas9 enzyme to obtain as many higher order combinations as possible. For small sets of ~5 genes one may generate a combinatorially complete ascertained set of all 32 perturbations.

To detect which perturbations were co-delivered in pooled bins, several strategies are envisioned: (1) Combining two or more guide barcodes using in situ PCR in PEG hydrogel that restricts the diffusion of double stranded DNA; (2) Split-pool tagging of guide barcodes in hydrogels, such that only guides from the same cell are tagged with the same sequence; (3) FISH of expressed guides for imaging readouts. In each case it is possible to use an error-correction scheme in the barcodes.

To detect which perturbations were co-delivered with a single cell genomics readout, it is possible to report the (combinatorial) perturbation in a manner compatible with the full genomic readout. For example one may use an sgRNA vector that also highly expresses a synthetic polyadenylated RNA reporter of the sgRNA barcode. This RNA will be captured along with the cellular mRNA in the transcriptome profiling, eg scRNA-seq (Drop-Seq, see below), or reported by FISH hybridization, such that the same assay ascertains the sgRNAs and their impact on expression (Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. *Cell* July 15. (2015) 2015 Jul. 30; 162(3):675-86. doi: 10.1016/j.cell.2015.06.059. Epub 2015 Jul. 16).

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/

US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to U.S. provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096,324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. *Cell* May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463):472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. *Cell* 159(2): 440-455 DOI: 10.1016/j.cell.2014.09.014 (2014);

Development and Applications of CRISPR-Cas9 for Genome Engineering, Hsu P D, Lander E S, Zhang F., Cell. June 5; 157(6):1262-78 (2014);

Genetic screens in human cells using the CRISPR-Cas9 system, Wang T, Wei J J, Sabatini D M, Lander E S., Science. January 3; 343(6166): 80-84. doi:10.126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015);

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the discussed approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

Useful in the practice of the instant invention, reference is made to the article entitled BCL11A enhancer dissection by Cas9-mediated in situ saturating mutagenesis. Canver, M. C., Smith, E. C., Sher, F., Pinello, L., Sanjana, N. E., Shalem, O., Chen, D. D., Schupp, P. G., Vinjamur, D. S., Garcia, S. P., Luc, S., Kurita, R., Nakamura, Y., Fujiwara, Y., Maeda, T., Yuan, G., Zhang, F., Orkin, S. H., & Bauer, D. E. DOI:10.1038/nature15521, published online Sep. 16, 2015, the article is herein incorporated by reference and discussed briefly below:

Canver et al. describes novel pooled CRISPR-Cas9 guide RNA libraries to perform in situ saturating mutagenesis of the human and mouse BCL11A erythroid enhancers previously identified as an enhancer associated with fetal hemoglobin (HbF) level and whose mouse ortholog is necessary for erythroid BCL11A expression. This approach revealed critical minimal features and discrete vulnerabilities of these enhancers. Through editing of primary human progenitors and mouse transgenesis, the authors validated the BCL11A erythroid enhancer as a target for HbF reinduction. The authors generated a detailed enhancer map that informs therapeutic genome editing.

Reference is made to Zetsche et al., "Cpf1 Is a Single RNA-Guided Endonuclease of a Class 2 CRISPR-Cas System," Cell 163, 1-13 (Oct. 22, 2015) and Shmakov et al., "Discovery and Functional Characterization of Diverse Class 2 CRISPR-Cas Systems," Molecular Cell 60, 1-13 (Available online Oct. 22, 2015). Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications. Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains. Mention is also made of "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), which relates to dimeric RNA-guided FokI Nucleases that recognize extended sequences and can edit endogenous genes with high efficiencies in human cells. In addition, mention is made of PCT application PCT/US14/70057, and BI-2013/107 entitled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of U.S. provisional patent applications: 62/054,490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, with respect to a method of preparing an sgRNA-and-Cas9 protein containing particle comprising admixing a mixture comprising an sgRNA and Cas9 protein (and optionally HDR template) with a mixture comprising or consisting essentially of or consisting of surfactant, phospholipid, biodegradable polymer, lipoprotein and alcohol; and particles from such a process. For example, wherein Cas9 protein and sgRNA were mixed together at a suitable, e.g., 3:1 to 1:3 or 2:1 to 1:2 or 1:1 molar ratio, at a suitable temperature, e.g., 15-30° C., e.g., 20-25° C., e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a C1-6 alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cas9 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP:DMPC:PEG:Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cas9 protein and components that form a particle; as well as particles from such admixing. Aspects of the instant invention can involve particles; for example, particles using a process analogous to that of the Particle Delivery PCT, e.g., by admixing a mixture comprising sgRNA and/or Cas9 as in the instant invention and components that form a particle, e.g., as in the Particle Delivery PCT, to form a particle and particles from such admixing (or, of course, other particles involving sgRNA and/or Cas9 as in the instant invention). These and other CRISPR-Cas or CRISPR systems can be used in the practice of the invention.

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 µg of lentiviral transfer plasmid (pCasES10) and the following packaging plasmids: 5 µg of pMD2.G (VSV-g pseudotype), and 7.5 µg of psPAX2

(gag/pol/rev/tat). Transfection was done in 4 mL OptiMEM with a cationic lipid delivery agent (50 μL Lipofectamine 2000 and 100 μl Plus reagent). After 6 hours, the media was changed to antibiotic-free DMEM with 10% fetal bovine serum.

Lentivirus may be purified as follows. Viral supernatants were harvested after 48 hours. Supernatants were first cleared of debris and filtered through a 0.45 μm low protein binding (PVDF) filter. They were then spun in a ultracentrifuge for 2 hours at 24,000 rpm. Viral pellets were resuspended in 50 μl of DMEM overnight at 4° C. They were then aliquoted and immediately frozen at −80° C.

Other Perturbations

The invention also involves perturbing by subjecting the cell to an increase or decrease in temperature. The temperature may range from about 0° C. to about 100° C., advantageously about 10° C., 15° C., 20° C., 25° C., 30° C., 35° C., 40° C., 45° C., 50° C., 55° C., 60° C., 65° C., 70° C., 75° C., 80° C., 85° C., 90° C., 95° C. or 100° C. In another embodiment, the temperature may be closer to a physiological temperature, e.g., about 30° C., 31° C., 32° C., 33° C., 34° C., 35° C., 36° C., 37° C., 38° C., 39° C. or 40° C.

The invention also involves perturbing by subjecting the cell to a chemical agent. Samples of chemical agents include, but are not limited to, an antibiotic, monoclonal antibody, cancer therapeutic, direct cellular toxin, a small molecule, a hormone, a hormone derivative, a steroid or a steroid derivative.

In one aspect of the invention the perturbing may be with an energy source such as electromagnetic energy or ultrasound. The electromagnetic energy may be a component of visible light having a wavelength in the range of 450 nm-700 nm. In a preferred embodiment the component of visible light may have a wavelength in the range of 450 nm-500 nm and may be blue light. The blue light may have an intensity of at least 0.2 mW/cm$^2$, or more preferably at least 4 mW/cm$^2$. In another embodiment, the component of visible light may have a wavelength in the range of 620-700 nm and is red light.

The invention also involves perturbing by subjecting the cell to a chemical agent and/or temperature gradient. A biomolecular gradient may be formed, for example, as reviewed in Keenan and Folch, Lab Chip. 2008 January; 8(1): doi:10.1039/b711887b. Biomolecule gradients have been shown to play roles in a wide range of biological processes including development, inflammation, wound healing, and cancer metastasis. Elucidation of these phenomena requires the ability to expose cells to biomolecule gradients that are quantifiable, controllable, and mimic those that are present in vivo.

A chemical gradient may be formed without requiring fluid flow (see, e.g., Abhyankar et al., Lab Chip, 2006, 6, 389-393). This device consists of a membrane-covered source region and a large volume sink region connected by a microfluidic channel. The high fluidic resistance of the membrane limits fluid flow caused by pressure differences in the system, but allows diffusive transport of a chemical species through the membrane and into the channel. The large volume sink region at the end of the microfluidic channel helps to maintain spatial and temporal stability of the gradient. The chemical gradient in a 0.5 mm region near the sink region experiences a maximum of 10 percent change between the 6 and 24 h data points. Abhyankar et al., Lab Chip, 2006, 6, 389-393 present the theory, design, and characterization of this device and provide an example of neutrophil chemotaxis as proof of concept for future quantitative cell-signaling applications.

In another embodiment, a gradient may also be introduced with nanowires. In this embodiment, the nanowires do not necessarily introduce a gradient but may introduce other things into the system. A generalized platform for introducing a diverse range of biomolecules into living cells in high-throughput could transform how complex cellular processes are probed and analyzed. Shalek et al., PNAS | Feb. 2, 2010 | vol. 107 | no. 5 demonstrate spatially localized, efficient, and universal delivery of biomolecules into immortalized and primary mammalian cells using surface-modified vertical silicon nanowires. The method relies on the ability of the silicon nanowires to penetrate a cell's membrane and subsequently release surface-bound molecules directly into the cell's cytosol, thus allowing highly efficient delivery of biomolecules without chemical modification or viral packaging. This modality enables one to assess the phenotypic consequences of introducing a broad range of biological effectors (DNAs, RNAs, peptides, proteins, and small molecules) into almost any cell type. Shalek et al., PNAS | Feb. 2, 2010 | vol. 107 | no. 5 show that this platform can be used to guide neuronal progenitor growth with small molecules, knock down transcript levels by delivering siRNAs, inhibit apoptosis using peptides, and introduce targeted proteins to specific organelles. Shalek et al., PNAS | Feb. 2, 2010 | vol. 107 | no. 5 further demonstrate codelivery of siRNAs and proteins on a single substrate in a microarray format, highlighting this technology's potential as a robust, monolithic platform for high-throughput, miniaturized bioassays.

A gradient may be established, for example, in a fluidic device, such as a microfluidic device (see, e.g., Tehranirokh et al., BIOMICROFLUIDICS 7, 051502 (2013)). Microfluidic technology allows dynamic cell culture in microperfusion systems to deliver continuous nutrient supplies for long term cell culture. It offers many opportunities to mimic the cell-cell and cell-extracellular matrix interactions of tissues by creating gradient concentrations of biochemical signals such as growth factors, chemokines, and hormones. Other applications of cell cultivation in microfluidic systems include high resolution cell patterning on a modified substrate with adhesive patterns and the reconstruction of complicated tissue architectures. In the review of Tehranirokh et al., BIOMICROFLUIDICS 7, 051502 (2013), recent advances in microfluidic platforms for cell culturing and proliferation, for both simple monolayer (2D) cell seeding processes and 3D configurations as accurate models of in vivo conditions, are examined.

Drop-Sequence Methods ("Drop-Seq")

Cells come in different types, sub-types and activity states, which are classify based on their shape, location, function, or molecular profiles, such as the set of RNAs that they express. RNA profiling is in principle particularly informative, as cells express thousands of different RNAs. Approaches that measure for example the level of every type of RNA have until recently been applied to "homogenized" samples—in which the contents of all the cells are mixed together. Methods to profile the RNA content of tens and hundreds of thousands of individual human cells have been recently developed, including from brain tissues, quickly and inexpensively. To do so, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from. See, e.g., U.S. 62/048,227 filed Sep. 9, 2014].

Methods of Macosko et al., 2015, Cell 161, 1202-1214 and Klein et al., 2015, Cell 161, 1187-1201 are contemplated for the present invention.

Microfluidics involves micro-scale devices that handle small volumes of fluids. Because microfluidics may accurately and reproducibly control and dispense small fluid volumes, in particular volumes less than 1 µl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets or microwells. The ability to conduct reactions in microdroplets depends on being able to merge different sample fluids and different microdroplets. See, e.g., US Patent Publication No. 20120219947. See also international patent application serial no. PCT/US2014/058637 for disclosure regarding a microfluidic laboratory on a chip.

Droplet/microwell microfluidics offers significant advantages for performing high-throughput screens and sensitive assays. Droplets allow sample volumes to be significantly reduced, leading to concomitant reductions in cost. Manipulation and measurement at kilohertz speeds enable up to 108 discrete biological entities (including, but not limited to, individual cells or organelles) to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

Drop-Sequence methods and apparatus provides a high-throughput single-cell RNA-Seq and/or targeted nucleic acid profiling (for example, sequencing, quantitative reverse transcription polymerase chain reaction, and the like) where the RNAs from different cells are tagged individually, allowing a single library to be created while retaining the cell identity of each read. A combination of molecular barcoding and emulsion-based microfluidics to isolate, lyse, barcode, and prepare nucleic acids from individual cells in high-throughput is used. Microfluidic devices (for example, fabricated in polydimethylsiloxane), sub-nanoliter reverse emulsion droplets. These droplets are used to co-encapsulate nucleic acids with a barcoded capture bead. Each bead, for example, is uniquely barcoded so that each drop and its contents are distinguishable. The nucleic acids may come from any source known in the art, such as for example, those which come from a single cell, a pair of cells, a cellular lysate, or a solution. The cell is lysed as it is encapsulated in the droplet. To load single cells and barcoded beads into these droplets with Poisson statistics, 100,000 to 10 million such beads are needed to barcode ~10,000-100,000 cells.

The invention provides a method for creating a single-cell sequencing library comprising: merging one uniquely barcoded mRNA capture microbead with a single-cell in an emulsion droplet having a diameter of 75-125 µm; lysing the cell to make its RNA accessible for capturing by hybridization onto RNA capture microbead; performing a reverse transcription either inside or outside the emulsion droplet to convert the cell's mRNA to a first strand cDNA that is covalently linked to the mRNA capture microbead; pooling the cDNA-attached microbeads from all cells; and preparing and sequencing a single composite RNA-Seq library.

The invention provides a method for preparing uniquely barcoded mRNA capture microbeads, which has a unique barcode and diameter suitable for microfluidic devices comprising: 1) performing reverse phosphoramidite synthesis on the surface of the bead in a pool-and-split fashion, such that in each cycle of synthesis the beads are split into four reactions with one of the four canonical nucleotides (T, C, G, or A) or unique oligonucleotides of length two or more bases; 2) repeating this process a large number of times, at least two, and optimally more than twelve, such that, in the latter, there are more than 16 million unique barcodes on the surface of each bead in the pool. (See http://www.ncbi.nlm.nih.gov/pmc/articles/PMC206447).

Generally, the invention provides a method for preparing a large number of beads, particles, microbeads, nanoparticles, or the like with unique nucleic acid barcodes comprising performing polynucleotide synthesis on the surface of the beads in a pool-and-split fashion such that in each cycle of synthesis the beads are split into subsets that are subjected to different chemical reactions; and then repeating this split-pool process in two or more cycles, to produce a combinatorially large number of distinct nucleic acid barcodes. Invention further provides performing a polynucleotide synthesis wherein the synthesis may be any type of synthesis known to one of skill in the art for "building" polynucleotide sequences in a step-wise fashion. Examples include, but are not limited to, reverse direction synthesis with phosphoramidite chemistry or forward direction synthesis with phosphoramidite chemistry. Previous and well-known methods synthesize the oligonucleotides separately then "glue" the entire desired sequence onto the bead enzymatically. Applicants present a complexed bead and a novel process for producing these beads where nucleotides are chemically built onto the bead material in a high-throughput manner. Moreover, Applicants generally describe delivering a "packet" of beads which allows one to deliver millions of sequences into separate compartments and then screen all at once.

The invention further provides an apparatus for creating a single-cell sequencing library via a microfluidic system, comprising: a oil-surfactant inlet comprising a filter and a carrier fluid channel, wherein said carrier fluid channel further comprises a resistor; an inlet for an analyte comprising a filter and a carrier fluid channel, wherein said carrier fluid channel further comprises a resistor; an inlet for mRNA capture microbeads and lysis reagent comprising a filter and a carrier fluid channel, wherein said carrier fluid channel further comprises a resistor; said carrier fluid channels have a carrier fluid flowing therein at an adjustable or predetermined flow rate; wherein each said carrier fluid channels merge at a junction; and said junction being connected to a mixer, which contains an outlet for drops.

A mixture comprising a plurality of microbeads adorned with combinations of the following elements: bead-specific oligonucleotide barcodes created by the discussed methods; additional oligonucleotide barcode sequences which vary among the oligonucleotides on an individual bead and can therefore be used to differentiate or help identify those individual oligonucleotide molecules; additional oligonucleotide sequences that create substrates for downstream molecular-biological reactions, such as oligo-dT (for reverse transcription of mature mRNAs), specific sequences (for capturing specific portions of the transcriptome, or priming for DNA polymerases and similar enzymes), or random sequences (for priming throughout the transcriptome or genome). In an embodiment, the individual oligonucleotide molecules on the surface of any individual microbead contain all three of these elements, and the third element includes both oligo-dT and a primer sequence.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'-disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoumarin (Coumaran 151); cyanine dyes; cyanosine; 4',6-diamidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonicacid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colorimetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terylene. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

The invention discussed herein enables high throughput and high resolution delivery of reagents to individual emulsion droplets that may contain cells, organelles, nucleic acids, proteins, etc. through the use of monodisperse aqueous droplets that are generated by a microfluidic device as a water-in-oil emulsion. The droplets are carried in a flowing oil phase and stabilized by a surfactant. In one aspect single cells or single organelles single molecules (proteins, RNA, DNA) are encapsulated into uniform droplets from an aqueous solution/dispersion. In a related aspect, multiple cells or multiple molecules may take the place of single cells or single molecules. The aqueous droplets of volume ranging from 1 pL to 10 nL work as individual reactors. Disclosed embodiments provide $10^4$ to $10^5$ single cells in droplets which can be processed and analyzed in a single run.

To utilize microdroplets for rapid large-scale chemical screening or complex biological library identification, different species of microdroplets, each containing the specific chemical compounds or biological probes cells or molecular barcodes of interest, have to be generated and combined at the preferred conditions, e.g., mixing ratio, concentration, and order of combination.

Each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets.

Fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. In another embodiment, the expansion and/or contraction of the liquid reservoir may be combined with other flow-controlling devices and methods, e.g., as discussed herein. Non-limiting examples of devices able to cause the expansion and/or contraction of a liquid reservoir include pistons.

Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the oil that is used as the continuous phase for the emulsion library. Surfactant molecules are amphiphilic-part of the molecule is oil soluble, and part of the molecule is water soluble. When a water-oil interface is formed at the nozzle of a microfluidic chip for example in the inlet module discussed herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A droplet library may be made up of a number of library elements that are pooled together in a single collection (see, e.g., US Patent Publication No. 2010002241). Libraries may vary in complexity from a single library element to 1015 library elements or more. Each library element may be one or more given components at a fixed concentration. The element may be, but is not limited to, cells, organelles, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

A cell library element may include, but is not limited to, hybridomas, B-cells, primary cells, cultured cell lines, cancer cells, stem cells, cells obtained from tissue, or any other cell type. Cellular library elements are prepared by encapsulating a number of cells from one to hundreds of thousands in individual droplets. The number of cells encapsulated is usually given by Poisson statistics from the number density of cells and volume of the droplet. However, in some cases the number deviates from Poisson statistics as discussed in Edd et al., "Controlled encapsulation of single-cells into monodisperse picolitre drops." Lab Chip, 8(8): 1262-1264, 2008. The discrete nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element.

A bead based library element may contain one or more beads, of a given type and may also contain other reagents, such as antibodies, enzymes or other proteins. In the case where all library elements contain different types of beads, but the same surrounding media, the library elements may all be prepared from a single starting fluid or have a variety of starting fluids. In the case of cellular libraries prepared in mass from a collection of variants, such as genomically modified, yeast or bacteria cells, the library elements will be prepared from a variety of starting fluids.

Often it is desirable to have exactly one cell per droplet with only a few droplets containing more than one cell when starting with a plurality of cells or yeast or bacteria, engineered to produce variants on a protein. In some cases, variations from Poisson statistics may be achieved to provide an enhanced loading of droplets such that there are more droplets with exactly one cell per droplet and few exceptions of empty droplets or droplets containing more than one cell.

Examples of droplet libraries are collections of droplets that have different contents, ranging from beads, cells, small molecules, DNA, primers, antibodies. Smaller droplets may be in the order of femtoliter (fL) volume drops, which are especially contemplated with the droplet dispenser. The volume may range from about 5 to about 600 fL. The larger droplets range in size from roughly 0.5 micron to 500 micron in diameter, which corresponds to about 1 pico liter to 1 nano liter. However, droplets may be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the emulsion libraries of the present invention may be contained within an immiscible oil which may comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays discussed herein. Fluids (e.g., aqueous fluids, immiscible oils, etc.) and other surfactants that may be utilized in the droplet libraries of the present invention are discussed in greater detail herein.

The present invention provides an emulsion library which may comprise a plurality of aqueous droplets within an immiscible oil (e.g., fluorocarbon oil) which may comprise at least one fluorosurfactant, wherein each droplet is uniform in size and may comprise the same aqueous fluid and may comprise a different library element. The present invention also provides a method for forming the emulsion library which may comprise providing a single aqueous fluid which may comprise different library elements, encapsulating each library element into an aqueous droplet within an immiscible fluorocarbon oil which may comprise at least one fluorosurfactant, wherein each droplet is uniform in size and may comprise the same aqueous fluid and may comprise a different library element, and pooling the aqueous droplets within an immiscible fluorocarbon oil which may comprise at least one fluorosurfactant, thereby forming an emulsion library.

For example, in one type of emulsion library, all different types of elements (e.g., cells or beads), may be pooled in a single source contained in the same medium. After the initial pooling, the cells or beads are then encapsulated in droplets to generate a library of droplets wherein each droplet with a different type of bead or cell is a different library element. The dilution of the initial solution enables the encapsulation process. In some embodiments, the droplets formed will either contain a single cell or bead or will not contain anything, i.e., be empty. In other embodiments, the droplets formed will contain multiple copies of a library element. The cells or beads being encapsulated are generally variants on the same type of cell or bead. In one example, the cells may comprise cancer cells of a tissue biopsy, and each cell type is encapsulated to be screened for genomic data or against different drug therapies. Another example is that 1011 or 1015 different type of bacteria; each having a different plasmid spliced therein, are encapsulated. One example is a bacterial library where each library element grows into a clonal population that secretes a variant on an enzyme.

In another example, the emulsion library may comprise a plurality of aqueous droplets within an immiscible fluorocarbon oil, wherein a single molecule may be encapsulated, such that there is a single molecule contained within a droplet for every 20-60 droplets produced (e.g., 20, 25, 30, 35, 40, 45, 50, 55, 60 droplets, or any integer in between). Single molecules may be encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 μm droplets were made at 10 kHz per second. Formation of these libraries rely on limiting dilutions.

Methods of the invention involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41, 780) and European publication number EP2047910 to Raindance Technologies Inc. The content of each of which is incorporated by reference herein in its entirety.

In certain embodiments, the carrier fluid may contain one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be surrounded by a surfactant which stabilizes the droplets by reducing the surface tension at the aqueous oil interface. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

By incorporating a plurality of unique tags into the additional droplets and joining the tags to a solid support designed to be specific to the primary droplet, the conditions that the primary droplet is exposed to may be encoded and recorded. For example, nucleic acid tags can be sequentially ligated to create a sequence reflecting conditions and order of same. Alternatively, the tags can be added independently appended to solid support. Non-limiting examples of a dynamic labeling system that may be used to bioinformatically record information can be found at U.S. Provisional Patent Application entitled "Compositions and Methods for Unique Labeling of Agents" filed Sep. 21, 2012 and Nov. 29, 2012. In this way, two or more droplets may be exposed to a variety of different conditions, where each time a droplet is exposed to a condition, a nucleic acid encoding the condition is added to the droplet each ligated together or to a unique solid support associated with the droplet such that, even if the droplets with different histories are later combined, the conditions of each of the droplets are remain available through the different nucleic acids. Non-limiting examples of methods to evaluate response to exposure to a plurality of conditions can be found at U.S. Provisional Patent Application entitled "Systems and Methods for Droplet Tagging" filed Sep. 21, 2012.

Applications of the disclosed device may include use for the dynamic generation of molecular barcodes (e.g., DNA oligonucleotides, fluorophores, etc.) either independent from or in concert with the controlled delivery of various compounds of interest (drugs, small molecules, siRNA, CRISPR guide RNAs, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques of the disclosed invention facilitate efforts to perform studies that require data resolution at the single cell (or single molecule) level and in a cost effective manner. Disclosed embodiments provide a high throughput and high resolution delivery of reagents to individual emulsion droplets that may contain cells, nucleic acids, proteins, etc. through the use of monodisperse aqueous droplets that are generated one by one in a microfluidic chip as a water-in-oil emulsion. Hence, the invention proves advantageous over prior art systems by being able to dynamically track individual cells and droplet treatments/combinations during life cycle experiments. Additional advantages of the disclosed invention provides an ability to create a library of emulsion droplets on demand with the further capability of manipulating the droplets through the disclosed process(es). Disclosed embodiments may, thereby, provide dynamic tracking of the droplets and create a history of droplet deployment and application in a single cell based environment.

Droplet generation and deployment is produced via a dynamic indexing strategy and in a controlled fashion in accordance with disclosed embodiments of the present invention. Disclosed embodiments of the microfluidic device discussed herein provides the capability of microdroplets that be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays.

Well-Based Biological Analysis ("Seq-Well")

The well-based biological analysis platform, also referred to as Seq-well, facilitates the creation of barcoded single-cell sequencing libraries from thousands of single cells using a device that contains 100,000 40-micron wells. Importantly, single beads can be loaded into each microwell with a low frequency of duplicates due to size exclusion (average bead diameter 35 µm). By using a microwell array, loading efficiency is greatly increased compared to drop-seq, which requires poisson loading of beads to avoid duplication at the expense of increased cell input requirements. Seq-well, however, is capable of capturing nearly 100% of cells applied to the surface of the device.

Seq-well is a methodology which allows attachment of a porous membrane to a container in conditions which are benign to living cells. Combined with arrays of picoliter-scale volume containers made, for example, in PDMS, the platform provides the creation of hundreds of thousands of isolated dialysis chambers which can be used for many different applications. The platform also provides single cell lysis procedures for single cell RNA-seq, whole genome amplification or proteome capture; highly multiplexed single cell nucleic acid preparation (~100× increase over current approaches); highly parallel growth of clonal bacterial populations thus providing synthetic biology applications as well as basic recombinant protein expression; selection of bacterial that have increased secretion of a recombinant product possible product could also be small molecule metabolite which could have considerable utility in chemical industry and biofuels; retention of cells during multiple microengraving events'; long term capture of secreted products from single cells; and screening of cellular events. Principles of the present methodology allow for addition and subtraction of materials from the containers, which has not previously been available on the present scale in other modalities.

Seq-Well also enables stable attachment (through multiple established chemistries) of porous membranes to PDMS nanowell devices in conditions that do not affect cells. Based on requirements for downstream assays, amines are functionalized to the PDMS device and oxidized to the membrane with plasma. With regard to general cell culture uses, the PDMS is amine functionalized by air plasma treatment followed by submersion in an aqueous solution of poly (lysine) followed by baking at 80° C. For processes that require robust denaturing conditions, the amine must be covalently linked to the surface. This is accomplished by treating the PDMS with air plasma, followed by submersion in an ethanol solution of amine-silane, followed by baking at 80° C., followed by submersion in 0.2% phenylene diisothiocyanate (PDITC) DMF/pyridine solution, followed by baking, followed by submersion in chitosan or poly (lysine) solution. For functionalization of the membrane for protein capture, membrane can be amine-silanized using vapor deposition and then treated in solution with NHS-biotin or NHS-maleimide to turn the amine groups into the crosslinking species.

After functionalization, the devices is loaded with cells (bacterial, mammalian or yeast) in compatible buffers. The cell laden device is then brought in contact with the functionalized membrane using a clamping device. A plain glass slide is placed on top of the membrane in the clamp to provide force for bringing the two surfaces together. After an hour incubation, as one hour is a preferred time span, the clamp is opened and the glass slide is removed. The device can then be submerged in any aqueous buffer for days without the membrane detaching, enabling repetitive measurements of the cells without any cell loss. The covalently-linked membrane is stable in many harsh buffers including guanidine hydrochloride which can be used to robustly lyse cells. If the pore size of the membrane is small, the products from the lysed cells will be retained in each well. The lysing buffer can be washed out and replaced with a different buffer which allows binding of biomolecules to probes preloaded in the wells. The membrane can then be removed, enabling addition of enzymes to reverse transcribe or amplify nucleic acids captured in the wells after lysis. Importantly, the chemistry enables removal of one membrane and replacement with a membrane with a different pore size to enable integration of multiple activities on the same array.

As discussed, while the platform has been optimized for the generation of individually barcoded single-cell sequencing libraries following confinement of cells and mRNA capture beads (Macosko, et al. 2015), it is capable of multiple levels of data acquisition. The platform is compatible with other assays and measurements performed with the same array. For example, profiling of human antibody responses by integrated single-cell analysis is discussed with regard to measuring levels of cell surface proteins (Ogunniyi, A. O., B. A. Thomas, T. J. Politano, N. Varadarajan, E. Landais, P. Poignard, B. D. Walker, D. S. Kwon, and J. C. Love, "Profiling Human Antibody Responses by Integrated Single-Cell Analysis" Vaccine, 32(24), 2866-2873.) The authors demonstrate a complete characterization of the antigen-specific B cells induced during infections or following vaccination, which enables and informs one of skill in the art how interventions shape protective humoral responses. Specifically, this disclosure combines single-cell profiling with on-chip image cytometry, microengraving, and single-cell RT-PCR.

Undersampling—A Sampling Based Framework for Genetic Interactions

According to the invention, random sampling may comprise matrix completion, tensor completion, compressed sensing, or kernel learning.

In some aspects, where random sampling comprises matrix completion, tensor completion, or compressed sensing, a may be of the order of log P.

The invention relies on a random sampling assumption, e.g. that the combinatorial space is sparse and/or of low rank. This assumption is generic and advantageously does not rely on the pre-determination of a (known) set of genetic interactions. This assumption constrains the range or complexity of models, and thus can be used to restrict sampling size (undersampling). Further, as detailed below, the invention relies on the following:: (1) Given a limited number of assays, if one wishes to infer interactions up to an order j, it is advantageous to randomly sample interactions at a higher order k>j, because higher order perturbations maximize the information that can be recovered; and (2) in such a method, one may use a model that accounts for higher order interactions when analyzing lower order ones. For example, it is possible to aim for each perturbation to target k~5-7 genes at once to estimate/model interactions at lower order j~3-5.

Although some experimental methods open the way to test non-linear interactions by high order combinatorial genetic perturbations, exhaustive combinatorial exploration is intractable for anything but 2- or 3-way interactions for a few genes.

According to the invention, random matrix theory and compressive sensing may be used to re-formulate this as a random sampling problem, developing a new framework from experimental design to model inference, testing and refinement.

To infer combinatorial models from a dramatic undersampling of the full high-order combinatorial space with massively combinatorial molecular perturbations (MCPP), one may rely on random matrix theory, compressive sensing and kernel learning.

According to the invention, it is made possible to model non-linear regulatory functions from genetic manipulations (perturbations).

One may learn models of higher-order genetic interactions from combinatorial perturbations with single cell profiling. Although the learning problem is underdetermined due to combinatorial explosion ($2^m$ possible interaction terms among m genes), it can become tractable in the presence of additional structure, including sparsity and smoothness, that constrains the range or complexity of models. One may thus rely on the following: (1) Given a limited number of assays, if one wishes to infer interactions up to an order j, it is advantageous to randomly sample interactions at a higher order k>j, because higher order perturbations maximize the information that can be recovered; and (2) in such a design, one can use a model that accounts for higher order interactions when analyzing lower order ones. One may for example aim for each perturbation to target k~5-7 genes at once to estimate interactions at j~3-5.

Thus the present invention relies on a learning approach that takes multiplex perturbations at a high order n and a complex readout data (e.g., RNA profile) and infers a model of genetic interactions at a lower order (m<n), as well as strategies for experimental design, model testing and refinement.

If one assumes that genetic interactions are low rank, sparse, or both, then the true number of degrees of freedom is small relative to the complete combinatorial expansion, so that one can infer the full nonlinear landscape with a relatively small random sampling of high-order perturbations, without specific knowledge of which genes are likely to interact. Analysis of prior studies supports the sparsity assumption in yeast (for fitness: Costanzo, M., Baryshnikova, A., Bellay, J., Kim, Y., Spear, E. D., Sevier, C. S., Ding, H., Koh, J. L., Toufighi, K., Mostafavi, S., Prinz, J., St Onge, R. P., VanderSluis, B., Makhnevych, T., Vizeacoumar, F. J., Alizadeh, S., Bahr, S., Brost, R. L., Chen, Y., Cokol, M., Deshpande, R., Li, Z., Lin, Z. Y., Liang, W., Marback, M., Paw, J., San Luis, B. J., Shuteriqi, E., Tong, A. H., van Dyk, N., Wallace, I. M., Whitney, J. A., Weirauch, M. T., Zhong, G., Zhu, H., Houry, W. A., Brudno, M., Ragibizadeh, S., Papp, B., Pal, C., Roth, F. P., Giaever, G., Nislow, C., Troyanskaya, O. G., Bussey, H., Bader, G. D., Gingras, A. C., Morris, Q. D., Kim, P. M., Kaiser, C. A., Myers, C. L., Andrews, B. J. & Boone, C. The genetic landscape of a cell. *Science*. 327, 425-431, doi:10.1126/science.1180823 (2010)), and fly (for 11 imaging phenotypes: Laufer, C., Fischer, B., Billmann, M., Huber, W. & Boutros, M. Mapping genetic interactions in human cancer cells with RNAi and multiparametric phenotyping. *Nat Methods*. 10, 427-431, doi:10.1038/nmeth.2436 (2013)), and to the limited tested extent, mammals (for 60 genes: Bassik, M. C., Kampmann, M., Lebbink, R. J., Wang, S., Hein, M. Y., Poser, I., Weibezahn, J., Horlbeck, M. A., Chen, S., Mann, M., Hyman, A. A., Leproust, E. M., McManus, M. T. & Weissman, J. S. A systematic mammalian genetic interaction map reveals pathways underlying ricin susceptibility. *Cell*. 152, 909-922, doi:10.1016/j.cell.2013.01.030 (2013). PMCID:3652613).

Matrix (Tensor) Completion.

All the values of a matrix (tensor) are filled in using a small collection of sampled entries. Applicants hypothesize that the rank of a tensor of higher-order interactions is a fraction of the number of tested genes which is tested by calculating the rank from a dense sampling of second or third order knockouts from a small collection of genes. If the rank of interactions is limited, then Applicants randomly sample sets of genes to knockout from a larger collection, and fill in the remaining values via nuclear norm regularized least-squares optimization (Candes, E. J. & Plan, Y. Matrix Completion With Noise. *Proceedings of the IEEE*. 98, 925-936, doi:Doi 10.1109/Jproc.2009.2035722 (2010)). Provable guarantees suggest that if the rank, r, is small relative to the number of genes, n, then $m \geq O(n^{6/5} r \log n)$ sampled entries are sufficient. However, since these guarantees assume rough uniformity in the loadings of interaction singular vectors, this assumption is unlikely to hold if the interaction matrix is very sparse. In this case, Applicants perform the same random sampling, and simultaneously regularize over both the nuclear norm and the L1 norm of the matrix (Richard, E., Savalle, P. & Vayatis, N. Estimation of Simultaneously Sparse and Low Rank Matrices. arXiv. doi:arXiv:1206.6474).

Compressed Sensing

Here, instead of working with a tensor of interaction terms, Applicants work with a basis that spans all higher order interactions. Each single quantitative phenotype is a real-valued function $f(g)$ on possible genotypes g (the $2^m$ possible allelic or knockout states), represented as binary strings of length m. Applicants analyze such Boolean functions using *Fourier decomposition* (O'Donnell, R. *Analysis of boolean functions*. (Cambridge University Press, 2014))

$$f(g) = \sum_{b \in \{0,1\}^m} \hat{f}_b (-1)^{b \cdot g}, \hat{f}_b = \frac{1}{2^m} \sum_{g \in \{0,1\}^m} f(g)(-1)^{g \cdot b},$$

where $f$ is an orthogonal basis indexed by binary strings b, and each Fourier coefficient $\hat{f}_b$ precisely quantifies the effect of one possible multi-gene interaction. For example with m=2, $\hat{f}_{00}$ is the average phenotype; $\hat{f}_{10}$ is the effect of the first gene KO, marginalized over the genetic background of the second; similarly for $\hat{f}_{01}$; and $\hat{f}_{11}$ quantifies the two-way interaction (the extent to which the double KO phenotype differs from that predicted by the sum of the effects of the single KOs). Applicants hypothesize that such genotype-phenotype maps are approximately sparse in the Fourier basis, such that there is a small number, s, of nonzero Fourier coefficients (not known a priori). With perturbations generated only up to a limited order, Applicants obtain a truncated Fourier model, which is a general linear model: the genetic interactions are in the basis functions (encoded into a design matrix), and the response is linear in the unknown Fourier coefficients. Applicants assume most truncated coefficients are negligible. Assuming that the genotype-phenotype maps are approximately sparse in the Fourier basis, Applicants use L1-penalized regression to learn the coefficients of the map from paired genotype-phenotype observations $g_i, f(g_i)$ (with uncertainty or noise in both).

Compressed sensing posits that if Applicants' perturbations are de-coherent under the given basis, then exact recovery is possible with dramatic under-sampling (in the noiseless case) (Candes, E. Compressive sampling. *Proceedings of the International Congress of Mathematicians Madrid*, Aug. 22-30, 2006. 3, 19, doi:10.4171/022 (2006)), such that a sample size n=C s log p will suffice, where s is the number of effectively nonzero coefficients, p is the magnitude of combinatorial expansion and C depends on noise and experimental design (how the $g_i$ are sampled) (Candes, E. Mathematics of sparsity (and few other things). *ICM 2014 Proceedings, to appear*. (2014)). By varying the penalization parameter, Applicants learn sparse structures at different levels of thresholding, and find the level below which the data become insufficient to capture the signal (Hastie, T., Friedman, J. & Tibshirani, R. *The elements of statistical learning*. Vol. 2 (Springer, 2009)). Applicants explore using a larger penalization parameter on the higher order interaction coefficients, and, with good estimates of single perturbations, even no penalty on the linear terms, or regressing those out first. If each experiment is a Poisson random sampling of KOs, Applicants expect the measurements to have good de-coherence under the Fourier basis, provided the mean number of KO experiments per gene is not too low. If Applicants' assumptions are correct, a soft phase transition in performance as the number of observations crosses a threshold should be observed. Applicants use a small complete dataset or downsampling of a larger more random dataset, to assess if the appropriate transition is observed.

Kernel Learning.

If there is no strict sparsity in the rank or in the coefficients, Applicants build predictive functions of the effects of combinatorial perturbations, using a kernel of experimental similarity. Given m experiments, Applicants define an m×m polynomial kernel, for example, based on the overlap in knockouts between any pair of experiments. Applicants learn a weighted combination of kernel vectors that fits a collection of training data, and use the coefficients to predict the outcome of new experiments. Here, the density of nonlinear interaction terms can be much greater, since Applicants do not directly learn any particular interaction coefficient, but rather a kernelized version of the entire polynomial. Indeed, if the interaction terms are too sparse, kernel learning is unlikely to be successful with undersampling.

Applicants analyzed 3-way interaction data measured by overexpression of every 3-way combination of 39 miRNAs and a phenotype of drug resistance, and confirmed substantial sparsity in the data. Applicants analyzed the 5-way interactions affecting expression profiles in response to salt in yeast between the MAPK Hog1 (p38 ortholog) and 4 TFs (1, 2, 3, 4, and 5 KO: 32 perturbations). Using a (non-regularized) linear model, Applicants quantified 1- and 2-way interactions, finding diverse non-linearities.

Analyzing a Cell Population at the Single Cell Level

The method according to the invention may comprise a step for single-cell molecular profiling. In some embodiments the step may comprise processing said cell population in order to physically separate cells. In some embodiments the step may comprise single-cell manipulation, e.g. using microfluidics based techniques. In some embodiments the step may comprise reverse emulsion droplet-based single-cell analysis or hydrogel droplet-based single-cell analysis.

The method of the invention may use microfluidics, e.g. to culture cells in specific combinations, control the spatiotemporal signals they receive, and/or trace and sample them as desired.

Molecular Profiling at the Single Cell Level

The method according to the invention may comprise a step for single-cell molecular profiling. This step may involve analyzing biomolecules quantitatively or semi-quantitatively. The biomolecules may include RNA, mRNA, pre-mRNA, proteins, peptides, chromatin or DNA. Said analysis may be performed genome-wide. Said analysis may be coupled (dual or sequential analysis of two or more types of biomolecules).

In some embodiments the step may comprise single-cell genomic profiling, single-cell RNA profiling, single-cell DNA profiling, single-cell epigenomic profiling, single-cell protein profiling, or single-cell reporter gene expression profiling. Proteins that may be used to alter genomic and epigenomic state are discussed in Shmakov et al., 2015, Molecular Cell 60, 1-13 and Zetsche et al., 2015, Cell 163, 759-771.

In some embodiments the step may comprise single-cell RNA abundance analysis, single-cell transcriptome analysis, single-cell exome analysis, single-cell transcription rate analysis, or single-cell RNA degradation rate analysis.

In some embodiments the step may comprise single-cell DNA abundance analysis, single-cell DNA methylation profiling, single-cell chromatin profiling, single-cell chromatin accessibility profiling, single-cell histone modification profiling, or single-cell chromatin indexing.

In some embodiments the step may comprise single-cell protein abundance analysis, single-cell post-translational protein modification analysis, or single-cell proteome analysis.

In some embodiments the step may comprise single-cell mRNA reporter analysis, detection or quantification.

In some embodiments the step may comprise single-cell dual molecular profiling, such any combination of two amongst single-cell RNA profiling, single-cell DNA profiling, single-cell protein profiling, mRNA reporter analysis.

The method of the invention may include at the step determining single cell RNA levels. For single cell RNA-Seq (scRNA-Seq), one may use Drop-Seq (Macosko, E. Z., Basu, A., Satija, R., Nemesh, J., Goldman, M., Tirosh, I., Bialas, A. R., Kamitaki, N., Sanes, J. R., Weitz, D. A., Shalek, A. K., Regev, A. & McCarroll, S. A. Highly Parallel Genome-wide Expression Profiling of Individual Cells Using Nanoliter Droplets. Cell. 2015 May 21; 161(5):1202-14. doi: 10.1016/j.cell.2015.05.002. PMCID:4481139) and variants thereof. This technique relies on reverse-emulsion, early barcoding for analyzing $10^4$-$10^6$ cells/experiment at very low cost. Drop-Seq enables to co-encapsulate individual cells with uniquely barcoded mRNA capture beads in reverse emulsion droplets. After lysis and mRNA capture, the emulsion is broken and all beads/cells are processed (RT, library prep) together, deconvolving each cell's profile from bead barcodes. In some embodiments, droplets can compartmentalize hundreds of cells/sec, are stable over time and to heat, and can serve as micro-vessels to add reagents; after RT, barcoded beads are stable and can be sorted or subselected. Sampling noise from shallow read depth is substantially lower than the technical variability between cells (Shalek, A. K., Satija, R., Shuga, J., Trombetta, J. J., Gennert, D., Lu, D., Chen, P., Gertner, R. S., Gaublomme, J. T., Yosef, N., Schwartz, S., Fowler, B., Weaver, S., Wang, J., Wang, X., Ding, R., Raychowdhury, R., Friedman, N., Hacohen, N., Park, H., May, A. P. & Regev, A. Single-cell RNA-seq reveals dynamic paracrine control of cellular variation. Nature. 510, 363-369, doi:10.1038/nature13437 (2014). PMCID:4193940.), so one may sufficiently estimate expression with ~100,000 reads per cell for many applications (especially with a 5' or 3'-end protocol, Satija, R., Farrell, J. A., Gennert, D., Schier, A. F. & Regev, A. Spatial reconstruction of single-cell gene expression data. Nature biotechnology. 33, 495-502, doi:10.1038/nbt.3192 (2015)).

Single cell RNA may also be analyzed as discussed in Klein, A. M., Mazutis, L., Akartuna, I., Tallapragada, N., Veres, A., Li, V., Peshkin, L., Weitz, D. A., Kirschner, M. W. Droplet barcoding for single-cell transcriptomics applied to embryonic stem cells. Cell. 2015 May 21; 161(5):1187-201. doi: 10.1016/j.cell.2015.04.044. PMCID: 4441768.

The method of the invention may include determining RNA transcription and degradation rates. One may use RNA metabolically labeled with 4-thiouridine, to measure RNA transcription and degradation rates (Rabani, M., Raychowdhury, R., Jovanovic, M., Rooney, M., Stumpo, D. J., Pauli, A., Hacohen, N., Schier, A. F., Blackshear, P. J., Friedman, N., Amit, I. & Regev, A. High-resolution sequencing and modeling identifies distinct dynamic RNA regulatory strategies. Cell. 159, 1698-1710, doi:10.1016/j.cell.2014.11.015 (2014). PMCID:4272607; Rabani, M., Levin, J. Z., Fan, L., Adiconis, X., Raychowdhury, R., Garber, M., Gnirke, A., Nusbaum, C., Hacohen, N., Friedman, N., Amit, I. & Regev, A. Metabolic labeling of RNA uncovers principles of RNA production and degradation dynamics in mammalian cells. Nature biotechnology. 29, 436-442, doi:10.1038/nbt.1861 (2011). PMCID:3114636).

The method of the invention may include a step of determining DNA methylation. One may apply methods for reduced representation bisulfite sequencing (RRBS), targeted capture, and whole genome bisulfite sequencing of DNA methylation from bulk to ultra-low inputs (Chan, M. M., Smith, Z. D., Egli, D., Regev, A. & Meissner, A. Mouse ooplasm confers context-specific reprogramming capacity. Nature genetics. 44, 978-980, doi:10.1038/ng.2382 (2012).

PMCID:3432711; Smith, Z. D., Chan, M. M., Humm, K. C., Karnik, R., Mekhoubad, S., Regev, A., Eggan, K. & Meissner, A. DNA methylation dynamics of the human preimplantation embryo. Nature. 511, 611-615, doi:10.1038/nature13581 (2014). PMCID:4178976; Smith, Z. D., Chan, M. M., Mikkelsen, T. S., Gu, H., Gnirke, A., Regev, A. & Meissner, A. A unique regulatory phase of DNA methylation in the early mammalian embryo. Nature. 484, 339-344, doi:10.1038/nature10960 (2012). PMCID:3331945) to single cells.

The method of the invention may include a step determining Chromatin accessibility. This may be performed by ATAC-Seq. For massively parallel single cell ATAC-Seq one may implement a droplet-based assay. First, in-tube, one may use Tn5 transposase to fragment chromatin inside isolated intact nuclei and add universal primers at cutting sites. Next, in-drop, one may use a high diversity library of barcoded primers to uniquely tag all DNA that originated from the same single cell. Alternatively, one may perform all steps in drop. One may also use a strategy that relies on split pooled nuclei barcoding in plates (Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237): 910-4. doi: 10.1126/science.aab1601. Epub 2015 May 7). Applicants have optimized key steps in a mixture of human and mouse cells, with specificity that exceeds the initial performance of mRNA Drop-Seq. Applicants have also used a Fluidigm C1 protocol (see https://www.fluidigm.com/products/c1-system) to analyze ~100 single DCs, closely reproducing ensemble measures, high enrichment in TSSs, and nucleosome-like periodicity.

ATAC-seq (assay for transposase-accessible chromatin) identifies regions of open chromatin using a hyperactive prokaryotic Tn5-transposase, which preferentially inserts into accessible chromatin and tags the sites with sequencing adaptors [Pott and Lieb Genome Biology (2015) 16:172 DOI 10.1186/s13059-015-0737-7 and Buenrostro J D, Giresi P G, Zaba L C, Chang H Y, Greenleaf W J. Transposition of native chromatin for fast and sensitive epigenomic profiling of open chromatin, DNA-binding proteins and nucleosome position. Nat Methods. 2013; 10:1213-128]. Two very different approaches were used: one relied on physical isolation of single cells [Buenrostro J D, Wu B, Litzenburger U M, Ruff D, Gonzales M L, Snyder M P, et al. Single-cell chromatin accessibility reveals principles of regulatory variation. Nature. 2015; 523:486-90], and the other avoided single-cell reaction volumes by using a two-step combinatorial indexing strategy [Cusanovich D A, Daza R, Adey A, Pliner H A, Christiansen L, Gunderson K L, et al. Epigenetics. Multiplex single-cell profiling of chromatin accessibility by combinatorial cellular indexing. Science. 2015; 348:910-4].

In the indexing scheme, Cusanovich et al. [Cusanovich D A, Daza R, Adey A, Pliner H A, Christiansen L, Gunderson K L, et al. Epigenetics. Multiplex single-cell profiling of chromatin accessibility by combinatorial cellular indexing. Science. 2015; 348:910-4] lysed cells, and 2500 nuclei were placed into each well of a 96-well plate. Transposases loaded with unique adaptors were added to each well, creating 96 pools of approximately 2500 nuclei, each pool with distinct barcodes. Nuclei from all of the transposition reactions were mixed, and using a fluorescence-activated cell sorter (FACS) 15-25 nuclei were deposited into each well of a second 96-well plate. Nuclei in each well of this second plate were lysed, and the DNA was amplified using a primer containing a second barcode. The low number of nuclei per well ensured that about 90% of the resulting barcode combinations were unique to a single cell. This combinatorial indexing strategy enabled the recovery of 500-1500 cells with unique tags per experiment. Overall Cusanovich et al. obtained scATAC-seq data from over 15,000 individual cells from mixtures of GM12878 lymphoblastoid cells with HEK293, HL-60, or mouse Patski cells. The number of reads associated with any single cell was very low, varying from 500 to about 70,000 with a median of fewer than 3000 reads per cell.

Buenrostro et al. (Buenrostro J D, Wu B, Litzenburger U M, Ruff D, Gonzales M L, Snyder M P, et al. Single-cell chromatin accessibility reveals principles of regulatory variation. Nature. 2015; 523:486-90) used a programmable microfluidic device (C1, Fluidigm) to isolate single cells and perform ATAC-seq on them in nanoliter reaction chambers. Each nanochamber was analyzed under a microscope to ensure that a single viable cell had been captured. This approach is simple and has the significant advantage of a carefully monitored reaction environment for each individual cell, although the throughput was limited to processing 96 cells in parallel. Buenrostro et al. sampled 1632 cells from eight different cell lines, including GM12878, K562, and H1 cells, and obtained an average of 73,000 reads per cell, about 20 times the number of reads per cell obtained using the combinatorial barcoding strategy.

The method of the invention may include a step of determining histone modifications and protein-DNA interactions. One may apply tools that use genomic barcoding to index chromatin prior to immunoprecipitation to enable multiplexed analysis of limited samples and individual cells in a single reaction. For single-cell chromatin profiling, one may use Drop-ChIP where the chromatin of individual cells is barcoded in droplets. Based on the Drop-Seq technique, one may encapsulate single cells, lyse and MNase-digest chromatin, then fuse a second droplet with barcoded oligos, ligate them to the fragmented chromatin, break the emulsion, add carrier chromatin, and carry out ChIP-Seq. this may be performed using a protocol with split-pool barcoding to collect $10^4$-$10^5$ single cells/assay.

ChIP-sequencing, also known as ChIP-seq, is a method used to analyze protein interactions with DNA which may be used with perturbation. ChIP-seq combines chromatin immunoprecipitation (ChIP) with massively parallel DNA sequencing to identify the binding sites of DNA-associated proteins. It can be used to map global binding sites precisely for any protein of interest. ChIP-seq is used primarily to determine how transcription factors and other chromatin-associated proteins influence phenotype-affecting mechanisms. Determining how proteins interact with DNA to regulate gene expression is important for understanding many biological processes and disease states. This epigenetic information is complementary to genotype and expression analysis. ChIP-seq technology is as an alternative to ChIP-chip which requires a hybridization array. Specific DNA sites in direct physical interaction with transcription factors and other proteins can be isolated by chromatin immunoprecipitation. ChIP produces a library of target DNA sites bound to a protein of interest in vivo. Massively parallel sequence analyses are used in conjunction with whole-genome sequence databases to analyze the interaction pattern of any protein with DNA, see, e.g., Johnson D S, Mortazavi A et al. (2007) Genome-wide mapping of in vivo protein-DNA interactions. Science 316: 1497-1502, or the pattern of any epigenetic chromatin modifications. This can be applied to the set of ChIP-able proteins and modifications, such as transcription factors, polymerases and transcriptional machinery, structural proteins, protein modifications, and DNA modifications. See, e.g., "Whole Genome Chromatin IP Sequencing," Illumina, Inc (2010), available at http://www.illumina.com/Documents/products/datasheets/datasheet_chip_sequence.pdf (Chromatin Immunoprecipitation with massively parallel sequencing).

For multiplex analysis of (limited) bulk samples, one may rely on chromatin indexing (MINT-ChIP; iChIP), where MNase-fragmented chromatin are indexed by ligation to a uniquely barcoded adaptor and then pooled and processed in multiplex through all subsequent phases, either with (MINT-ChIP) or without (iChIP: Lara-Astiaso, D., Weiner, A., Lorenzo-Vivas, E., Zaretsky, I., Jaitin, D. A., David, E., Keren-Shaul, H., Mildner, A., Winter, D., Jung, S., Friedman, N. & Amit, I. Immunogenetics. Chromatin state dynamics during blood formation. Science. 345, 943-949, doi:10.126/science.1256271 (2014). PMCID:4412442) carrier chromatin (without adaptors).

The method of the invention may include a step of determining proteins. Recently developed assays (e.g., CyTOF: Bendall, S. C., Simonds, E. F., Qiu, P., Amir el, A. D., Krutzik, P. O., Finck, R., Bruggner, R. V., Melamed, R., Trejo, A., Ornatsky, O. I., Balderas, R. S., Plevritis, S. K., Sachs, K., Pe'er, D., Tanner, S. D. & Nolan, G. P. Single-cell mass cytometry of differential immune and drug responses across a human hematopoietic continuum. Science. 332, 687-696, doi:10.1126/science.1198704 (2011). PMCID: 3273988), allow multiplexed, single cell detection of dozens of proteins in millions of cells, but rely on antibodies and cannot yet be combined with DNA readout. Darmanis et al. Simultaneous Multiplexed Measurement of RNA and Proteins in Single Cells, Cell 14, (2016)—uses PEA and RT-qPCR to detect proteins and mRNA species from the same single cell using split lysates (76 proteins, 96 mRNA) (see also Genshaft et al. Multiplexed Targeted Profiling of Single-Cell Proteomes and Transcriptomes in a Single Reaction, submitted to *Genome Biology*. Frei et al. Highly multiplexed simultaneous detection of RNAs and proteins in single cells, *Nature Methods* (2016)—uses cytof to measure approximately 40 combined targets between mRNA and protein. Conversely, mass spectrometry (LC-MS/MS) allows quantitative analysis of entire proteomes, but deep analysis requires large amounts of protein/cells. To measure single cell protein levels and post-translational modifications (PTMs), one may use one of three complementary antibody-based assays: (1) standard flow cytometry with a few proteins/PTMs, >$10^6$ single cells); (2) CyTOF (Bendall, S. C., Simonds, E. F., Qiu, P., Amir el, A. D., Krutzik, P. O., Finck, R., Bruggner, R. V., Melamed, R., Trejo, A., Ornatsky, O. I., Balderas, R. S., Plevritis, S. K., Sachs, K., Pe'er, D., Tanner, S. D. & Nolan, G. P. Single-cell mass cytometry of differential immune and drug responses across a human hematopoietic continuum. Science. 332, 687-696, doi:10.1126/science.1198704 (2011). PMCID:3273988) (heavy metal labeling with multiplex barcoding; ~30-50 proteins/PTMs, $10^5$-$10^6$ single cells); and (3) novel, highly multiplexed, DNA sequencing-based readouts of protein levels (100s proteins/PTMs; $10^6$ cells). For sequencing based readouts, one may use one of two approaches, geared at detecting hundreds of proteins in single cells: Immuno-Seq (when antibodies can be washed out: Niemeyer, C. M., Adler, M. & Wacker, R. Detecting antigens by quantitative immuno-PCR. Nat Protoc. 2, 1918-1930, doi:10.1038/nprot.2007.267 (2007)) and proximity extension assays (PEA, when antibodies cannot be washed away: Hammond, M., Nong, R. Y., Ericsson, O., Pardali, K. & Landegren, U. Profiling cellular protein complexes by proximity ligation with dual tag microarray readout. PLoS One. 7, e40405, doi:10.1371/journal.pone.0040405 (2012). PMCID: 3393744; Nong, R. Y., Wu, D., Yan, J., Hammond, M., Gu, G. J., Kamali-Moghaddam, M., Landegren, U. & Darmanis, S. Solid-phase proximity ligation assays for individual or parallel protein analyses with readout via real-time PCR or sequencing. Nat Protoc. 8, 1234-1248, doi:10.1038/nprot.2013.070 (2013); Stahlberg, A., Thomsen, C., Ruff, D. & Aman, P. Quantitative PCR analysis of DNA, RNAs, and proteins in the same single cell. Clin Chem. 58, 1682-1691, doi:10.1373/clinchem.2012.191445 (2012).) These use DNA-sequence based encoding, and are compatible with other genomic readouts (e.g., sgRNA barcodes). DNA-sequence tags can be conjugated to antibodies (Janssen, K. P., Knez, K., Spasic, D. & Lammertyn, J. Nucleic acids for ultra-sensitive protein detection. Sensors (Basel). 13, 1353-1384, doi:10.3390/s130101353 (2013). PMCID:3574740), nanobodies (Pardon, E., Laeremans, T., Triest, S., Rasmussen, S. G., Wohlkonig, A., Ruf, A., Muyldermans, S., Hol, W. G., Kobilka, B. K. & Steyaert, J. A general protocol for the generation of Nanobodies for structural biology. Nat Protoc. 9, 674-693, doi:10.1038/nprot.2014.039 (2014). PMCID:4297639; Theile, C. S., Witte, M. D., Blom, A. E., Kundrat, L., Ploegh, H. L. & Guimaraes, C. P. Site-specific N-terminal labeling of proteins using sortase-mediated reactions. Nat Protoc. 8, 1800-1807, doi:10.1038/nprot.2013.102 (2013). PMCID:3941705) or aptamers (Janssen, K. P., Knez, K., Spasic, D. & Lammertyn, J. Nucleic acids for ultra-sensitive protein detection. Sensors (Basel). 13, 1353-1384, doi:10.3390/s130101353 (2013). PMCID:3574740.).

Spatially Patterning Cells on Surfaces

In one embodiment, a biocompatible surface for patterning cells is prepared. This surface can be inert (e.g., a functionalized glass slide) or biological (e.g. cells). The cell functionalizing probe is then flowed over the surface and the region where cell type 1 is to be placed is photoactivated. Excess cell functionalizing probe is then washed away, and cell functionalizing barcoded tag (e.g., an oligo) is be flowed over the surface, selectively attaching as outlined below in the region that was photoactivated.

In one embodiment, the cell functionalizing tag (e.g., oligo tag) is click enabled (e.g., azide modified) and will react with the click moiety on the probe (e.g., a strained alkene or strained alkyne).

In another embodiment, streptavidin is flowed over the surface, which can bind the biotin on the cell functionalizing probe covalently attached to the surface. Biotin functionalized cell functionalizing barcoded tag (e.g., biotin functionalized oligos) are then flowed over the surface and bind to the streptavidin which is attached to the cell functionalizing probe that is, in turn, covalently attached to the surface.

After the cell functionalizing barcoded tag (e.g., oligos) have been added for cell type 1, this process will be repeated from the beginning to add another cell functionalizing probe and tag (e.g., oligo) specific for cell type 2, and so on until n cell type specific cell functionalizing barcoded tag (e.g., oligo) have been conjugated to the surface.

In parallel, different cell functionalizing barcoded tags (e.g., oligos) can conjugated to cell types 1 through n. In one embodiment, the cell functionalizing barcoded tag (e.g., oligos) are the reverse complement of the cell functionalizing barcoded tag (oligos) conjugated to the surface, specific for cell types 1 through n. In this way, cell types 1-n are placed in the locations specified by oligos 1-n.

In one embodiment, the cell functionalizing barcoded tag (e.g., oligos) are covalently attached to the cells via a click reaction. More specifically, an NHS-click reagent (DBCO, OND, etc.) is covalently attached to cells (NHS reacts with primary amines on cell surface proteins). Afterwards, each cell type is incubated with a cell functionalizing barcoded tag (e.g., an azide oligo) unique to that cell type (which is the reverse complement of the oligo tag patterned on the surface for the placement of that cell type).

In another embodiment, the cell functionalizing barcoded tag (e.g., oligos) are bound to the cell via a biotin-streptavidin-biotin linkage. More specifically, an NHS-biotin reagent is covalently attached to cells. After excess NHS-biotin has been washed away, cells are incubated with streptavidin. Afterwards each cell type is incubated with its cell type specific oligonucleotide (which is the reverse complement of the oligonucleotide that was patterned onto the surface for each cell type's placement).

DNA conjugation to cells has also been accomplished by Staudinger ligation (Gartner and Bertozzi, Programmed assembly of 3-dimensional microtissues with defined cellular connectivity, 2009), hydrazone conjugation (Twite et al., Direct attachment of microbial organisms to material surfaces through sequence-specific DNA hybridization, 2012), incorporation of dialkyl-DNA into the cell membrane (Selden et al., Chemically Programmed Cell Adhesion with Membrane-Anchored Oligonucleotide, 2012), and fatty-acid-conjugated duplex DNA (Weber et al., Efficient Targeting of Fatty-Acid Modified Oligonucleotides to Live Cell Membranes through Stepwise Assembly, 2014). In an embodiment (seems preferred in the field; fatty-acid conjugated duplex of DNA), two single stranded DNAs conjugated to lipids are added to the cells sequentially. The first oligonucleotide added is long and contains a region that is the reverse complement of the DNA patterned on the surface. It is mixed with the cells and inserted into their plasma membrane. The second, shorter oligonucleotide is then added, and it is complementary to the DNA proximal to the lipid of the first oligonucleotide.

After cells have been conjugated to oligonucleotidess, the cells are added to the surface and are spatially patterned according to their cell surface oligonucleotide and its hybridization to the oligonucleotides on the surface.

Subsequent rounds of addition can be used to build complex 3-dimensional architectures as well as 2-dimensional ones.

EXAMPLES

Figure 13A:
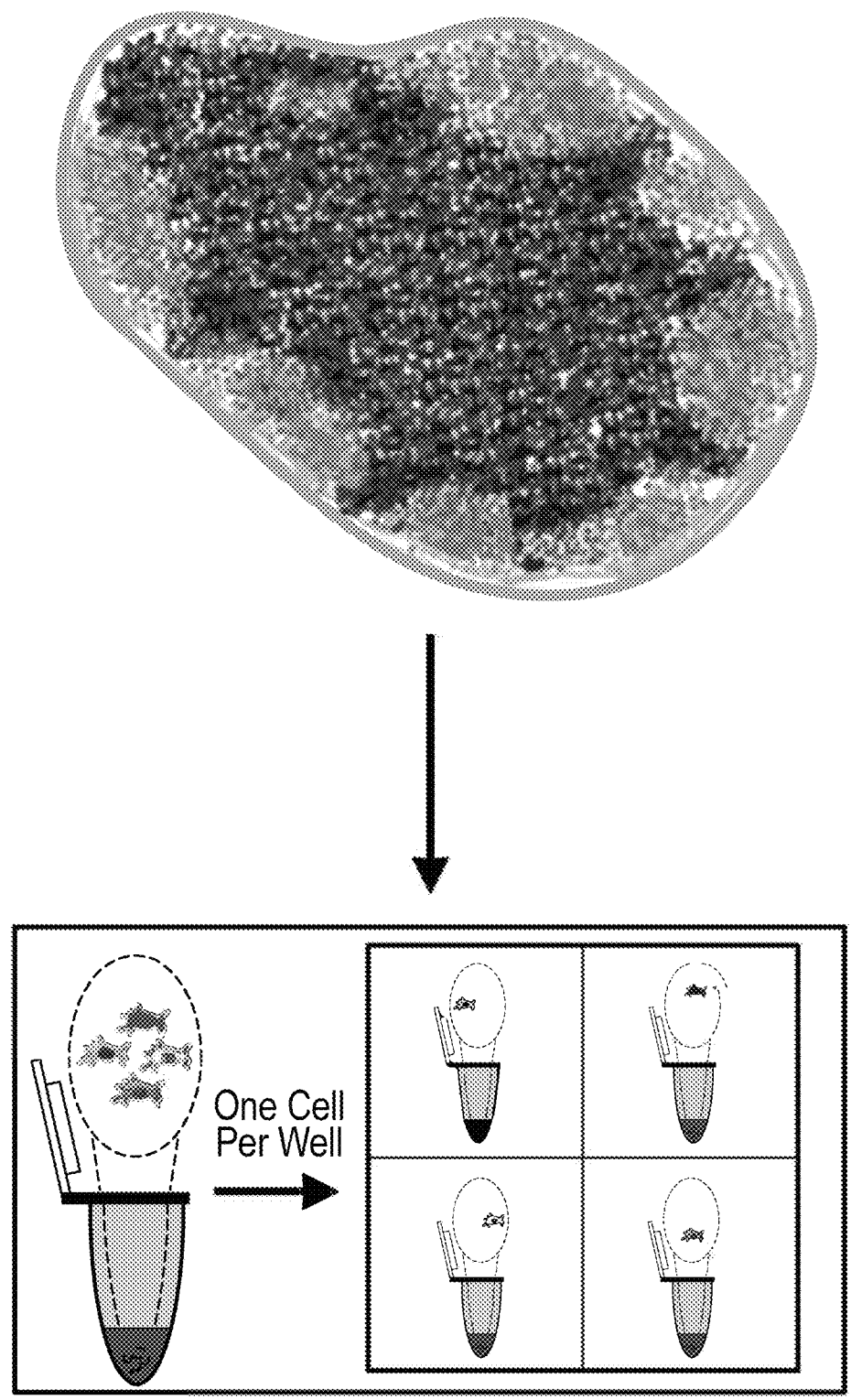
FIG. 13A is a schematic detailing the motivations behind designing "SpaceCat". Left: illustration of classic single cell RNA-Sequencing, with large tissue structures combined during tissue dissociation, with loss of locational information. Center: Illustration of pilot examples, with fine dissection tools to study regionality within the "macro-environment". Right: Illustration of ideal data structure with our protocol, enabling high resolution structural information retained through tissue dissociation, and subsequent single-cell RNA-Sequencing.
Figure 13A:
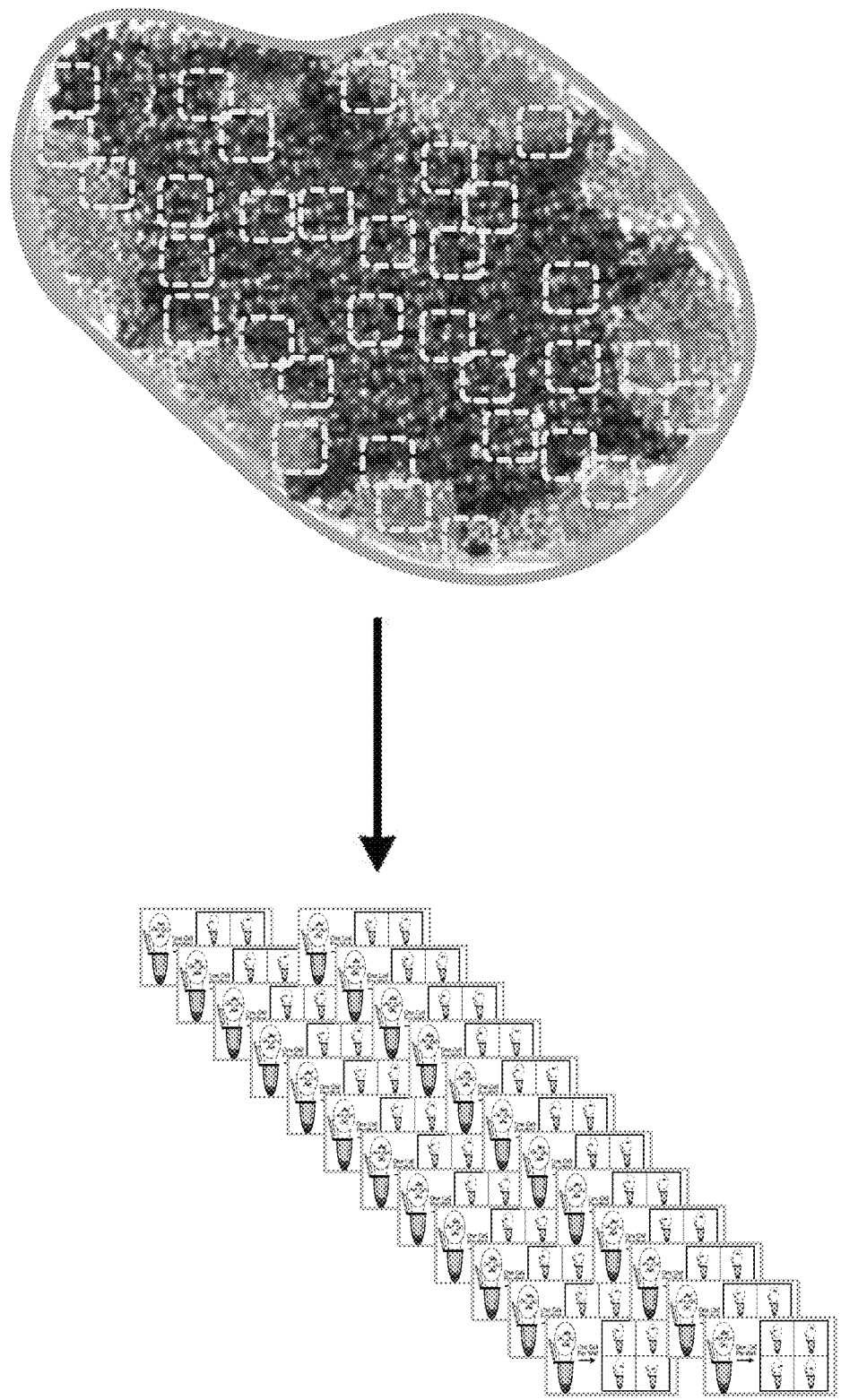
Figure 13B:
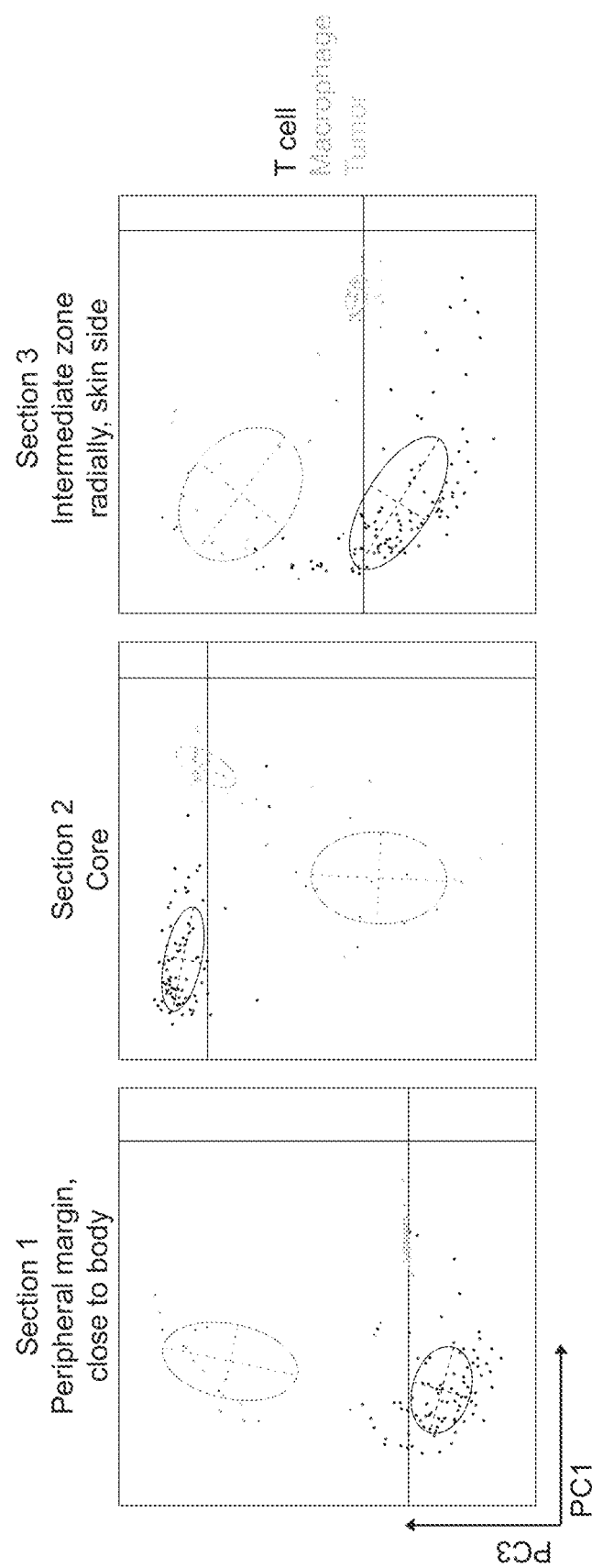
FIG. 13B shows pilot data on the "macro-environment (~10^4)". As a proof of concept, a large (~2.5 mm^3) MC38 tumor from a mouse model was dissected into 3 isolates based on location (annotated in each plot). T cells, macrophages, and tumor cells we FACS sorted and single-cell RNA-Sequencing was performed. The data were illustrated using a projection of the top principal components regional differences between each section.
Figure 14:
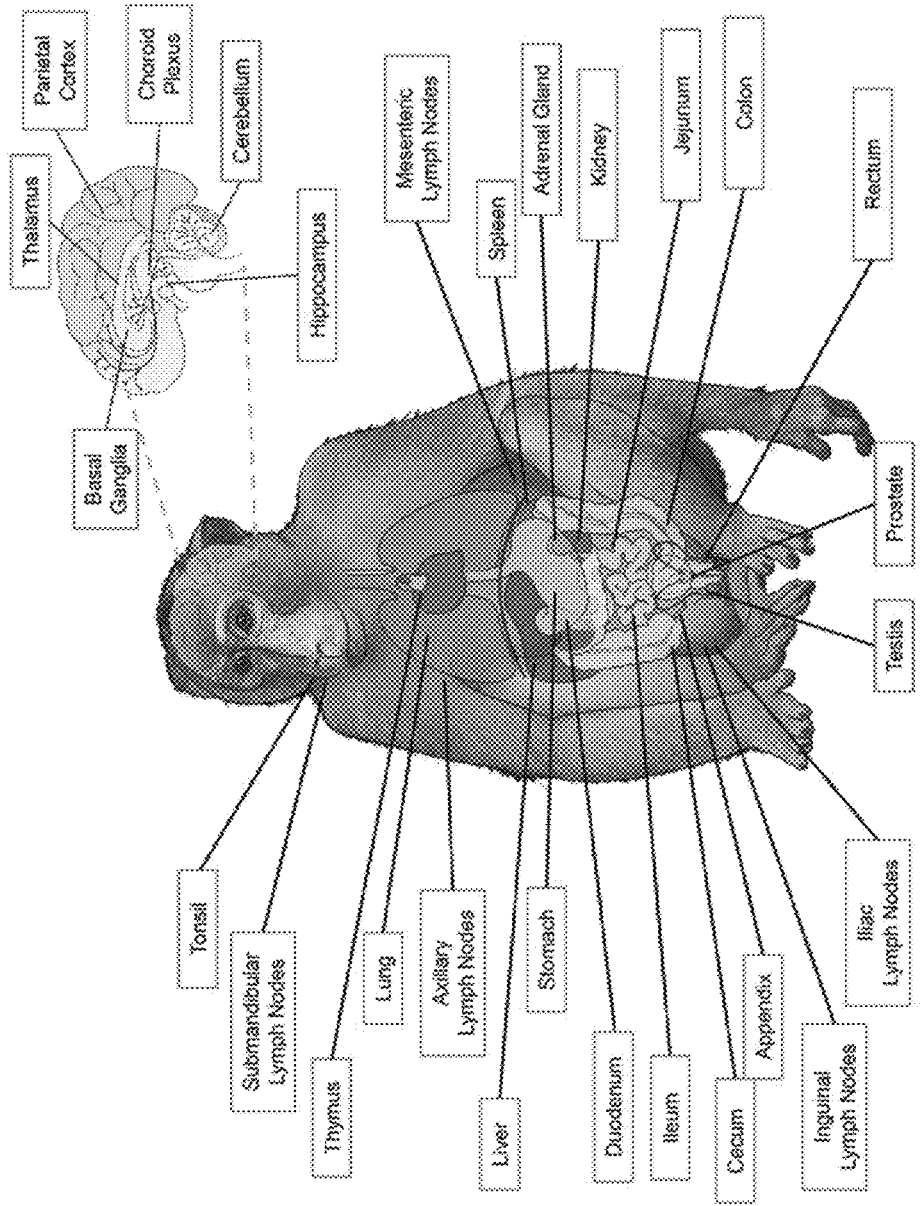
FIG. 14 illustrates an atlas of cellular phenotypes in SHIV from a non-human primate across a subset of different tissue types.

Using the cell functionaling probe and cell functionalizing barcoded tag described herein with fine dissection tools, Applicants studied the regionality within the "macro-environment," i.e., $\sim 10^4$ cells. Applicants dissected a large ($\sim 2.5$ mm^3) MC38 tumor from a mouse model into 3 isolates based on location: section 1 (peripheral margin, close to body), section 2 (core), and section 3 (intermediate zone radially, skin side). Applicants FACS sorted T cells, macrophages, and tumor cells and completed single-cell RNA-Sequencing. High resolution structural information was retained through tissue dissociation and subsequent single-cell RNA-Sequencing, as illustrated in FIG. 13B using a projection of the top principal components regional differences between each section.

Figure 15:
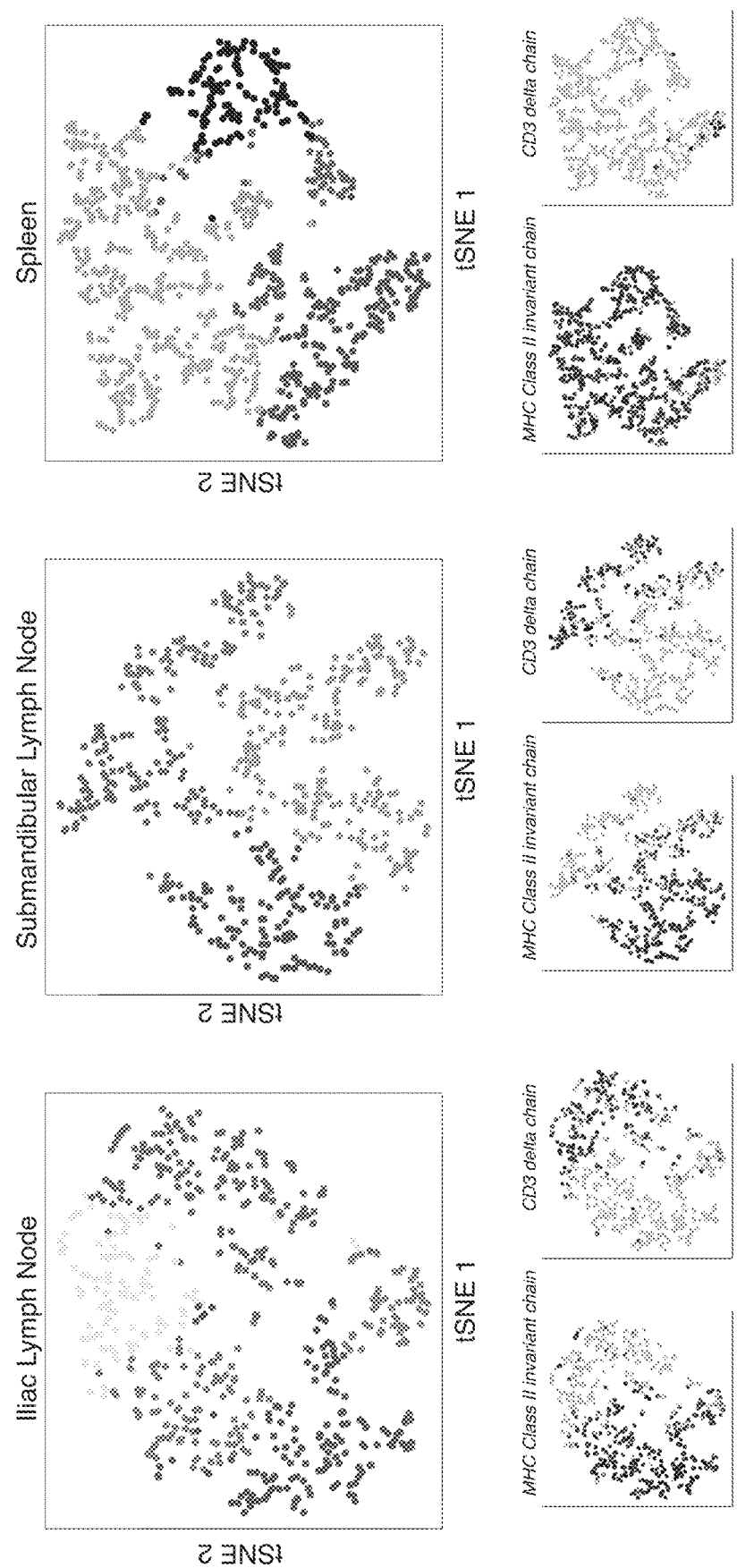
FIG. 15 illustrates representative data from a non-human primate necropsy study. A t-stochastic neighbor embedded (t-SNE) plot of the highly variant genes is presented here, to illustrate non-equivalence of the distinct tissues. Even functionally and anatomically similar tissues, such as the Iliac lymph node and the Submandibular lymph node, are composed of differing frequencies of cell types and thus show differing projections into tSNE space. As illustrated in the lower panels, three secondary lymphoid tissues exhibit large variation in the frequency of T cells (as determined by CD3 delta chain), where darker shades indicate greater levels of expression.

Applicants further studied necropsy of non-human primate with single cell RNA-Sequencing of complete tissue composition across ~10 tissues. Applicants revealed that tissues with similar functionalities and anatomic designations (e.g. lymph node, e.g. different regions along the small intestine) have distinct cellular composition; presumably relevant for local biology and specialized function. Distinct tissues were dissociated from necropsy and single-cell RNA-Sequencing was completed on all viable cells. As illustrated in FIG. 15, even functionally and anatomically similar tissues, such as the Iliac lymph node and the Submandibular lymph node, are composed of differing frequencies of cell types and thus show differing projections into tSNE space. Applicants also observed that 3 secondary lymphoid tissues exhibit large variation in the frequency of T cells (as determined by CD3 delta chain).

Figure 16:
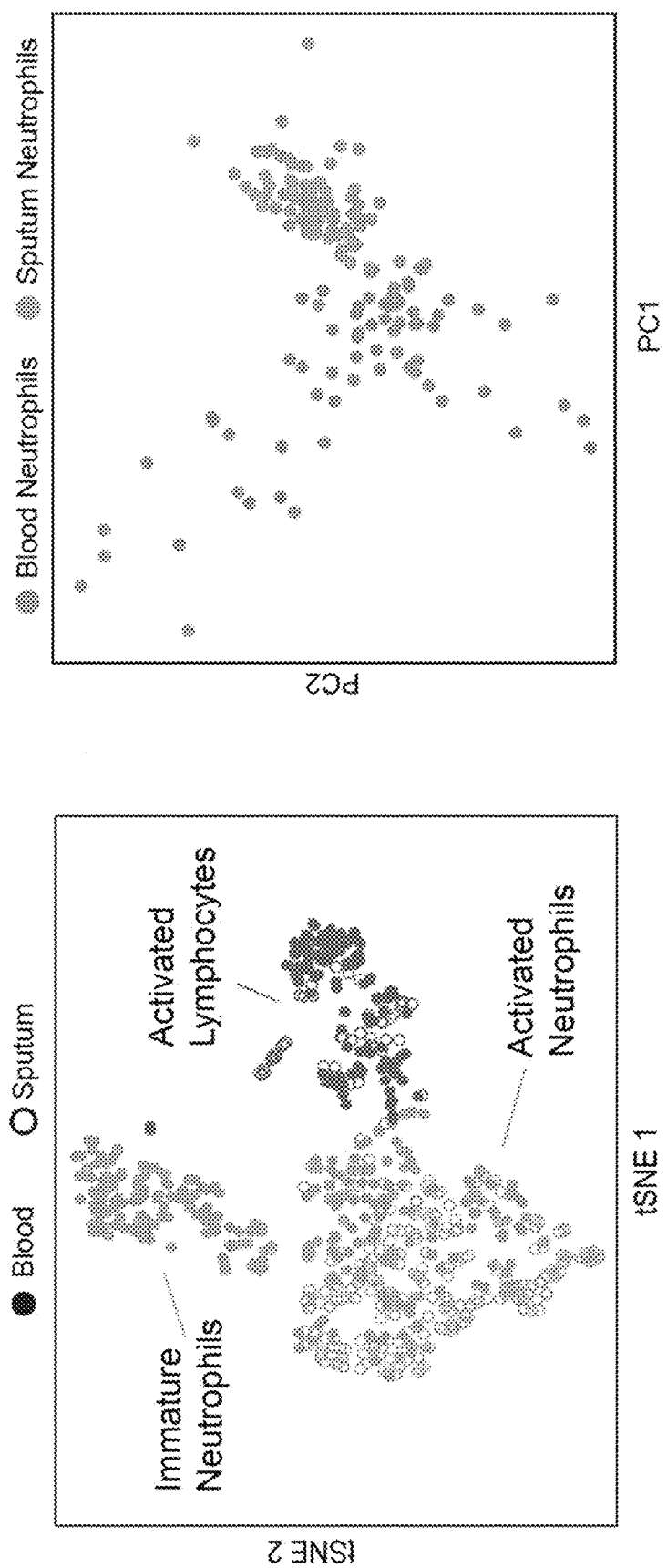
FIG. 16 demonstrates the principle that unique cellular phenotypes emerge based on tissue compartment (and therefore, local regional effects). On the left panel, a tSNE plot illustrates that the dominant factor in cell-cell variability is the cell type (e.g. neutrophils cluster with neutrophils, lymphocytes cluster separately. On the right panel, a principal components analysis plot shows that indeed the tissue compartments are a major source of variability between cells of the "same type" (here: activated neutrophils).
Figure 17:
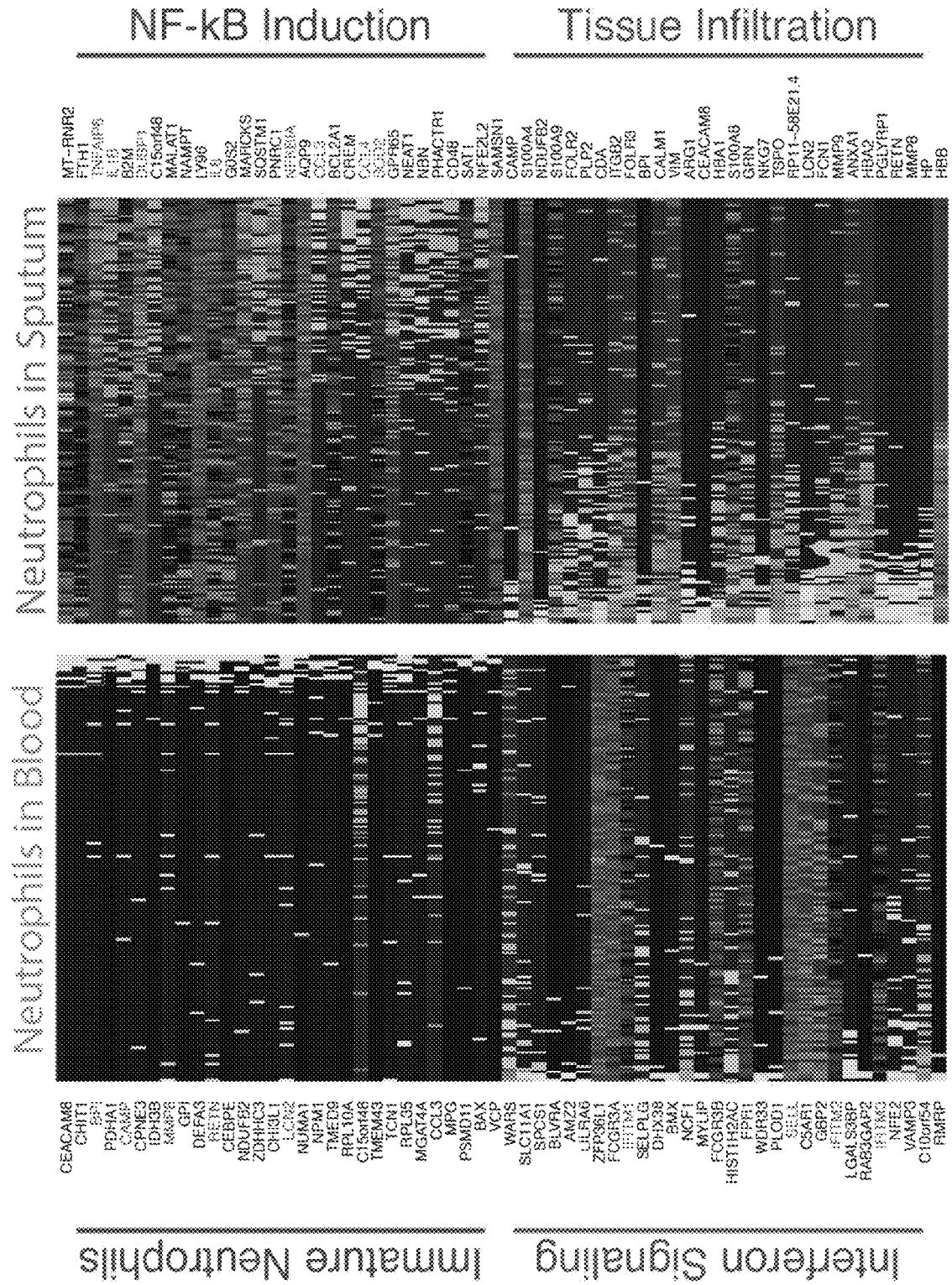
FIG. 17 shows two heatmaps detailing the origin of the variability between blood-derived neutrophils and sputum-derived neutrophils.
Figures 18A, 18B, 18C:
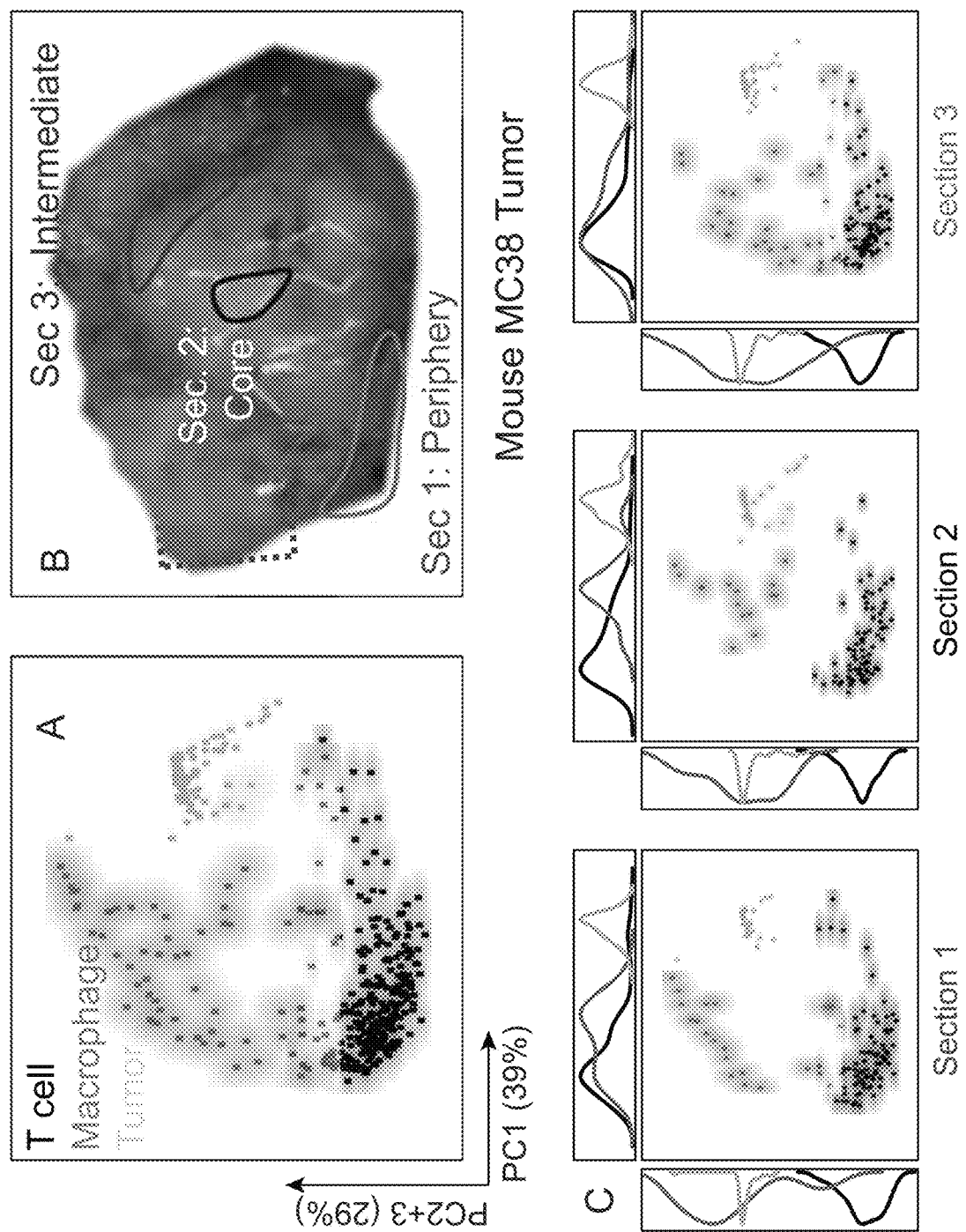
FIG. 18A illustrates the different cell types present in the MC38 tumor. T cells, Macrophages, and Tumor cells were FACS sorted.
FIG. 18B is a photograph of the dissected tumor, with masks to define regions.
FIG. 18C are PCA plots as in FIG. 18A, divided by the region of origin.
Figure 19:
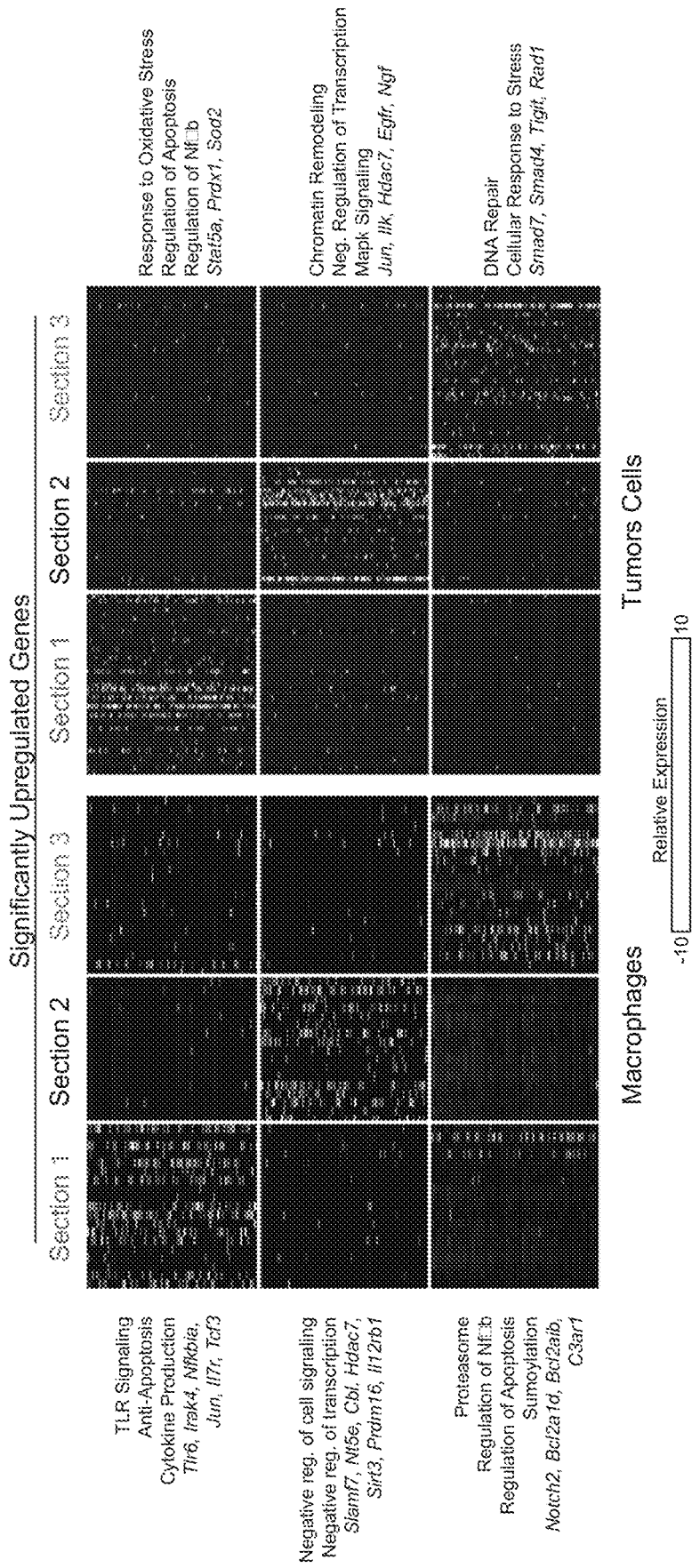
FIG. 19 shows heatmaps describing the regional differences identified in like cell types (between macrophages, between tumor cells) based on location in the original solid structure. On the left, genes that are significantly differentially expressed in the macrophages for each section are plotted (e.g. high in Section 1, high in Section 2, high in Section 3), and the common pathways that those genes represent are detailed in the margins. The same analysis is completed for the tumor cells on the right.

Applicants demonstrated the principle that unique cellular phenotypes emerge based on tissue compartment (and therefore, local regional effects). From the same donor, Applicants collected the blood and sputum and completed single cell RNA-Sequencing on the isolated cells. FIG. 16 illustrates that the dominant factor in cell-cell variability is the cell type (e.g. neutrophils cluster with neutrophils, lymphocytes cluster separately. In addition, the principal components analysis plot shows that indeed the tissue compartments are a major source of variability between cells of the "same type" (here: activated neutrophils). Applicants observed that the phenotype between cell types that are canonically considered "equivalent" are actually majorly defined by the microenvironment of origin. Moreover, Applicants observed that an entire subset of cell phenotype (immature neutrophils) exists in the blood of human donors, but not present in the sputum.

Figure 20:
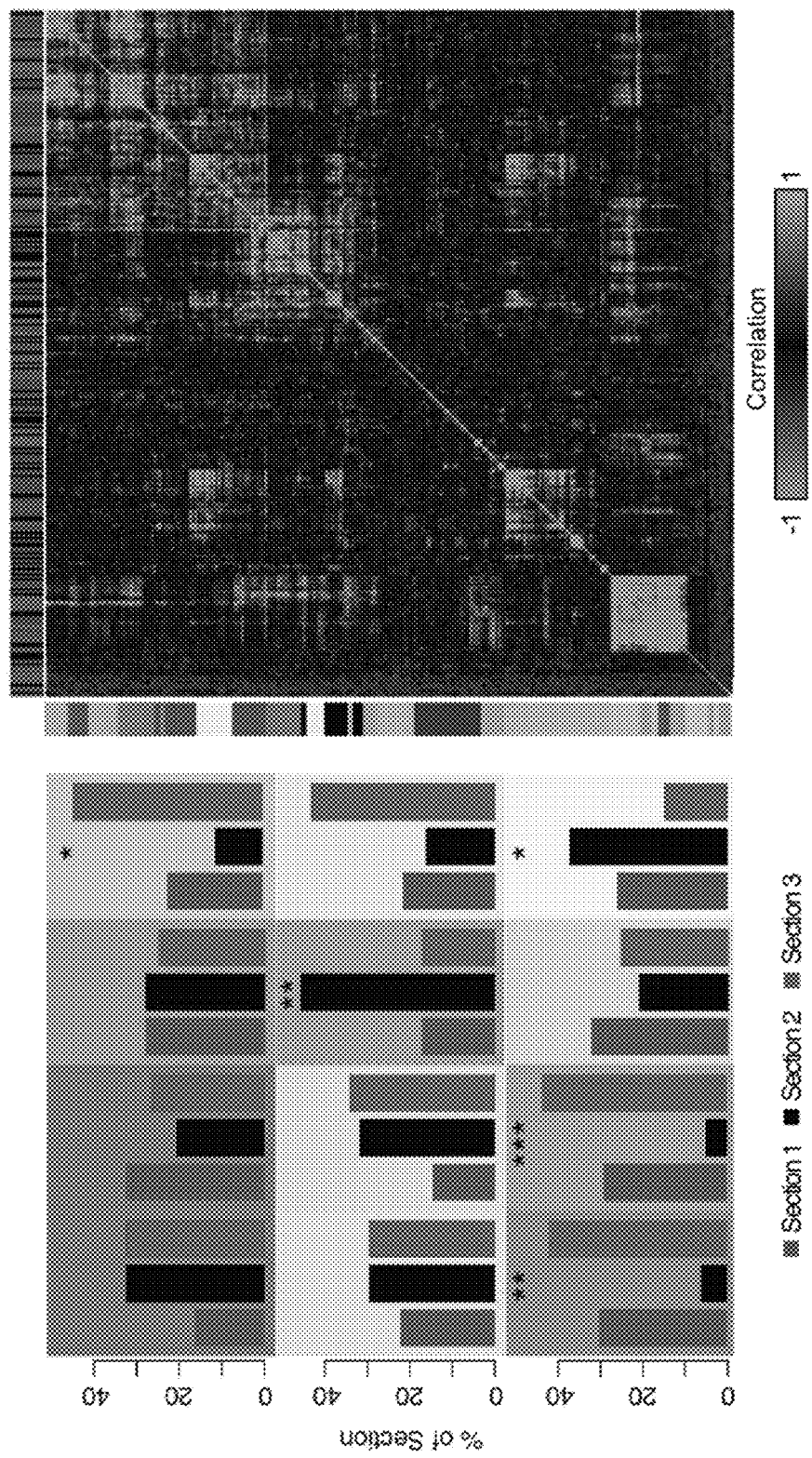
FIG. 20 T cells cluster over exhaustion markers. Single cells are scored by their expression of canonical markers of exhaustion, and subsequently clustered by similarity. As illustrated, certain regions of the tumor contain cells with exhaustion phenotypes that are similar to each other (within a microenvironment) yet are distinct from other cells in distant regions.

A mouse tumor model (MC38, colon carcinoma) was used as an archetypal tissue where intratumoral regionality could be observed and leveraged to better understand modes of cell-cell interaction (microenvironment effects). Applicants observed that cell behaviors are altered by their local neighborhood. Different cell types in the tumor tissue, T cells, Macrophages, and Tumor cells, were FACS sorted. T cells, sorted as previously described, from multiple regions in a single tumor were analyzed for regionally-distinct phenotypes. This analysis is motivated by the assumption that regionally distinct phenotypes may represent regional alterations in the interacting cells. Applicants looked at exhaustion, a T cell phenotype largely defined by the interaction with exhaustion-inducing tumor cells and potentially other cell mediators and secreted molecules. Applicants observed that certain regions of the tumor contain cells with exhaustion phenotypes that are similar to each other (within a microenvironment), yet are distinct from other cells in distant regions (FIG. 20). Moreover, the addition of additional metadata of space into traditional single-cell RNA-Sequencing datasets necessitates new formalisms to analyze cell-cell interaction and rationality.

Figure 21A:
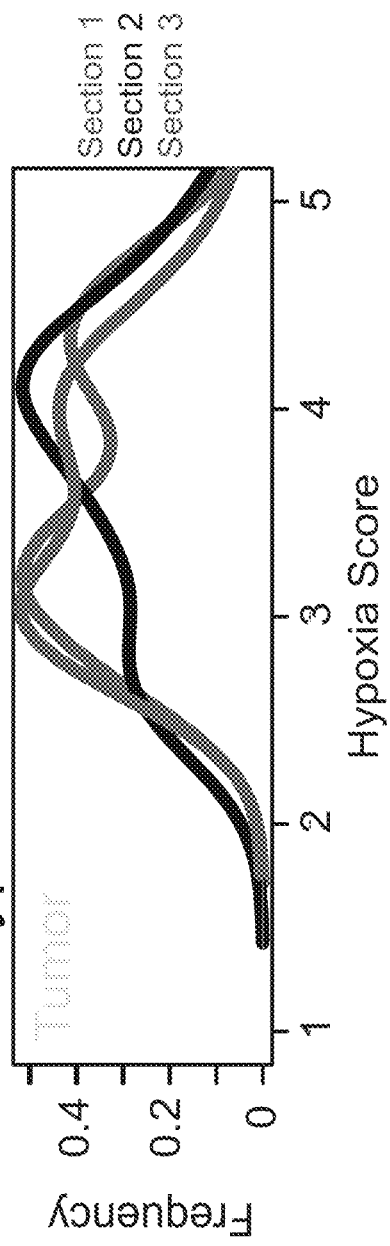
FIG. 21A illustrates that cells in the center of a tumor structure exhibit a strong signature for hypoxia.
Figure 21B:
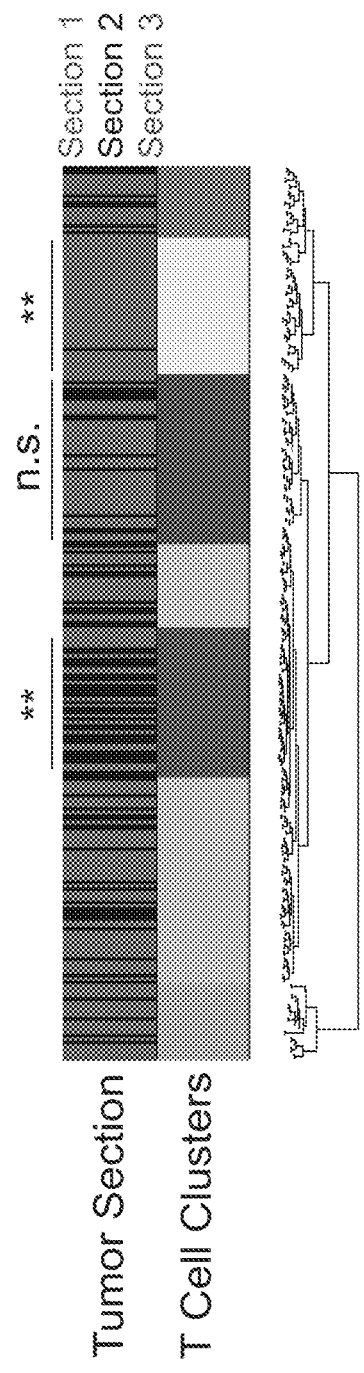
FIG. 21B shows that the T cells that segregate between different tumor regions express different interferon signaling pathway components, and at different magnitudes. This indicates immunity is regionally confined and reacts differently depending on the local influences.
Figure 22:
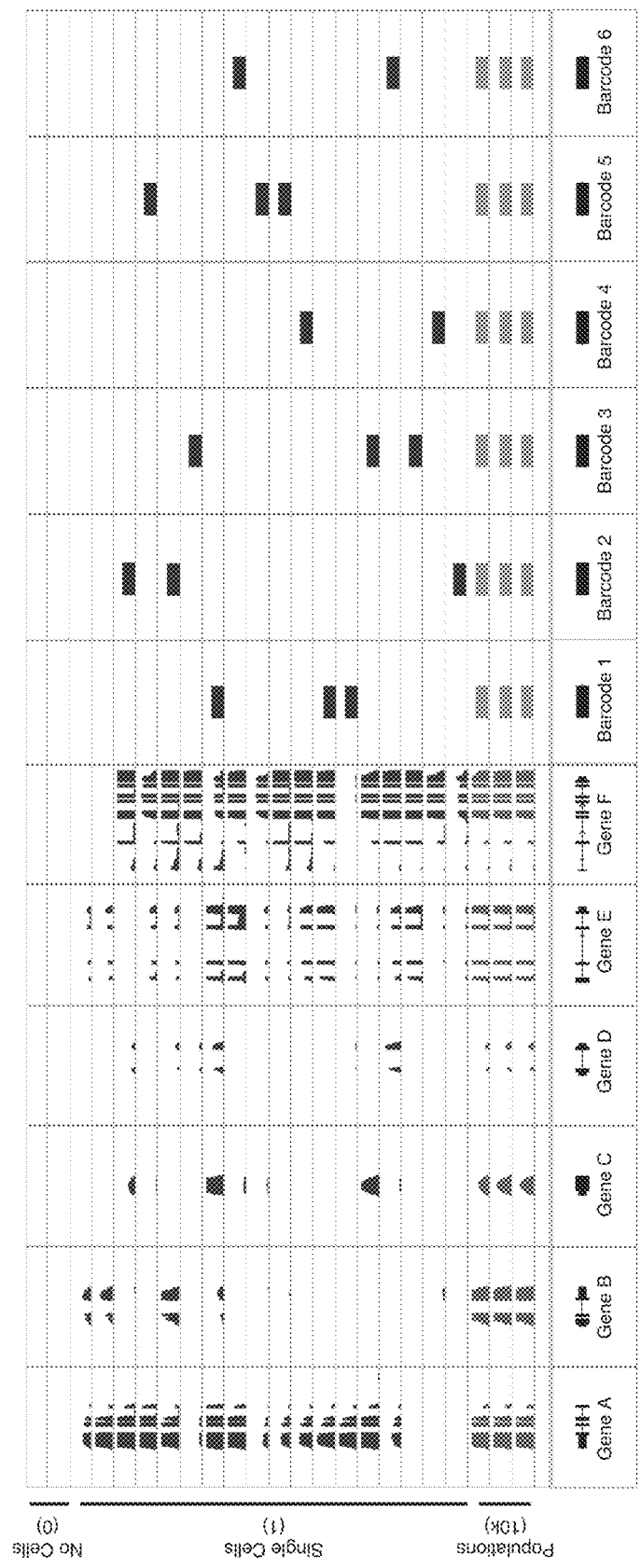
FIG. 22 is a schematic of the computational analysis required for spatial tags on single cells. Here, single cells are represented in each row of the graph, and height (blue) of each peak represents the sum of reads that align to certain locations on the gene (such that a highly expressed gene will have many genes that "pile-up" over their exons, outlined along the bottom row, e.g. "Gene A"). On the right, Applicants illustrate how DNA barcodes will accompany single cells based on their location in space. This will individually assign single cells to common location in the native tissue, as read out from sequencing data.
Figure 22:
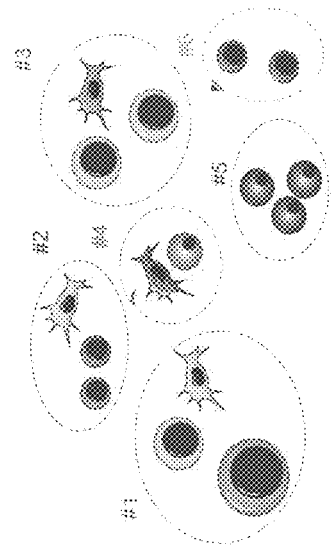
Figure 22:
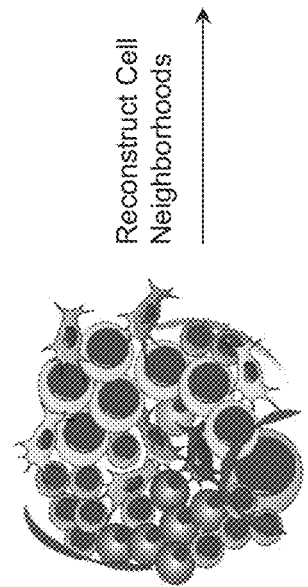
Figure 23:
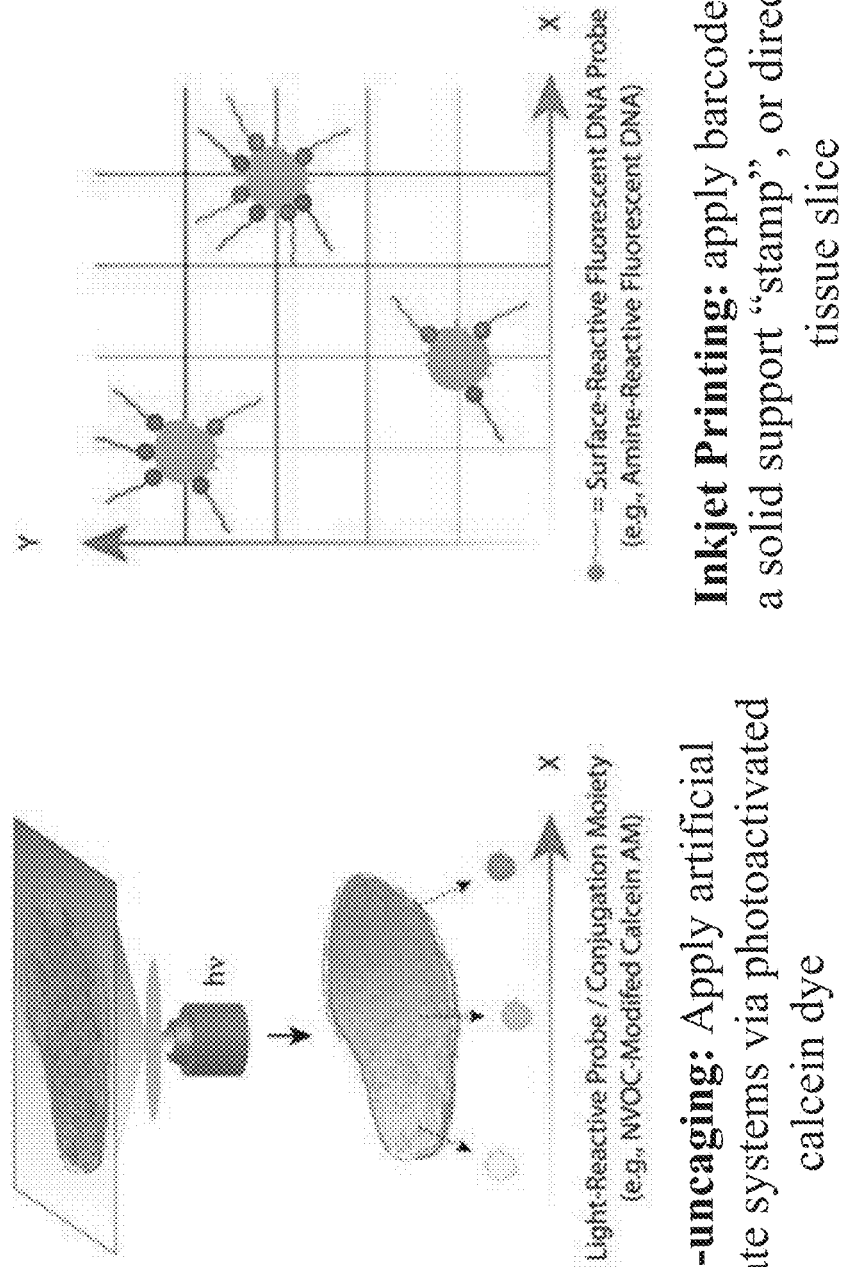
FIG. 23 presents alternative, parallel and supplementary schemes for identify single cells by their spatial configuration in a native tissue. On the left, Applicants illustrate the mechanism of photo-uncaging, wherein a certain wavelength of light mediates uncaging, and therefore fluorescence of a molecule that can be identified and cells can be sorted based on this tag. On the right, Applicants illustrate a method wherein specific DNA barcodes are printed onto a surface, such that they can react with moieties on the surface of functionalized single cells, tagging the single cell location in space.
Figure 24:
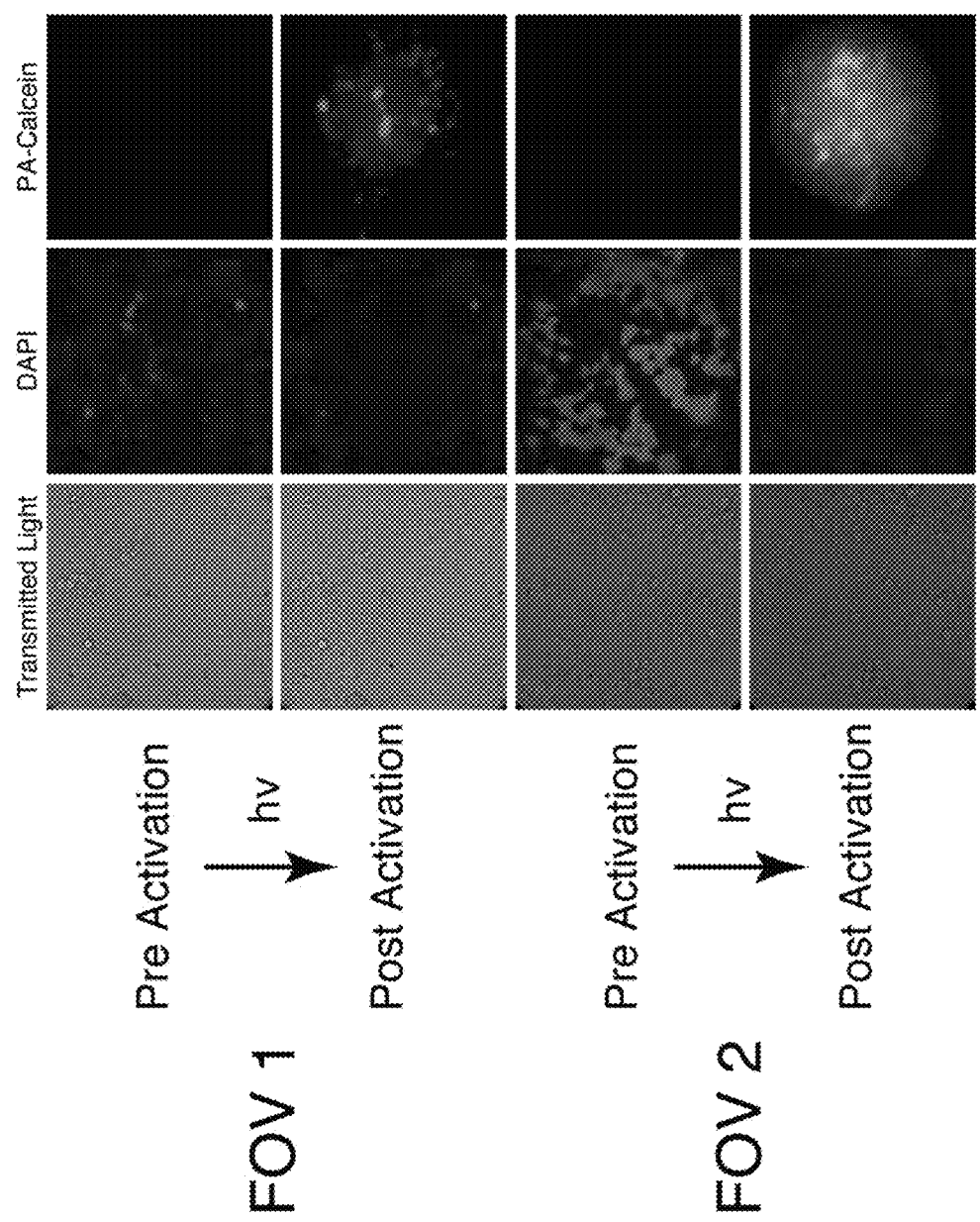
FIG. 24 illustrates the use of NVOC-caged calcein dye as a light-dependent uncaging system to identify cells based on their location. Two fields of view (FOV) are shown, in which a set of cells is identified as viable by DAPI staining in the "pre-activation" image, and then are subsequently exposed to light that enables calcein to be un-caged and fluoresce inside of viable cells. The "post activation" images are taken shortly thereafter, illustrating that the center of the FOV where uncaging wavelengths have been directed show new fluorescence in the calcein channel. Bleaching in the DAPI channel in the post-activation images is also observed.
Figure 25:
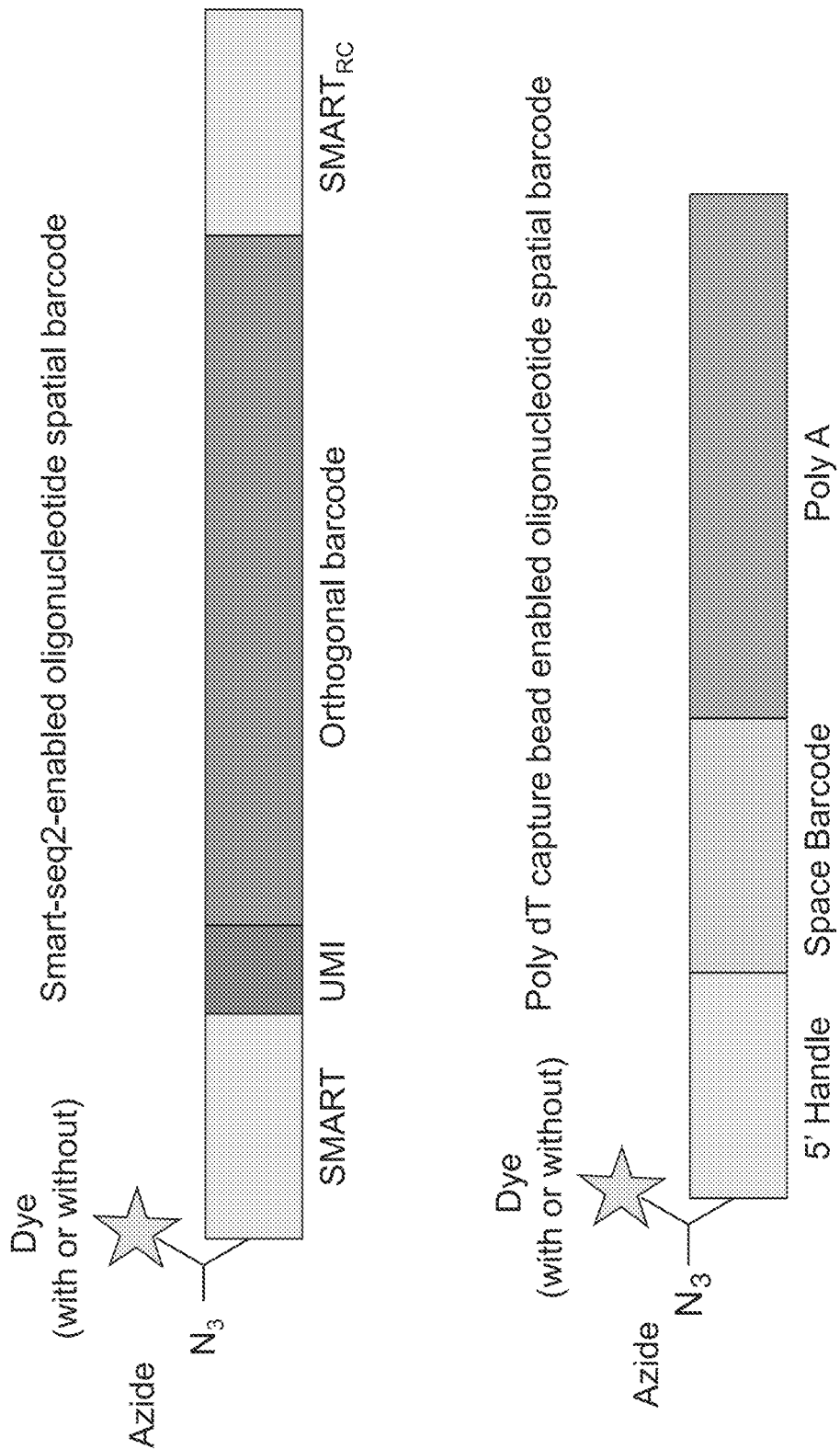
FIG. 25 illustrates different examples of a cell functionalizing barcoded tag ("oligo" or oligonucleotide tag).
Figure 26:
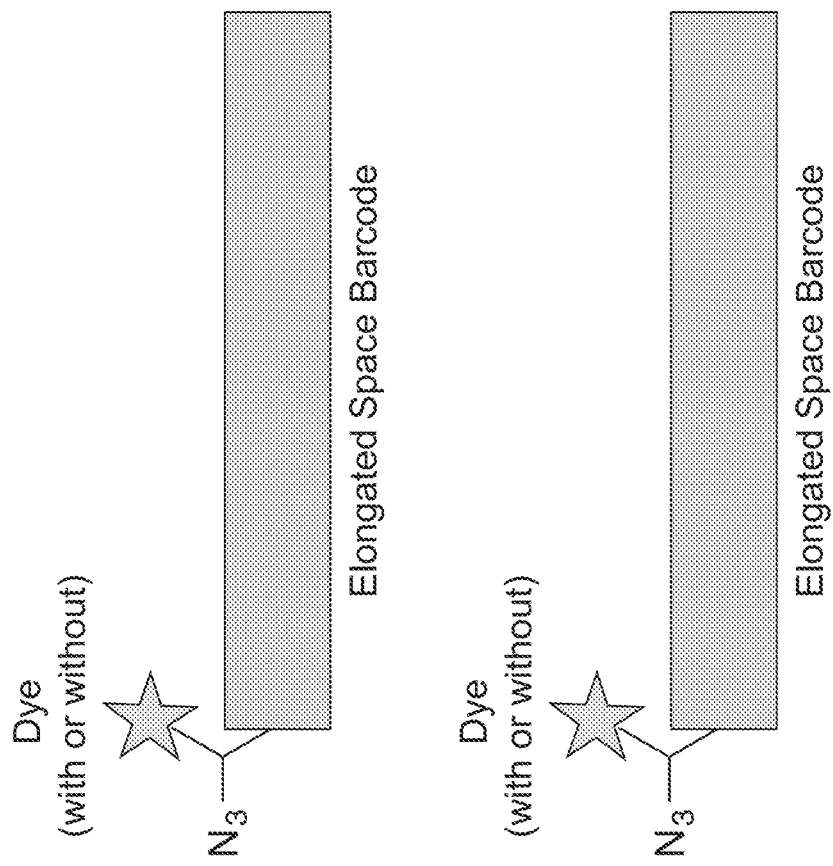
FIG. 26 illustrates examples of oligo constructs for patterning surfaces.

Further, Applicants observed that specific cellular phenotypes are altered between different sections in a tumor structure, indicating that the microenvironment, interacting cell types, and the spatial relationships between each of these units plays a critical role in emergent tissue behavior and phenotype. As illustrated in FIG. 21A, cells in the center of a tumor structure exhibit a strong signature for hypoxia. FIG. 21B demonstrates the T cells that segregate between different tumor regions express different interferon signaling pathway components, and at different magnitudes. This indicates immunity is regionally confined and reacts differently depending on the local influences.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A cell functionalizing probe comprising:
   (a) a polyadorned molecule comprising 3 to 5 substituents, comprising;
      (i) a first photoactivated cell-surface reactive group comprising a diazirine or a benzophenone;
      (ii) a first bio-orthogonal reactive group comprising a compound of Formula (I):

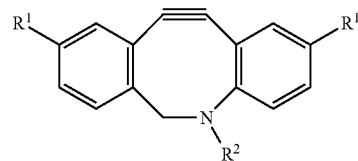

wherein $R^1$ is selected from the group consisting of —H, —X, —(CH$_2$)$_a$—NH-PG$^1$, O—(CH$_2$CH$_2$O)$_a$(CH$_2$)$_c$NH$_2$—PG$^1$, O—(CH$_2$CH$_2$O)$_a$—PG$^2$, —(CH$_2$)$_a$-O-PG$^2$;

$R^2$ is selected from the group consisting of —C(O)(CH$_2$)$_a$CO$_2$R$^{21}$, —CO$_2$(CH$_2$CH$_2$O)$_a$CO$_2$R$^{21}$, —C(O)(CH$_2$)$_a$CONR$^{21}$, —CO$_2$(CH$_2$CH$_2$O)$_a$CONR$^{21}$, and —CO(CH$_2$)$_a$NHCO(CH$_2$)$_a$O(CH$_2$CH$_2$O)$_c$(CH$_2$)$_a$NHR$^{21}$;

$R^{21}$ is selected from the group consisting of —H, —O(C$_1$-C$_6$ alkyl), —C$_1$-C$_8$ straight chain alkyl, —C$_1$-C$_8$ branched alkyl, —C$_2$-C$_8$ alkenyl, —C$_2$-C$_8$ alkynyl and —(C$_1$-C$_6$ alkyl)-O—(C$_1$-C$_6$ alkyl);

PG$^1$ is an amine protecting group or —H;

PG$^2$ is an alcohol protecting group or —H; and

X is selected from the group consisting of Cl, Br, I, and F;

a is independently any integer between 0 and 6;

c is independently any integer between 1 and 6; and the additional substituents are individually selected from a label, a cell-surface reactive group, or a bio-orthogonal reactive group, and wherein when the photoactivated cell-surface reactive group comprises benzophenone, the polyadorned molecule comprises phenyl, naphthyl, anthracenyl, phenanthrenyl, indanyl, indenyl, dihydroxyaryl or triazine.

2. The cell functionalizing probe of claim 1, wherein, in addition to the first bio-orthogonal reactive group, only one more of the 3 to 5 substituents of the polyadorned molecule contains an aromatic group.

3. The cell functionalizing probe of claim 2, wherein the single additional aromatic group is is dihydroxyaryl or triazine.

4. The cell functionalizing probe of claim 1, wherein the label comprises a fluorophore, a peptide-based tag, biotin, affinity reagent, hapten, lanthanide heavy metal(s) or combination thereof, or an oligonucleotide.

5. The cell functionalizing probe of claim 4, wherein the fluorophore comprises a compound of Formula (II):

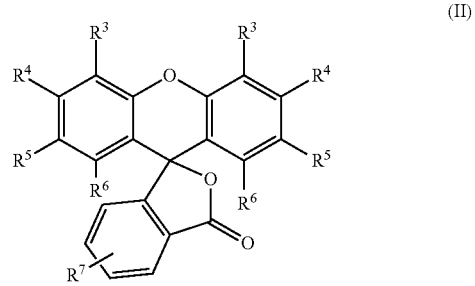

wherein $R^3$ is selected from the group consisting of —H, C$_1$-C$_6$ alkyl, —(CH$_2$)$_a$NR$^8$R$^9$, —NHC(O)—Y—R$^8$, —NHC(O)CHR$^8$R$^9$, —CHR$^8$R$^9$ and —(CH$_2$)$_a$—NR$^8$C(O)R$^9$;

$R^4$ is selected from the group consisting of —H, —OH, and —OR$^8$;

$R^5$ and $R^6$ are selected from the group consisting of —H, —OH, —X, —NO$_2$, —CN, —NH$_2$, —NHR$^8$, —C(O)R$^8$, and —C$_1$-C$_3$ perfluoro alkyl; $R^7$ is selected from the group consisting of —H, —OH, —X, —NO$_2$, —CN, —C(O)NH(CH$_2$)a —O(C$_1$-C$_6$ alkyl), —NH$_2$, —NHR$^8$, —NHC(O)—Y—R$^8$, —(CH$_2$)$_a$NR$^{68}$C(O)R$^9$, —NHC(O)CHR$^8$R$^9$, and —C$_1$-C$_3$ perfluoro alkyl;

$R^8$ and $R^9$ are independently selected from the group consisting of —H, NH$_2$, —(CH$_2$)$_a$—C(O)NH(CH$_2$)$_b$CH$_3$, —(CH$_2$)$_a$—C(O)NH(CH$_2$)$_b$C(O)NHPG$^3$, —(CH$_2$)$_a$—CO$_2$NHPG$^3$, —C$_1$-C$_8$ straight chain alkyl, —C$_1$-C$_8$ branched alkyl, —C$_2$-C$_8$ alkenyl, —C$_2$-C$_8$ alkynyl, and —(C$_1$-C$_6$ alkyl)-O—(C$_1$-C$_6$ alkyl); each of which is optionally substituted by a halogen, ether, vinyl group, allylic group, —NH$_2$, or —CN, —(CH$_2$)$_a$NR$^{88}$R$^{89}$, —(CH$_2$)$_a$C(O)NR$^{88}$R$^{89}$, an aromatic group, heteroaromatic group, C$_3$-C$_7$ cycloalkyl, a three to twelve membered heterocyclic group having up to 3 heteroatoms, and wherein each of which preceding cyclic group is optionally substituted from 1 to 3 substituents independently selected from a halogen, —C$_1$-C$_6$ alkyl, —C$_2$-C$_6$ alkenyl, —O(C$_1$-C$_6$ alkyl), —C(O)—, —OH, —NH$_2$, —CN, and —C$_1$-C$_3$ perfluoro alkyl;

$R^{88}$ and $R^{89}$ are independently selected from the group consisting of —H, —O(C$_1$-C$_6$ alkyl), —C$_1$-C$_8$ straight chain alkyl, —C$_1$-C$_8$ branched alkyl, —C$_2$-C$_8$ alkenyl, —C$_2$-C$_8$ alkynyl, and —(C$_1$-C$_6$ alkyl)-O—(C$_1$-C$_6$ alkyl);

Y is selected from a covalent bond, —O—, —NH—, and —C$_1$-C$_6$ alkyl;

X is selected from the group consisting of Cl, Br, I, and F;

PG$^3$ is any photolabile protecting group;

a is independently any integer between 0 and 6; and b is independently any integer between 0 and 6.

6. The cell functionalizing probe of claim 1, wherein the polyadorned molecule comprises phenyl, naphthyl, anthracenyl, phenanthrenyl, indanyl, indenyl, dihydroxyaryl or triazine.

7. The cell functionalizing probe of claim 1, wherein the additional substituent is a bio-orthogonal reactive group comprising an alkyne or strained alkyne.

8. The cell functionalizing probe of claim 1, wherein the photoactivated cell-surface reactive group comprises a diazirine.

9. The cell functionalizing probe of claim 1, wherein the photoactivated cell-surface reactive group is a benzophenone, and wherein the polyadorned molecule comprises phenyl, naphthyl, anthracenyl, phenanthrenyl, indanyl, indenyl, dihydroxyaryl or triazine.

10. A method of single-cell profiling in a subject in need thereof wherein the single cells are spatially resolved, the method comprising:
   (a) saturating tissue in the subject with a cell functionalizing probe according to claim 1;
   (b) activating the cell functionalizing probe;
   (c) labelling tissue with a cell functionalizing barcoded tag comprising a polyadorned molecule, wherein the molecule comprises 2 to 5 substituents comprising;
      (i) a click-enabled moiety, wherein the click-enabled moiety comprises an azide, tetrazine, tetrazole, or nitrone; and,
      (ii) an oligonucleotide barcode comprising a spatial barcode;
   (d) washing the tissue with an aqueous solution to remove unbound functionalizing probe;
   (e) repeating steps (a) through (d) from 1 to about 100 times;
   (f) separating labeled cells into a suspension of single cells or small cell aggregates;
   (g) optionally sorting and enriching cells comprising a cell functionalizing tag and a cell functionalizing probe via a cell separation method;
   (h) profiling single cell sequences, whole cell populations, or cell subpopulations; and,
   (i) optionally assembling the single cell sequences into a visual representation, wherein the relationship between amplified shared spatial barcodes of single cell sequences is obtained by a computational method; and,
   (j) analyzing cellular phenotypes using categorical spatial information.

11. A method of single-cell profiling in a subject in need thereof wherein the single cells are spatially resolved, the method comprising:
   (a) conjugating a cell functionalizing probe of claim 1 to a cell functionalizing barcoded tag comprising a polyadorned molecule, wherein the molecule comprises 2 to 5 substituents comprising;
      (i) a click-enabled moiety, wherein the click-enabled moiety comprises an azide, tetrazine, tetrazole, or nitrone; and,
      (ii) an oligonucleotide barcode comprising a spatial barcode whereby an active complex is formed;
   (b) saturating a tissue in the subject in need thereof with the active complex;
   (c) activating the cell functionalizing probe;
   (d) washing the tissue with an aqueous solution to remove unbound active complex;
   (e) repeating steps (a) through (d) from 1 to 100 times;
   (f) separating labeled cells into a suspension of single cells or small cell aggregates;
   (g) optionally sorting and enriching cells comprising a cell functionalizing tag and a cell functionalizing probe via a cell separation method;
   (h) profiling single cell sequences;
   (i) optionally assembling the single cell sequences into a visual representation, wherein the relationship between amplified shared spatial barcodes of single cell sequences is obtained by a computational method;
   (j) optionally using spatial information as a categorical variable for downstream computational analysis.

* * * * *

UNITED STATES PATENT AND TRADEMARK OFFICE
CERTIFICATE OF CORRECTION

PATENT NO. : 11,427,861 B2
APPLICATION NO. : 16/085938
DATED : August 30, 2022
INVENTOR(S) : Alexander K. Shalek et al.

It is certified that error appears in the above-identified patent and that said Letters Patent is hereby corrected as shown below:

On the Title Page

On the page 2, in Column 2, under "Other Publications", Line 1, delete "al. ," and insert -- al., --.

On the page 2, in Column 2, under "Other Publications", Line 4, delete "al. ," and insert -- al., --.

On the page 2, in Column 2, under "Other Publications", Line 41, delete "Mo." and insert -- No. --.

In the Specification

In Column 9, Line 39, delete "thereof," and insert -- thereof; --.

In Columns 19-20, Lines 30-53, after " 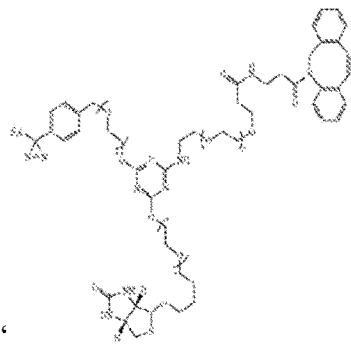 " insert -- . --.

In Column 22, Line 54, delete "cyclooctyne.NH$_2$," and insert -- cyclooctyne•NH$_2$, --.

In Column 47, Line 20, delete "Horibeck," and insert -- Horlbeck, --.

In Column 53, Line 51, delete "10.126" and insert -- 10.1126 --.

In Column 63, Line 30, delete "disulfonicacid;" and insert -- disulfonic acid; --.

Signed and Sealed this
Eighteenth Day of July, 2023

Katherine Kelly Vidal
*Director of the United States Patent and Trademark Office*

CERTIFICATE OF CORRECTION (continued)
U.S. Pat. No. 11,427,861 B2

In Column 72, Line 14, delete "a" and insert -- $\pi$ --.

In Column 74, Line 4, delete "boolean" and insert -- Boolean --.

In Column 79, Line 18, delete "10.126" and insert -- 10.1126 --.

In the Claims

In Column 83, Line 40, in Claim 1, delete "alkynyl" and insert -- alkynyl, --.

In Column 83, Line 44, in Claim 1, after "H;" delete "and".

In Column 83, Line 62, in Claim 3, delete "is is" and insert -- is --.

In Column 84, Line 18, in Claim 5, delete "—$(CH_2)_a NR^8 R^9$," and insert -- —$(CH_2)_a\text{-}NR^8 R^9$, --.

In Column 84, Line 19, in Claim 5, delete "—$CHR^8 R^9$" and insert -- —$CHR^8 R^9$, --.

In Column 84, Lines 27-28, in Claim 5, delete "—$(CH_2)_a NR^{68} C(O)R^9$," and insert -- —$(CH_2)_a\text{-}NR^{68} C(O)R^9$, --.

In Column 84, Line 36, in Claim 5, delete "—$(CH_2)_a C(O)NR^{88} R^{89}$," and insert -- —$(CH_2)_a\text{-}C(O)NR^{88} R^{89}$, --.